US009303051B2

(12) United States Patent
Ware et al.

(10) Patent No.: US 9,303,051 B2
(45) Date of Patent: Apr. 5, 2016

(54) PHOSPHONATE ESTER DERIVATIVES AND METHODS OF SYNTHESIS THEREOF

(71) Applicant: Chimerix, Inc., Durham, NC (US)

(72) Inventors: Roy W. Ware, Raleigh, NC (US);
Merrick R. Almond, Apex, NC (US);
Bernhard M. Lampert, Rougemont, NC (US)

(73) Assignee: Chimerix Inc., Durham, NC (US)

( * ) Notice: Subject to any disclaimer, the term of this patent is extended or adjusted under 35 U.S.C. 154(b) by 0 days.

(21) Appl. No.: 14/808,388

(22) Filed: Jul. 24, 2015

(65) Prior Publication Data

US 2015/0329575 A1    Nov. 19, 2015

Related U.S. Application Data

(63) Continuation of application No. 14/057,391, filed on Oct. 18, 2013, which is a continuation of application No. 13/223,249, filed on Aug. 31, 2011, now Pat. No. 8,569,321.

(60) Provisional application No. 61/378,743, filed on Aug. 31, 2010.

(51) Int. Cl.
*A61K 31/675* (2006.01)
*C07F 9/40* (2006.01)
*C07F 9/38* (2006.01)
*C07F 9/6512* (2006.01)
*C07F 9/6571* (2006.01)

(52) U.S. Cl.
CPC ............ *C07F 9/4021* (2013.01); *A61K 31/675* (2013.01); *C07F 9/3808* (2013.01); *C07F 9/4006* (2013.01); *C07F 9/65121* (2013.01); *C07F 9/657181* (2013.01)

(58) Field of Classification Search
CPC .......................... C07F 9/65121; A61K 31/675
See application file for complete search history.

(56) References Cited

U.S. PATENT DOCUMENTS

| | | | | |
|---|---|---|---|---|
| 6,716,825 B2* | 4/2004 | Hostetler | ............. | C07F 9/3873 435/1.1 |
| 7,034,014 B2* | 4/2006 | Hostetler | ............. | C07F 9/3873 514/110 |
| 7,094,772 B2* | 8/2006 | Hostetler | ............. | C07F 9/3873 514/110 |
| 7,098,197 B2* | 8/2006 | Hostetler | ............. | C07F 9/3873 514/110 |
| 7,452,898 B2* | 11/2008 | Hostetler | ............. | C07F 9/3873 514/274 |
| 7,687,480 B2* | 3/2010 | Hostetler | ............. | C07F 9/3873 514/86 |
| 7,749,983 B2 | 7/2010 | Hostetler et al. | | |
| 7,790,703 B2* | 9/2010 | Hostetler | ............. | C07F 9/3873 514/110 |
| 8,008,308 B2* | 8/2011 | Hostetler | ............. | C07F 9/3873 514/81 |
| 8,309,565 B2* | 11/2012 | Hostetler | ............. | C07F 9/3873 514/274 |
| 8,569,321 B2* | 10/2013 | Ware | ............. | C07F 9/3808 514/274 |
| 8,642,577 B2 | 2/2014 | Almond et al. | | |
| 8,710,030 B2* | 4/2014 | Hostetler | ............. | C07F 9/3873 514/81 |
| 8,889,658 B2* | 11/2014 | Hostetler | ............. | C07F 9/3873 514/86 |
| 8,962,829 B1* | 2/2015 | Ware, Jr. | ............. | C07F 9/65121 544/243 |
| 2002/0025980 A1 | 2/2002 | Katz et al. | | |
| 2004/0019232 A1* | 1/2004 | Hostetler | ............. | C07F 9/3873 558/190 |
| 2004/0127735 A1* | 7/2004 | Hostetler | ............. | C07F 9/3873 558/177 |
| 2005/0176673 A1* | 8/2005 | Hostetler | ............. | C07F 9/3873 514/45 |
| 2005/0182019 A1* | 8/2005 | Hostetler | ............. | C07F 9/3873 514/46 |
| 2005/0192246 A1 | 9/2005 | Hostetler et al. | | |
| 2006/0281706 A1* | 12/2006 | Hostetler | ............. | C07F 9/3873 514/47 |
| 2007/0003516 A1 | 1/2007 | Almond et al. | | |
| 2007/0003608 A1 | 1/2007 | Almond et al. | | |
| 2007/0161602 A1* | 7/2007 | Hostetler | ............. | C07F 9/3873 514/81 |
| 2008/0009462 A1 | 1/2008 | Hostetler et al. | | |
| 2008/0103115 A1* | 5/2008 | Hostetler | ............. | C07F 9/3873 514/81 |
| 2008/0221061 A1 | 9/2008 | Hostetler et al. | | |
| 2010/0173870 A1* | 7/2010 | Hostetler | ............. | C07F 9/3873 514/81 |
| 2011/0015149 A1 | 1/2011 | Almond et al. | | |
| 2011/0263536 A1 | 10/2011 | Lanier et al. | | |
| 2012/0010170 A1 | 1/2012 | Painter | | |
| 2012/0058975 A1* | 3/2012 | Hostetler | ............. | C07F 9/3873 514/81 |
| 2012/0058976 A1* | 3/2012 | Ware | ............. | C07F 9/3808 514/86 |

(Continued)

FOREIGN PATENT DOCUMENTS

WO    WO 92/02511 A1    2/1992
WO    WO 01/39724 A2    6/2001

(Continued)

OTHER PUBLICATIONS

K.Y. Hostetler, 82 Antiviral Research, A84-A-98 (2009).*

(Continued)

*Primary Examiner* — Alexander R Pagano
(74) *Attorney, Agent, or Firm* — Cooley LLP; Ivor R. Elrifi; Heidi A. Erlacher

(57) ABSTRACT

The disclosure describes methods of synthesis of phosphonate ester derivatives. Preferred methods according to the disclosure allow for large-scale preparation of phosphonate ester compounds having high purity. In some embodiments, preferred methods according to the disclosure also allow for the preparation of phosphonate ester derivatives without the use of chromatographic purification methods and in better yield than previously used methods for preparing such compounds. Also disclosed are morphic forms of phosphonate ester derivatives.

9 Claims, 14 Drawing Sheets

(56) References Cited

U.S. PATENT DOCUMENTS

| | | | | |
|---|---|---|---|---|
| 2012/0164104 | A1* | 6/2012 | Lanier | C07F 9/65121 424/85.5 |
| 2012/0165295 | A1 | 6/2012 | Painter et al. | |
| 2013/0045950 | A1* | 2/2013 | Hostetler | C07F 9/3873 514/81 |
| 2013/0072458 | A1 | 3/2013 | Painter et al. | |
| 2014/0045794 | A1* | 2/2014 | Hostetler | C07F 9/3873 514/81 |
| 2014/0046085 | A1* | 2/2014 | Ware | C07F 9/3808 558/45 |
| 2014/0303092 | A1* | 10/2014 | Painter | A61K 31/675 514/20.5 |
| 2015/0051174 | A1* | 2/2015 | Hostetler | C07F 9/3873 514/81 |
| 2015/0087619 | A1* | 3/2015 | Painter, Jr. | A61K 31/675 514/86 |
| 2015/0210724 | A1* | 7/2015 | Ware, Jr. | C07F 9/65121 544/243 |
| 2015/0329575 | A1* | 11/2015 | Ware | C07F 9/65121 514/86 |

FOREIGN PATENT DOCUMENTS

| | | |
|---|---|---|
| WO | WO 2005/087788 A2 | 9/2005 |
| WO | WO 2006/110655 A2 | 10/2006 |
| WO | WO 2006/110656 A2 | 10/2006 |
| WO | WO 2007/130783 A2 | 11/2007 |
| WO | WO 2008/133966 A1 | 11/2008 |
| WO | WO 2011/011519 A1 | 1/2011 |
| WO | WO 2011/017253 A1 | 2/2011 |
| WO | WO 2011/053812 A1 | 5/2011 |

OTHER PUBLICATIONS

K. Toth et al., 17 Cancer Gene Therapy, 761-770 (2010).*
Preformulation in Solid Dosage Form Development (M. C. Adeyeye et al., eds., 2008).*
Solid State Characterization of Pharmaceuticals 427-450 (R.A. Storey et al., eds., 2011).*
Stieger N. et al., Recrystallization of Active Pharmaceutical Ingredients (2012).
Blanchere et al., "X-Ray Diffraction Methods for the Characterization of Solid Pharmaceutical Materials", Preformulation in Solid Dosage Form Development, Boca Raton, FL: CRC Press, Adeyeye et al., eds. 3.4:239-240 (2008).
Braga D. et al., "Crystal Polymorphism and Multiple Crystal Forms", Molecular Networks: Structure Bonding, vol. 132, 25-50 (2009).
Brittain H.G., "Preparation and Identification of Polymorphs and Solvatemorphs", Preformulation in Solid Dosage Form Development 185-228 (M. C. Adeyeye et al., eds., 2008).
Cote A. et al., Organic Process Research & Development, vol. 13, 1276-1283 (2009).
Cains, P.W., "Classical Methods of Preparation of Polymorphs and Alternative Solid Forms", Poylmorphism in Pharmaceutical Solids, 2nd Ed., Drugs and the Pharmaceutical Sciences, Informa Healthcare USA, Inc., New York, NY, 4:76-138 (H.G. Brittain ed., 2nd ed., 2009).
Caira, M.R., "Crystalline Polymorphism of Organic Compounds", Topics in Current Chemistry, 198:163-208 (1998).
Guillory J.K., "Generation of Polymorphs, Hydrates, Solvates, and Amorphous Solids", Polymorphism Inpharmaceutical Solids, 183-220, 188 (H.G. Brittain ed., 1999).
Hostetler et al., Advances in Antiviral Drug Design, vol. 5, 167-184 (2007).
Karpinski P.H. et al., 29 Chemical Engineering & Technology, 233-237 (2006).
Kern et al. "Enhanced Inhibition of Orthopoxvirus Replication In Vitro by Alkoxyalkyl Esters of Cidofovir and Cyclic Cidofovir", Antimicrob. Agents Chemo. 46.4(2002):991-995.
Leonard et al., Advanced Practical Organic Chemistry, 128-226 (2nd ed., 1995).
Lu J.L. et al., Current Medicinal Chemistry, vol. 16, 884-905 (2009).
Miller J.M. et al., Pharmaceutical Development and Technology, vol. 10, 291-297 (2005).
Morissette et al. "High-Throughput Crystallization: Polymorphs, Salts, Co-Crystals and Solvates of Pharmaceutical Solids", Adv. Drug Deliv. Rev. 56(2004):275-300.
Price, S.L., "Computational Methodologies: Toward Crystal Structure and Polymorph Prediction", Poylmorphism in Pharmaceutical Solids, 2nd Ed., Drugs and the Pharmaceutical Sciences, Informa Healthcare USA, Inc., New York, NY, 3:52-75 (H.G. Brittain ed., 2nd ed., 2009).
Polymorphism in Pharmaceutical Solids at 1-23 (H.G. Brittain ed., 2nd ed., 2009).
Sohn Y.T. et al., Archives of Pharmaceutical Research, vol. 31, 231-234 (2008).
Stahly G.P. et al., Crystal Growth and Design, vol. 7, 1007-1026 (2007).
Valiaeva, N. et al., "Synthesis and antiviral evaluation of alkoxyalkyl esters of acyclic purine and pyrimidine nucleoside phosphonates against HIV-1 in vitro", Antiviral Research, 72(1):10-19 (2006).
Vippagunta et al. "Crystalline Solids", Adv. Drug Deliv. Rev. 48(2001):3-26.
Vrbkova, S. et al., "Synthesis of phosphonomethoxyethyl 1,3-bis(phosphonomethoxy) propan-2-yl lipophilic esters of acyclic nucleoside phosphonates", Tetrahedron, 63(46):11391-11398 (2007).
Wan W.B. et al., Antimicrobial Agents and Chemotherapy, 656-662 (2005).

* cited by examiner

PHOSPHONATE ESTER DERIVATIVES AND METHODS OF SYNTHESIS THEREOF

CROSS REFERENCE

This application is a continuation of U.S. Non-Provisional application Ser. No. 14/057,391, filed Oct. 18, 2013, which is a continuation of U.S. Non-Provisional application Ser. No. 13/223,249, filed Aug. 31, 2011 (now U.S. Pat. No. 8,569,321, issued on Oct. 29, 2013), which claims priority to and the benefit of U.S. Provisional Patent Application Ser. No. 61/378,743, filed on Aug. 31, 2010, each of which is incorporated by reference herein in its entirety.

STATEMENT REGARDING FEDERALLY SPONSORED RESEARCH DEVELOPMENT

This invention was made with government support under Grant No. 5U01AI057233 awarded by the National Institutes of Health. The government has certain rights in this invention.

TECHNICAL FIELD

This disclosure relates generally to methods suitable for synthesizing substituted tosyloxymethyl phosphonate compounds. The invention finds utility, for example, in the fields of synthetic organic chemistry and pharmaceutical science.

BACKGROUND

The prodrug approach has been utilized widely since the late 1950s for increasing drug bioavailability as well as drug targeting after oral administration. A prodrug is a compound that undergoes transformation within the body before eliciting a therapeutic action. This strategy is based on chemically modifying an active substance by attaching prodrug-moieties to a pharmacologically active form, which ideally should overcome the biochemical and physical barriers impeding drug transport of the parent substance. Limited oral bioavailability is usually attributed to poor membrane permeability, low aqueous solubility (in the gastrointestinal fluids), or extensive first-pass metabolism.

It was long thought that intestinal absorption of most drugs proceeded by passive diffusion, in which the lipid solubility of the drug molecule was the determining factor. However, many water-soluble compounds have been shown to move well across cell membranes utilizing specialized carrier-mediated transport mechanisms. These membrane transporters play a key role in determining exposure of cells or organisms to a variety of solutes including nutrients and cellular byproducts, as well as drug molecules. Efforts have been made to improve drug bioavailability by using different pro-moieties targeting various active transportation systems present in the small intestine. Examples of transportation systems include peptide transporters, organic cation transporters, organic anion transporters, glucose transporters, vitamin transporters, bile acid transporters, fatty acid transporters, phosphate transporters, monocarboxylic acid transporters, bicarbonate transporters, ABC transporters, nucleoside transporters and amino acid transporters, as described by H.-C. Shi et al, in: R. Mannhold, H. Kubinyi, G. Folkers, Eds., Methods and Principles in Medicinal Chemistry, Wiley-VCH, Weinheim, 2003; pp. 245 287, herein incorporated by reference. All of these transporters are mainly located in the brush border membrane with variable distribution along the gastrointestinal tract, and show diverse substrate specificities.

Cidofovir[(S)-1-(3-hydroxy-2-phosphonylmethoxypropyl)cytosine, HPMPC] has been approved in the clinic as a treatment for AIDS-related cytomegalovirus retinitis. Cidofovir is known for its broad-spectrum activity against virtually all DNA viruses. It has been shown to have therapeutic potential not only against cytomegalovirus, but also against other herpes viruses such as herpes simplex virus (HSV), varcella-zoster virus (VZV), Epstein-Barr virus (EBV) and human herpes virus types 6, 7, and 8. It also has anti-viral activity against adenoviruses, papovaviruses such as papillomavirus and polyomavirus, pox viruses such as variola virus (the etiological agent for small pox) and other orthopox viruses such as monkeypox virus and iridiovirus.

The present invention, in part, provides methods for synthesizing lipid prodrugs of cidofovir. An ideal method of synthesizing cidofovir derivatives would, for example, provide product compounds in high purity and high yield. Preferably, such methods would avoid or minimize the use of purification by chromatographic methods. The present invention is directed at providing one or more of these desirable features.

SUMMARY OF THE DISCLOSURE

The present disclosure describes a morphic form (Form A) of phosphonic acid, [[(S)-2-(4-amino-2-oxo-1(2H)-pyrimidinyl)-1-(hydroxymethyl)ethoxy]methyl]mono[3-(hexadecyloxy)propyl]ester (herein "CMX001"). Form A of CMX001 is characterized by an X-ray diffraction pattern including peaks at about 5.5, 19.3, 20.8, and 21.3 degrees 2θ.

In one embodiment, Form A is characterized by an X-ray diffraction pattern further including peaks at about 17.8 and 23.3 degrees 2θ.

In one embodiment, Form A is characterized by an X-ray diffraction pattern including peaks at about 5.5, 17.8, 19.3, 20.8, 21.3, and 23.3 degrees 2θ.

In one embodiment, Form A is characterized by an X-ray diffraction pattern including peaks at about 5.5, 13.5, 17.8, 19.0, 19.3, 20.5, 20.8, 21.3, 23.3, 23.9, 24.9, and 25.9 degrees 2θ.

In one embodiment, Form A is characterized by an X-ray diffraction pattern including peaks at about 5.5, 11.0, 13.5, 14.3, 17.8, 18.3, 19.0, 19.3, 20.2, 20.5, 20.8, 21.3, 22.1, 22.7, 23.3, 23.9, 24.3, 24.9, 25.6, and 25.9 degrees 2θ.

In another embodiment, Form A is characterized by an X-ray diffraction pattern substantially similar to that set forth in FIG. 4.

In another embodiment, Form A is produced by a purification process comprising recrystallizing a crude preparation of the phosphonic acid, [[(S)-2-(4-amino-2-oxo-1(2H)-pyrimidinyl)-1-(hydroxymethyl)ethoxy]methyl]mono[3-(hexadecyloxy)propyl]ester from an organic solvent, such as alcohol (e.g., methanol, ethanol, and isopropanol). Preferably, the organic solvent is methanol.

In one embodiment, Form A has a purity of greater than 91%, e.g., greater than 92.5%, greater than 95%, greater than 96%, greater than 97%, or greater than 97.5%.

In one embodiment, Form A has a purity of greater than 98%, e.g., greater than 98.5%, greater than 99%, greater than 99.2%, greater than 99.5%, or greater than 99.8%.

In another embodiment, Form A has less than 1.5% of $N^4$-alkylated material, e.g., less than 1.0% of $N^4$-alkylated material, or less than 0.5% of $N^4$-alkylated material.

In another embodiment, Form A is free of $N^4$-alkylated material.

The present disclosure also describes methods for preparing substituted phosphonic acid esters. In one embodiment, for example, the disclosure describes methods for preparing CMX001, e.g., Form A of CMX001. It is preferred that such methods allow for preparation of CMX001 (e.g., Form A) in high purity and on a large-scale without the need for purification by chromatography.

In one embodiment, then, the disclosure describes an improved method for preparing phosphonic acid, [[(S)-2-(4-amino-2-oxo-1(2H)-pyrimidinyl)-1-(hydroxymethyl) ethoxy]methyl]mono[3-(hexadecyloxy)propyl]ester (CMX001). An improvement comprises treating (S)-$N^1$-[(2-hydroxy-3-triphenylmethoxy)propyl]cytosine (herein "CMX212") with magnesium di-tert-butoxide then treating with phosphonic acid, P-[[[(4-methylphenyl)sulfonyl]oxy] methyl]-, mono[3-(hexadecyloxy)propyl]ester, sodium salt (herein "CMX203") to form phosphonic acid, [[(S)-2-(4-amino-2-oxo-1(2H)-pyrimidinyl)-1-(hydroxymethyl)-2-(triphenylmethoxy)ethyl]methyl]mono[3-(hexadecyloxy) propyl]ester (herein "CMX225"). The phosphonic acid, [[(S)-2-(4-amino-2-oxo-1(2H)-pyrimidinyl)-1-(hydroxymethyl)-2-(triphenylmethoxy)ethyl]methyl]mono[3-(hexadecyloxy)propyl]ester (CMX225) is reacted with a protecting-group removal agent to provide phosphonic acid, [[(S)-2-(4-amino-2-oxo-1(2H)-pyrimidinyl)-1-(hydroxymethyl) ethoxy]methyl]mono[3-(hexadecyloxy)propyl]ester (CMX001).

In another embodiment, the disclosure provides a method for synthesizing purified phosphonic acid, [[(S)-2-(4-amino-2-oxo-1(2H)-pyrimidinyl)-1-(hydroxymethyl)ethoxy]methyl]mono[3-(hexadecyloxy)propyl]ester (CMX001), the method comprising:
   (a) contacting cytosine with (S)-trityl glycidyl ether in the presence of a metal carbonate and a first suitable organic solvent to form (S)-$N^1$-[(2-hydroxy-3-triphenylmethoxy)propyl]cytosine (CMX212);
   (b) contacting (S)-$N^1$-[(2-hydroxy-3-triphenylmethoxy) propyl]cytosine (CMX212) with phosphonic acid, P-[[[(4-methylphenyl)sulfonyl]oxy]methyl]-, mono[3-(hexadecyloxy)propyl]ester, sodium salt (CMX203) in the presence of magnesium di-tert-butoxide and a second suitable organic solvent to form phosphonic acid, [[(S)-2-(4-amino-2-oxo -1(2H)-pyrimidinyl)-1-(hydroxymethyl)-2-(triphenylmethoxy)ethyl]methyl] mono[3-(hexadecyloxy)propyl]ester (CMX225);
   (c) contacting phosphonic acid, [[(S)-2-(4-amino-2-oxo-1 (2H)-pyrimidinyl)-1-(hydroxymethyl)-2-(triphenylmethoxy)ethyl]methyl]mono[3-(hexadecyloxy)propyl] ester (CMX225) with a protecting-group removal agent in the presence of methanol to form crude phosphonic acid, [[(S)-2-(4-amino-2-oxo-1(2H)-pyrimidinyl)-1-(hydroxymethyl)ethoxy]methyl]mono[3-(hexadecyloxy)propyl]ester (CMX001); and
   (d) recrystallizing the crude phosphonic acid, [[(S)-2-(4-amino-2-oxo-1(2H) -pyrimidinyl)-1-(hydroxymethyl) ethoxy]methyl]mono[3-(hexadecyloxy)propyl]ester (CMX001) in a third suitable organic solvent.

The present disclosure also describes methods for preparing substituted tosyloxymethyl phosphonate compounds. In one embodiment, for example, the disclosure describes methods for preparing phosphonic acid, P-[[[(4-methylphenyl) sulfonyl]oxy]methyl]-, mono[3-(hexadecyloxy)propyl]ester, sodium salt (CMX203). It is preferred that such methods allow for preparation of CMX203 in high purity and on a large-scale without the need for purification by chromatography.

In another embodiment, then, the disclosure describes an improved method for preparing phosphonic acid, P-[[[(4-methylphenyl)sulfonyl]oxy]methyl]-, mono[3-(hexadecyloxy)propyl]ester, sodium salt (CMX203). The improvement comprises quenching a reaction of an alkoxyalkanol and (dichlorophosphoryl)methyl 4-methylbenzenesulfonate with sodium bicarbonate followed by adjusting the pH to 2.0 before separation of the desired product. The desired product is separated using dichloromethane and concentrated. Following concentration, the desired product is re-dissolved in 2-propanol and sodium hydroxide is added. Precipitation of the desired product from 2-propanol is completed.

In another embodiment, the disclosure provides a method for synthesizing phosphonic acid, P-[[[(4-methylphenyl)sulfonyl]oxy]methyl]-, mono[3-(hexadecyloxy)propyl]ester, sodium salt (CMX203) in high yield, the method comprising:
   (a) contacting (dichlorophosphoryl)methyl 4-methylbenzenesulfonate with 3-(hexadecyloxy)propan-1-ol in the presence of a base (such as pyridine or triethylamine or a mixture thereof) in a first suitable solvent to form a resultant mixture;
   (b) quenching the resultant mixture with a suitable quenching agent and water;
   (c) adjusting the pH of the quenched resultant mixture to 2.0 to form a crude product; and
   (d) dissolving the crude product in a second suitable solvent.

In some embodiments, the phosphonic acid, P-[[[(4-methylphenyl)sulfonyl]oxy]methyl]-, mono[3-(hexadecyloxy) propyl]ester, sodium salt (CMX203) is synthesized with a yield greater than or equal to about 73% with respect to 3-(hexadecyloxy)propan-1-ol.

In another embodiment, the disclosure provides a method for synthesizing hexadecyl methanesulfonate in high yield, the method comprising contacting 1-hexadecanol with methanesulfonyl chloride in the presence of an amine in a suitable solvent.

In another embodiment, the disclosure provides a method for synthesizing 3-(hexadecyloxy)propan-1-ol in high yield, the method comprising contacting 1,3-propanediol with hexadecyl methanesulfonate in the presence of a metal hydride in N-methyl pyrrolidinone (NMP).

In another embodiment, the disclosure describes a method for synthesizing phosphonic acid, P-[[[(4-methylphenyl)sulfonyl]oxy]methyl]-, mono[3-(hexadecyloxy)propyl]ester, sodium salt (CMX203). The method comprises contacting (dichlorophosphoryl)methyl 4-methylbenzenesulfonate with 3-(hexadecyloxy)propan-1-ol in the presence of pyridine in a suitable solvent to form a resultant mixture. The resultant mixture is quenched with a quenching agent and water. The quenched resultant mixture is then adjusted to a pH of 2, forming a crude product. The crude product is then dissolved in 2-propanol and sodium hydroxide to provide 3-(hexadecyloxy)propyl tosyloxymethylphosphonate.

In still another embodiment, the disclosure describes a method for synthesizing phosphonic acid, P-[[[(4-methylphenyl)sulfonyl]oxy]methyl]-, mono[3-(hexadecyloxy) propyl]ester, sodium salt (CMX203). The method comprises contacting (dichlorophosphoryl)methyl 4-methylbenzenesulfonate with an alkoxyalkanol in the presence of a suitable base in a suitable solvent to produce an alkoxyalkyl substituted tosyloxymethyl phosphonate. The alkoxyalkyl substituted tosyloxymethylphosphonate is quenched with a quenching agent and water. The quenched alkoxyalkyl substituted tosyloxymethyl phosphonate is then adjusted to a pH of 2, forming a crude product. The crude product is then dissolved in a recrystallization agent and sodium hydroxide to provide the desired alkoxyalkyl substituted tosyloxymethylphosphonate.

In another embodiment, the second suitable solvent in step (d) is further treated with sodium hydroxide.

In a further embodiment, the alkoxyalkanol is 3-(hexadecyloxy)propan-1-ol, the suitable base is pyridine, the suitable solvent is dichloromethane, the quenching agent is sodium bicarbonate, and the recrystallization agent is 2-propanol.

In another embodiment, the disclosure provides a method for synthesizing (dichlorophosphoryl)methyl 4-methylbenzenesulfonate by:
(a) contacting diethyl (tosyloxy)methyloxyphosphonate and acetonitrile with bromotrimethylsilane and heating to form a resultant mixture; and
(b) adding dichloromethane and oxalyl chloride to the resultant mixture to form the (dichlorophosphoryl)methyl 4-methylbenzenesulfonate.

In another embodiment, a catalyst (e.g., N,N-dimethylformamide) is added to the resultant mixture of step (b) to form the (dichlorophosphoryl)methyl 4-methylbenzenesulfonate.

In another embodiment, the disclosure provides a method for synthesizing 3-(hexadecyloxy)propan-1-ol by:
(a) contacting 1,3-propanediol in N-methyl pyrrolidinone with sodium hydride to form a resultant mixture; and
(b) adding a solution of hexadecyl methanesulfonate dissolved in N-methyl pyrrolidinone to form the 3-(hexadecyloxy)propan-1-ol.

In another embodiment, the disclosure provides a method for synthesizing hexadecyl methanesulfonate by:
(a) contacting 1-hexadecanol, dichloromethane and diisopropylethylamine to form a resultant mixture; and
(b) adding methanesulfonyl chloride to the resultant mixture to form the hexadecyl methanesulfonate.

In another aspect, the disclosure provides a method for synthesizing CMX001 (e.g., Form A) by:
(a) contacting (S)-$N^1$-[(2-hydroxy-3-(PG-O)-propyl]cytosine with phosphonic acid, P-[[[(4-methylphenyl)sulfonyl]oxy]methyl]-, mono[3-(hexadecyloxy)propyl]ester, sodium salt in the presence of magnesium di-tert-butoxide and a suitable organic solvent A to form [3-(hexadecyloxy)propyl]hydrogen[[[(S)-1-(4-amino-2-oxopyrimidin-1(2H)-yl)-3-(PG-O)-propan -2-yl]oxy]methyl]phosphonate; and
(b) contacting [3-(hexadecyloxy)propyl]hydrogen[[[(S)-1-(4-amino-2-oxopyrimidin-1(2H)-yl)-3-(PG-O)-propan-2-yl]oxy]methyl]phosphonate with a protecting-group removal agent in the presence of a suitable organic solvent B to form phosphonic acid, [[(S)-2-(4-amino-2-oxo-1(2H)-pyrimidinyl)-1-(hydroxymethyl)ethoxy]methyl]mono[3-(hexadecyloxy)propyl]ester; wherein PG is a hydroxyl protecting group.

In one embodiment, PG is removable under acidic conditions.

In one embodiment, PG triphenylmethyl, monomethoxytrityl or dimethoxytrityl.

In one embodiment, the protecting-group removal agent is hydrogen chloride.

In one embodiment, the suitable organic solvent A is N,N-dimethylformamide.

In one embodiment, the magnesium di-tert-butoxide has a purity of greater than 98%.

In one embodiment, the suitable solvent B is an alcohol, such as methanol.

In one embodiment, the method further comprises recrystallizing the phosphonic acid, [[(S)-2-(4-amino-2-oxo-1 (2H)-pyrimidinyl)-1-(hydroxymethyl)ethoxy]methyl]mono[3-(hexadecyloxy)propyl]ester in a suitable recrystallizing organic solvent.

In one embodiment, the suitable recrystallizing organic solvent is non-aqueous.

In one embodiment, the suitable recrystallizing organic solvent is non-toxic.

In one embodiment, the suitable recrystallizing organic solvent is pharmaceutically acceptable.

In one embodiment, the suitable recrystallizing organic solvent is methanol.

In one embodiment, the method further comprises synthesizing the (S)-$N^1$-[(2-hydroxy-3-(PG-O)-propyl]cytosine by:
contacting cytosine with (S)-2-(PG-O-methyl)oxirane in the presence of a metal carbonate and a suitable organic solvent C to form (S)-$N^1$-[(2-hydroxy-3-(PG-O)-propyl]cytosine.

In one embodiment, the metal carbonate is potassium carbonate.

In one embodiment, the suitable organic solvent C is N,N-dimethylformamide.

In yet another aspect, the disclosure provides compounds for the treatment of viral infection in a subject, e.g., an immunodeficient subject, having the structure of formula I:

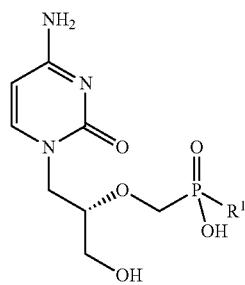

(I)

wherein:
$R^1$ is unsubstituted or substituted $C_1$-$C_6$ alkoxyl, or unsubstituted or substituted $C_1$-$C_{30}$ alkoxy-$C_1$-$C_6$-alkoxyl; or an enantiomer, diastereomer, racemate or a mixture thereof, and the compound of formula (I) has a purity of greater than 91% or is in Form A. In one embodiment, the purity of the compound of formula (I) is >92%, >93%, >94%, >95%, >97.5%, >98%, >99%, or >99.5%. In another embodiment, the compound is in Form A. In yet another embodiment, the compound is in Form A and has a purity of greater than 91% (e.g., >92%, >93%, >94%, >95%, >97.5%, >98%, >99%, or >99.5%). In one embodiment, the compound of formula (I) are obtained from recrystallizing a crude compound from a suitable recrystallizing solvent described herein. In another embodiment, the compound is not a hydrate. In yet another embodiment, the compound is a solvate, e.g., a methanol solvate, an ethanol solvate, or an isopropanol solvate.

In another aspect, the disclosure provides compounds for the prevention of viral infection in a subject, e.g., an immunodeficient subject, having the structure of formula I:

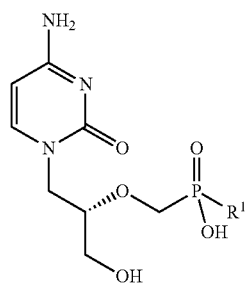

(I)

wherein:
$R^1$ is unsubstituted or substituted $C_1$-$C_6$ alkoxyl, or unsubstituted or substituted $C_1$-$C_{30}$ alkoxy-$C_1$-$C_6$-alkoxyl; or an enantiomer, diastereomer, racemate or a mixture thereof, and the compound of formula (I) has a purity of greater than 91% or is in Form A. In one embodiment, the purity of the compound of formula (I) is >92%, >93%, >94%, >95%, >97.5%, >98%, >99%, or >99.5%. In another embodiment, the compound is in Form A. In yet another embodiment, the compound is in Form A and has a purity of greater than 91% (e.g., >92%, >93%, >94%, >95%, >97.5%, >98%, >99%, or >99.5%). In one embodiment, the compound of formula (I) are obtained from recrystallizing a crude compound from a suitable recrystallizing solvent described herein. In another embodiment, the compound is not a hydrate. In yet another embodiment, the compound is a solvate, e.g., a methanol solvate, an ethanol solvate, or an isopropanol solvate.

In another embodiment, the viral infection to be treated or prevented is resistant to treatment or prevention with other nucleoside phosphonates, e.g., cidofovir, cyclic cidofovir, tenofovir, and adefovir, etc. Alternatively or additionally, such other nucleoside phosphonates (e.g., cidofovir (CDV)) exhibit toxic side effects (e.g., nephrotoxicity) in said immunodeficient subject.

In another embodiment, the subject is infected with at least one virus. The virus may be selected from the group consisting of: human immunodeficiency virus (HIV), influenza, herpes simplex virus (HSV), human herpes virus 6 (HHV-6), cytomegalovirus (CMV), hepatitis B and C virus, Epstein-Barr virus (EBV), varicella zoster virus, variola major and minor, vaccinia, smallpox, cowpox, camelpox, monkeypox, ebola virus, papilloma virus, adenovirus or polyoma viruses including John Cunningham virus (JCV), BK virus and Simian vacuolating virus 40 or Simian virus 40 (SV40). In another embodiment, the subject is infected with at least one dsDNA virus.

In another embodiment, the subject is infected with a virus or any combination of two or more viruses selected from the group consisting of: human CMV (HCMV), BK virus, HHV-6, Adenovirus and EBV.

In another embodiment, the subject is infected with two or more viruses, at least one of which is, for example, a dsDNA virus, and the viruses exhibit synergistic action. For example, the viruses are HCMV and BK.

In another embodiment, a compound of formula (I) having a purity of greater than 91% or being in Form A is used to treat viral infection (e.g., a dsDNA viral infection) in a subject wherein said infection is resistant to valganciclovir hydrochloride (or ganciclovir) or wherein said subject exhibits side effects to valganciclovir hydrochloride (or ganciclovir). Alternatively or additionally, the compound of formula (I) having a purity of greater than 91% or being in Form A is used to treat cytomegalovirus (CMV) subsequent to treatment with ganciclovir, for example, wherein the CMV infection is emergent. The patient may be a bone marrow stem cell transplant patient, especially where there is a risk (real or perceived) for bone marrow toxicity from ganciclovir in the patient.

In another embodiment, the subject is a mammal. In another embodiment, the subject is a human.

In another embodiment, a compound of formula (I) having a purity of greater than 91% or being in Form A is administered orally, for example, at a dosage of about 0.01 mg/kg to about 10 mg/kg or more, e.g., up to 100 mg/kg. In another embodiment, said compound of formula (I) having a purity of greater than 91% or being in Form A is administered to said subject at a dosage of about 0.01, 0.05, 0.1, 0.5, 1, 1.5, 2, 2.5, 3, 3.5, 4, 4.5, 5, 5.5, 6, 6.5, 7, 7.5, 8, 8.5, 9, 9.5, or 10 mg/kg or more or any range therein.

In another embodiment, the disclosure also provides for the use of a compound of formula (I) having a purity of greater than 91% or being in Form A in the manufacture of a medicament for the therapeutic and/or prophylactic treatment of viral infection in a subject, e.g., an immunodeficient subject.

In another embodiment, the disclosure provides a method for the therapeutic and/or prophylactic treatment of viral infection in a subject, e.g., an immunodeficient subject, the method comprising administering a compound of formula (I) having a purity of greater than 91% or being in Form A to the subject.

In another embodiment, the disclosure also provides an oral dosage form comprising a compound of formula (I) having a purity of greater than 91% or being in Form A for the therapeutic and/or prophylactic treatment of viral infection in a subject, wherein said oral dosage form, upon administration to a human at a dosage of 2 mg/kg of said compound, provides an $AUC_{0-inf}$ of said compound of about 2000 to about 4000 h*ng/mL, e.g., about 2500 to about 3000 h*ng/mL.

In another embodiment, the disclosure also provides an oral dosage form comprising a compound of formula (I) having a purity of greater than 91% or being in Form A for the therapeutic and/or prophylactic treatment of viral infection in a subject, wherein said oral dosage form, upon administration to a human at a dosage of 2 mg/kg of said compound, provides a $C_{max}$ of said compound of about 100 to about 500 ng/mL, e.g., about 200 to about 400 h*ng/mL.

In another embodiment, the disclosure also provides an oral dosage form comprising a compound of formula (I) having a purity of greater than 91% or being in Form A for the therapeutic and/or prophylactic treatment of viral infection in a subject, wherein said oral dosage form, upon administration to a human at a dosage of 2 mg/kg of said compound of formula (I) and metabolism of said compound of formula (I) to cidofovir, provides a $C_{max}$ of said cidofovir that is less than about 30% of the $C_{max}$ of said compound of formula (I), e.g., less that about 20% of the $C_{max}$ of said compound of formula (I).

DETAILED DESCRIPTION OF THE INVENTION

Figure 1:
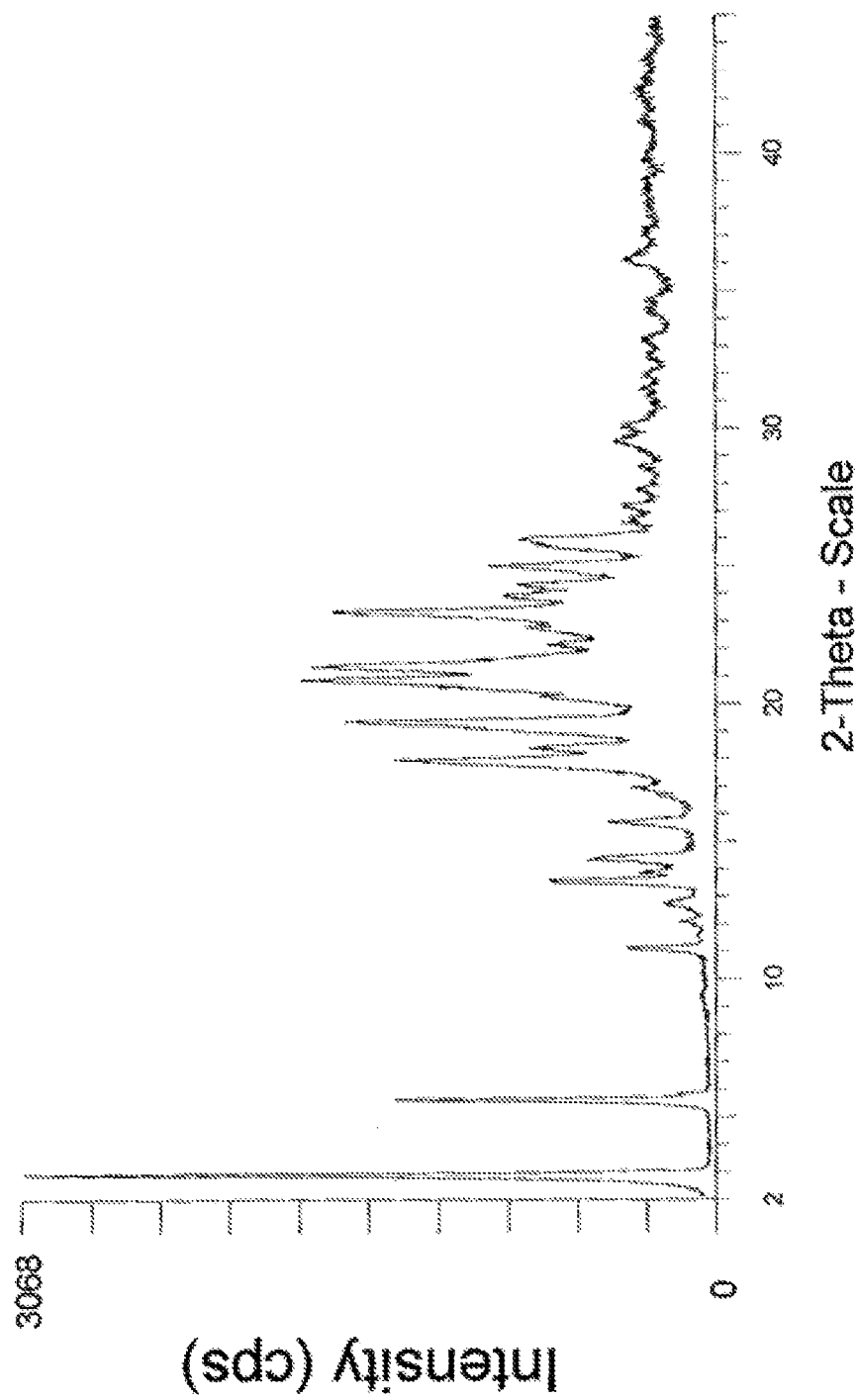
FIG. 1 is an X-ray powder diffractogram (XRD) of CMX001, Form A (Lot#1).
Figure 2:
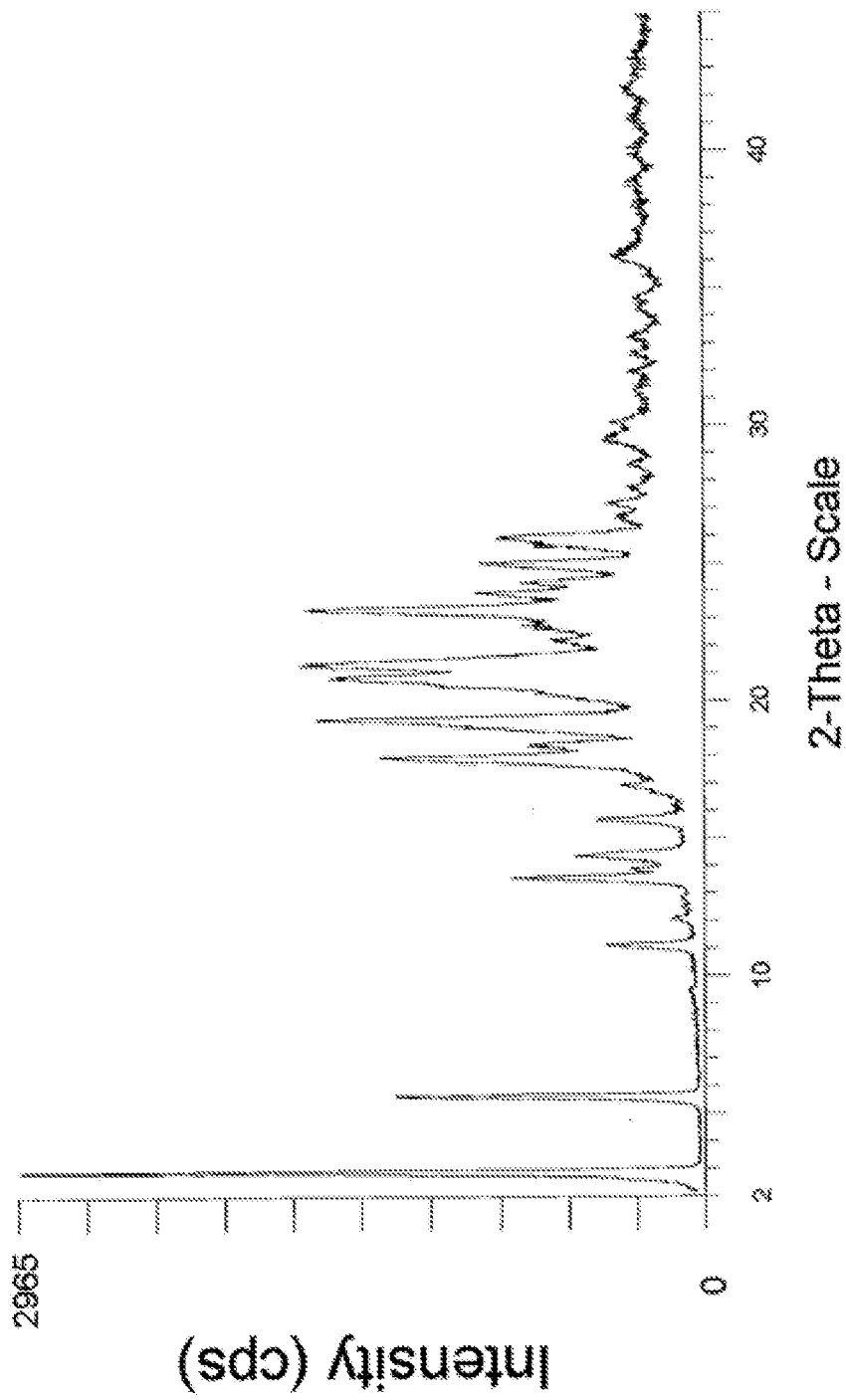
FIG. 2 is an XRD of CMX001, Form A (Lot#2).
Figure 3:
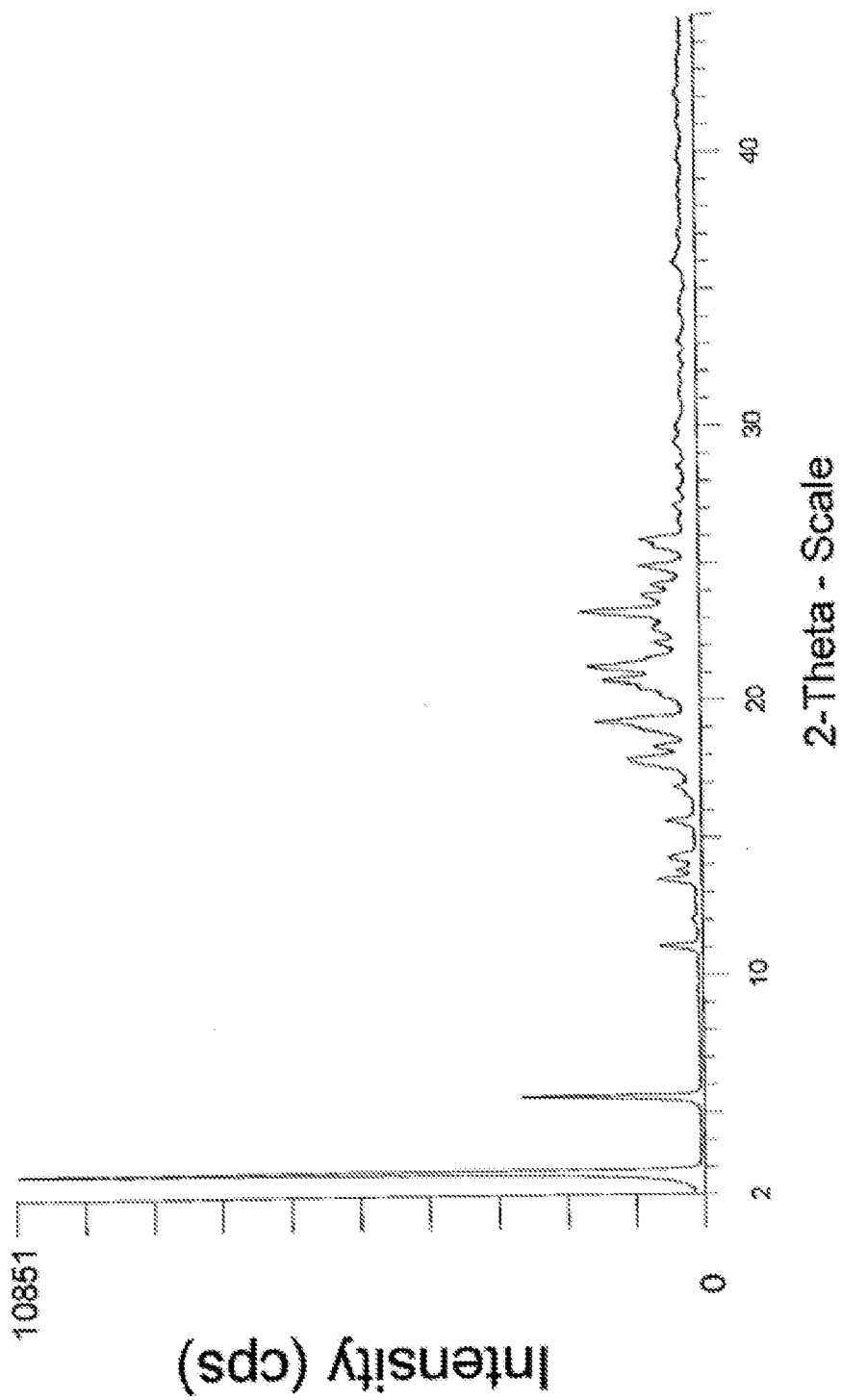
FIG. 3 is an XRD of CMX001, Form A (Lot#3).
Figure 4:
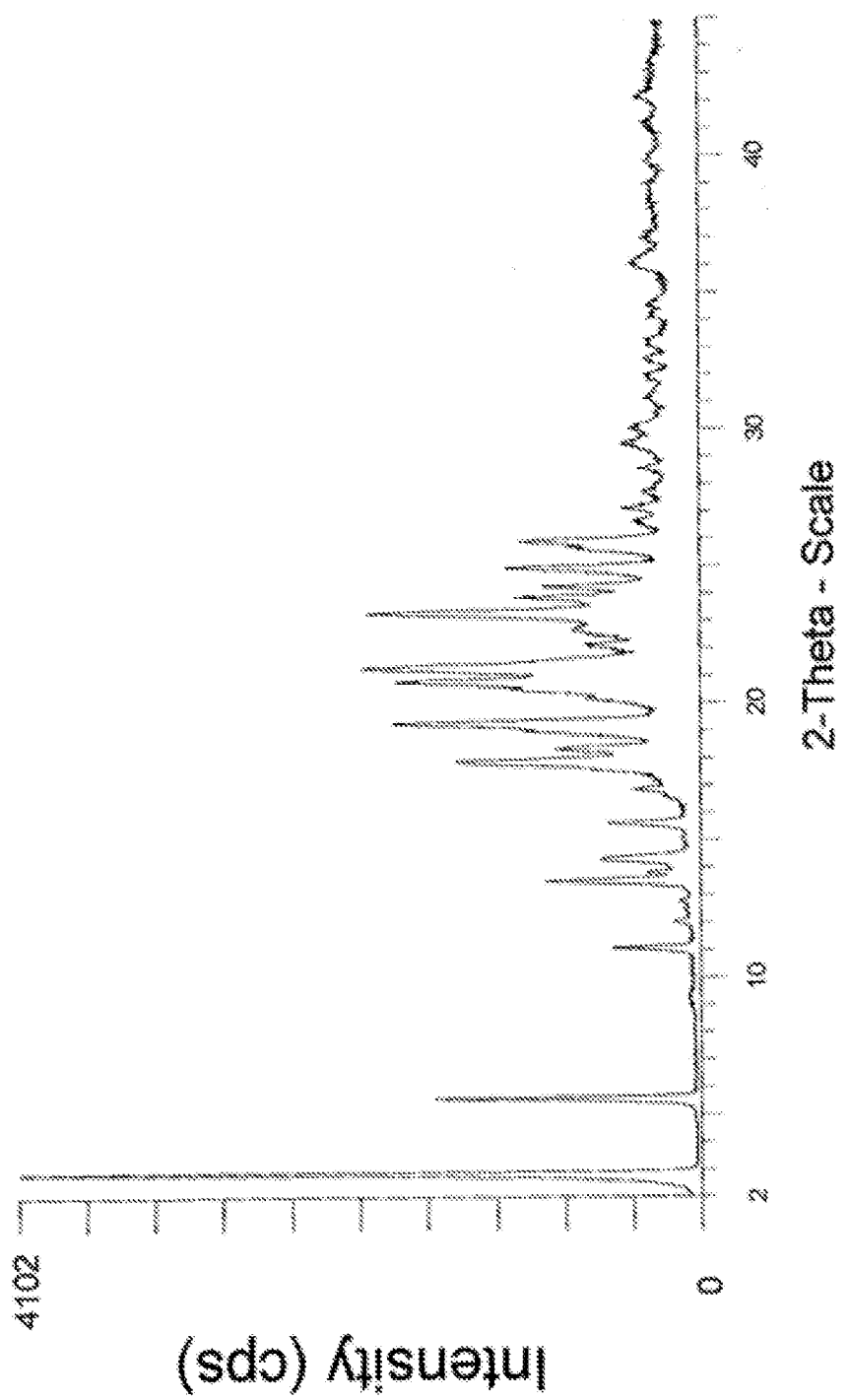
FIG. 4 is an XRD of CMX001, Form A (Lot#4).
Figure 5:
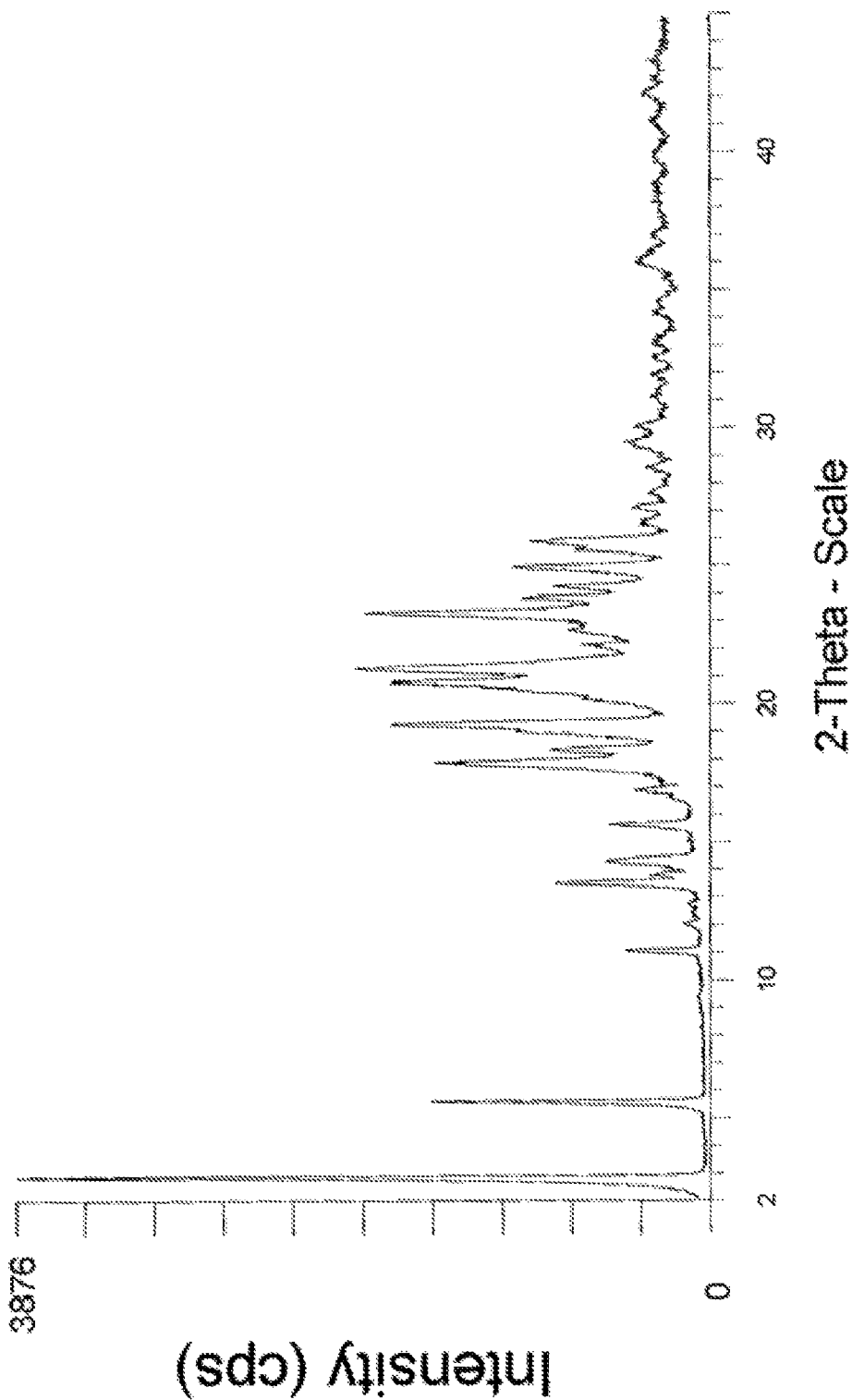
FIG. 5 is an XRD of CMX001, Form A (Lot#5).
Figure 6:
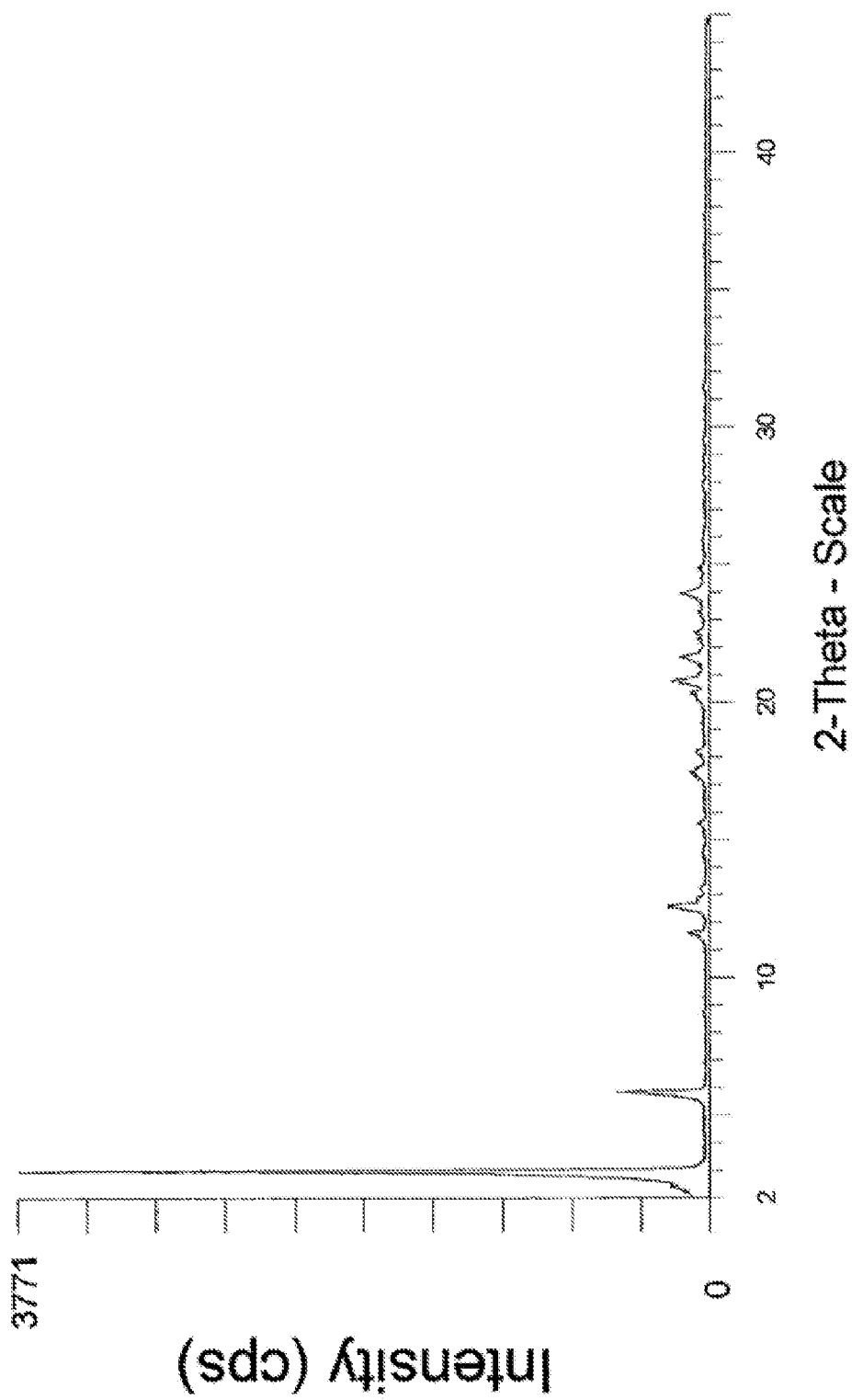
FIG. 6 is an XRD of CMX001, Form B (Lot#6).

As used in the specification and the appended claims, the singular forms "a," "an," and "the" include plural referents unless the context clearly dictates otherwise. Thus, for example, reference to "a reactant" includes not only a single reactant but also a combination or mixture of two or more different reactant, reference to "a substituent" includes a single substituent as well as two or more substituents, and the like.

As used herein, the phrases "for example," "for instance," "such as," or "including" are meant to introduce examples that further clarify more general subject matter. These examples are provided only as an aid for understanding the disclosure, and are not meant to be limiting in any fashion. Furthermore as used herein, the terms "may," "optional," "optionally," or "may optionally" mean that the subsequently described circumstance may or may not occur, so that the description includes instances where the circumstance occurs and instances where it does not. For example, the phrase "optionally present" means that an object may or may not be present, and, thus, the description includes instances wherein the object is present and instances wherein the object is not present.

In describing and claiming the present invention, the following terminology will be used in accordance with the definitions set out below.

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms, for example, 1, 2, 3, 4, 5, or 6 carbon atoms. "Substituted alkyl" refers to alkyl substituted with one or more substituent groups, and the terms "heteroatom-containing alkyl" and "heteroalkyl" refer to an alkyl substituent in which at least one carbon atom is replaced with a heteroatom, as described in further detail infra.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein may, for example, may contain 1 to 3 carbon atoms, and as a further example, such substituents may contain 1 or 2 carbon atoms (i.e., methoxy and ethoxy).

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aralkyl" refers to an alkyl group with an aryl substituent, and the term "alkaryl" refers to an aryl group with an alkyl substituent, wherein "alkyl" and "aryl" are as defined above. In general, aralkyl and alkaryl groups herein contain 6 to 30 carbon atoms. Aralkyl and alkaryl groups may, for example, contain 6 to 20 carbon atoms, and as a further example, such groups may contain 6 to 12 carbon atoms.

The term "amino" is used herein to refer to the group —$NZ^1Z^2$ wherein $Z^1$ and $Z^2$ are hydrogen or nonhydrogen substituents, with nonhydrogen substituents including, for example, alkyl, aryl, alkenyl, aralkyl, and substituted and/or heteroatom-containing variants thereof.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

"Hydrocarbyl" refers to univalent hydrocarbyl radicals containing 1 to about 30 carbon atoms, including 1 to about 24 carbon atoms, further including 1 to about 18 carbon atoms, and further including about 1 to 12 carbon atoms, including linear, branched, cyclic, saturated and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups and the hydrocarbyl moieties $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl).

By "functional group," as alluded to in some of the aforementioned definitions, is meant a non-hydrogen group comprising one or more non-hydrocarbon functionality. Examples of functional groups include, without limitation: halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO— alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$), mono- and di-($C_1$-$C_{24}$ alkyl)-substituted phosphino, mono- and di-($C_5$-$C_{20}$ aryl)-substituted phosphino; and the hydrocarbyl moieties $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

It will be appreciated that some of the abovementioned definitions may overlap, such that some chemical moieties may fall within more than one definition.

When the term "substituted" appears prior to a list of possible substituted groups, it is intended that the term apply to every member of that group. For example, the phrase "substituted alkyl and aryl" is to be interpreted as "substituted alkyl and substituted aryl."

By two moieties being "connected" is intended to include instances wherein the two moieties are directly bonded to each other, as well as instances wherein a linker moiety is present between the two moieties. Linker moieties may include groups such as heteroatoms, $C_1$-$C_{24}$ alkylene (including $C_1$-$C_{18}$ alkylene, further including $C_1$-$C_{12}$ alkylene, and further including $C_1$-$C_6$ alkylene), $C_2$-$C_{24}$ alkenylene (including $C_2$-$C_{18}$ alkenylene, further including $C_2$-$C_{12}$ alkenylene, and further including $C_2$-$C_6$ alkenylene), $C_2$-$C_{24}$ alkynylene (including $C_2$-$C_{18}$ alkynylene, further including $C_2$-$C_{12}$ alkynylene, and further including $C_2$-$C_6$ alkynylene), $C_5$-$C_{30}$ arylene (including $C_5$-$C_{20}$ arylene, and further including $C_5$-$C_{12}$ arylene), and $C_6$-$C_{30}$ aralkylene (including $C_6$-$C_{20}$ aralkylene, and further including $C_6$-$C_{12}$ aralkylene).

The disclosure provides methods of synthesis for substituted phosphonic acid esters. In certain aspects, then, the invention provides methods for the preparation of compounds having the structure of formula (I):

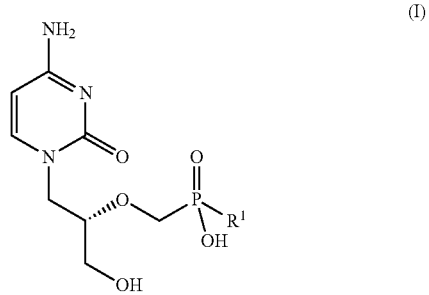

wherein:
$R^1$ is unsubstituted or substituted $C_1$-$C_6$ alkoxy-, or unsubstituted or substituted $C_1$-$C_{30}$ alkoxy-$C_1$-$C_6$-alkoxy-; or an enantiomer, diastereomer, racemate or a mixture thereof.

In another embodiment, $R^1$ is $C_{10}$-$C_{30}$ alkoxy-$C_2$-$C_4$-alkoxy-.

In another embodiment, $R^1$ is hexadecyloxypropyloxy-.

The disclosure also provides methods of synthesis for substituted phosphonates, particularly substituted tosyloxymethyl phosphonates. In certain aspects, then, the invention provides methods for the preparation of compounds having the structure of formula II:

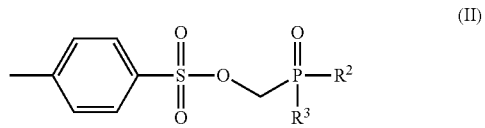

wherein:
$R^2$ is unsubstituted or substituted $C_1$-$C_6$ alkoxy-, or unsubstituted or substituted $C_1$-$C_{30}$ alkoxy-$C_1$-$C_6$-alkoxy-;
$R^3$ is $OR^4$ or $O^-A^+$;
$R^4$ is H, or unsubstituted or substituted $C_1$-$C_6$ alkyl; and
$A^+$ is $Li^+$, $Na^+$, or $K^+$.

In another embodiment, $R^3$ is $O^-A^+$ and $R^2$ is $C_{10}$-$C_{30}$ alkoxy-$C_2$-$C_4$-alkoxy-. For example, $A^+$ is $Na^+$ and $R^2$ is $C_{10}$-$C_{30}$ alkoxy-propyloxy-.

In another embodiment, $R^3$ is $O^-A^+$ and $R^2$ is hexadecyloxypropyloxy-.

Compounds having the structure of formula I are preferably prepared by an alkylation reaction between CMX212 and a compound having the structure of formula II.

Compounds having the structure of formula II are preferably isolated from a suitable solvent, e.g., dichloromethane, following the addition of a quenching agent and adjusting the pH to 2.0.

The present invention provides methods for the synthesis of the compounds of formulae I and II. The present invention also provides detailed methods for the synthesis of various disclosed compounds of the present invention according to the following schemes and as shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester or prodrug thereof.

Procedure A: Synthesis of Phosphonic Acid, [[(S)-2-(4-amino-2-oxo-1(2H)-pyrimidinyl)-1-(hydroxymethyl)ethoxy]methyl]mono[3-(hexadecyloxy)propyl] ester (CMX001)

Scheme 1

Step 1:

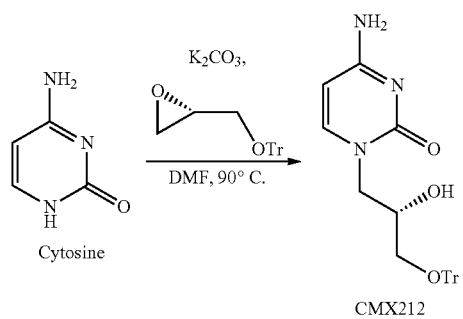

Step 2A:

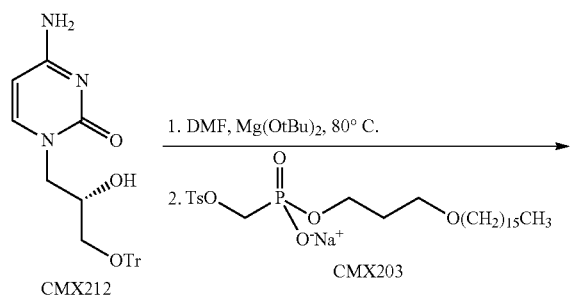

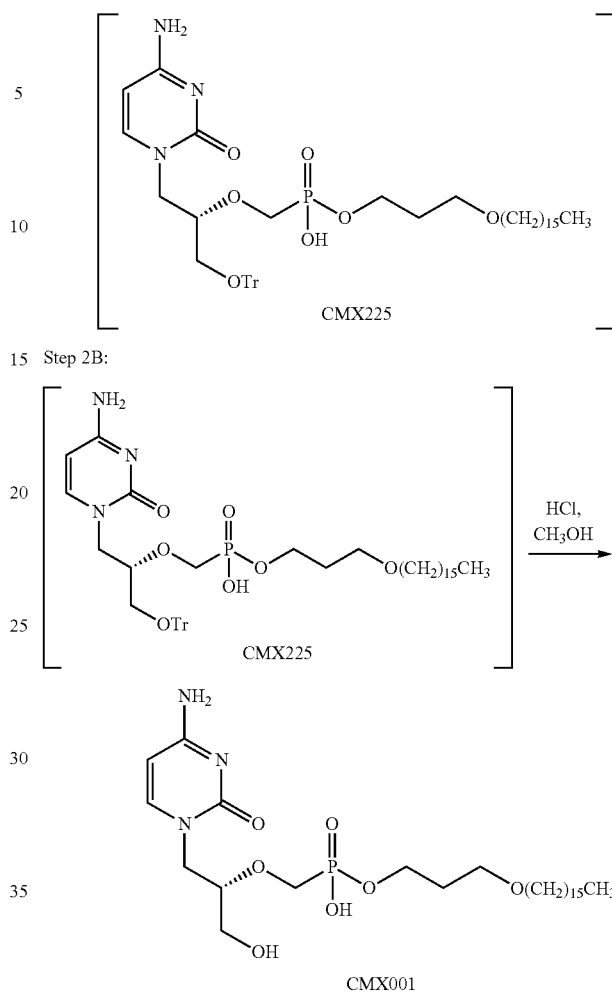

Step 1: Synthesis of (S)-$N^1$-[(2-hydroxy-3-triphenylmethoxy)propyl]cytosine (CMX212)

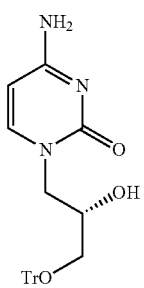

This compound is prepared by contacting cytosine with (S)-trityl glycidyl ether in the presence of a small amount of a suitable base such as a metal carbonate (e.g., potassium carbonate) in a suitable organic solvent (e.g., N,N-dimethylformamide, tert-amyl alcohol)) at a suitable reaction temperature (e.g., 60 to 120° C.) until completion of reaction, typically about 4 to 14 hours, for example about 8 to 10 hours.

Steps 2A and 2B: Synthesis of Phosphonic Acid, [[(S)-2-(4-amino-2-oxo-1(2H)-pyrimidinyl)-1-(hydroxymethyl)ethoxy]methyl]mono[3-(hexadecyloxy)propyl]ester (CMX001)

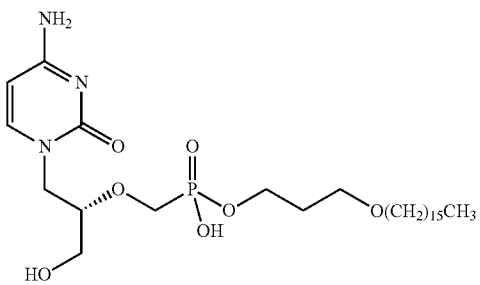

This compound is prepared by contacting CMX212 with CMX203 in the presence of a suitable base such as a metal alkoxide (e.g., magnesium di-tert-butoxide, sodium tert-butoxide, lithium tert-butoxide, sodium tert-amyl alkoxide, potassium tert-butoxide, sodium methoxide), metal hydride (e.g., sodium hydride, potassium hydride), or metal amide (e.g., lithium bis(trimethylsilyl)amide) in a suitable organic solvent (e.g., N,N-dimethylformamide, N,N-dimethylacetamide, dimethylsulfoxide, 1-methyl-2-pyrrolidinone) at a suitable reaction temperature (e.g., 50 to 110° C.) until completion of reaction, typically about 0.25 to five hours, for example about two to four hours. The crude reaction mixture is subjected to an aqueous work-up. The crude product is extracted with a suitable organic solvent (e.g., ethyl acetate, isopropyl acetate, dichloromethane, etc.) and the organic solvent is concentrated to give crude CMX225. The crude CMX225 is contacted with a suitable deprotecting agent (e.g., hydrogen chloride, acetyl chloride) in an organic solvent (e.g., methanol) until completion of reaction, typically one to six hours, for example two to three hours. The crude CMX001 is recrystallized using a suitable solvent system (e.g., methanol/acetone/water, ethanol, methanol). Magnesium di-tert-butoxide is commercially available from Chemetall (Kings Mountain, N.C.).

It will be appreciated that, although a wide variety of reaction conditions are suitable to provide the alkylation of CMX212, certain reaction conditions are most preferred because they yield the greatest amount of product and/or provide a product having the highest purity. In particular, magnesium di-tert-butoxide is a preferred metal alkoxide.

It will be appreciated that a deprotection reaction is required in order to complete the transformation from CMX225 to CMX001. In particular, the 0-protecting group (i.e., trityl) must be removed in order to obtain the free hydroxyl present in CMX001. Thus, in one embodiment, CMX001 is obtained by deprotecting CMX225 with hydrogen chloride gas.

It will be appreciated that, although several methods in the art describing the synthesis of CMX001 result in the formation of a salt of CMX001, e.g., the sodium salt of CMX001, the present invention provides direct methods for synthesizing CMX001 as the free acid without the intermediate salt formation.

One preferred embodiment of the invention is depicted in Procedure A. The procedure describes an improved method for preparing phosphonic acid, [[(S)-2-(4-amino-2-oxo-1(2H)-pyrimidinyl)-1-(hydroxymethyl)ethoxy]methyl]mono[3-(hexadecyloxy)propyl]ester (CMX001). Steps 1, 2A and 2B are described herein.

With reference to Step 1 of Procedure A, (S)-$N^1$-[(2-hydroxy-3-triphenylmethoxy)propyl]cytosine (CMX212) is prepared by contacting cytosine with (S)-trityl glycidyl ether in the presence of a small amount of a suitable base such as a metal carbonate (e.g., potassium carbonate) in a suitable solvent (e.g., DMF, tert-amyl alcohol) at a suitable reaction temperature (e.g., 60 to 120° C.) until the reaction is complete. In preferred methods, purification of CMX212 by column chromatography is not necessary.

In another embodiment, the synthesis of CMX212 results in improved yield relative to other methods known in the art. For example, the synthesis of CMX212 results in a yield of greater than 55%, 60%, 65%, 70%, 75%, 80%, 85% or 90%.

Subsequently, and with reference to Step 2A of Procedure A, the intermediate phosphonic acid, [[(S)-2-(4-amino-2-oxo-1(2H)-pyrimidinyl)-1-(hydroxymethyl)-2-(triphenylmethoxy)ethyl]methyl]mono[3-(hexadecyloxy)propyl]ester (CMX225) is prepared by contacting CMX212 with CMX203 in the presence of a suitable base such as a metal alkoxide (e.g., magnesium di-tert-butoxide, sodium tert-butoxide, lithium tert-butoxide) in a suitable solvent (e.g., DMF, N,N-Dimethylacetamide, dimethylsulfoxide, 1-methyl-2-pyrrolidinone) at a suitable reaction temperature (e.g., 50 to 110° C.) until the reaction is complete. The resultant mixture is subjected to an aqueous extraction (e.g., under acidic condition). CMX225 is then extracted with a suitable organic solvent (e.g., ethyl acetate, isopropyl acetate, dichloromethane). In preferred methods, purification by column chromatography is not necessary. For example, the aqueous extraction step can be used to circumvent purification by column chromatography.

In another embodiment, the alkylation of CMX212 does not result in significant alkylation of the 4-amino group.

In another embodiment, Step 2A of Procedure A results in less than 5% of bis-alkylated CMX212. In another embodiment, Step 2A of Procedure A results in less than 4% of bis-alkylated CMX212. In another embodiment, Step 2A of Procedure A results in less than 3% of bis-alkylated CMX212. In another embodiment, Step 2A of Procedure A results in less than 2% of bis-alkylated CMX212. In another embodiment, Step 2A of Procedure A results in less than 1.5% of bis-alkylated CMX212. In another embodiment, Step 2A of Procedure A results in less than 1.0% of bis-alkylated CMX212. In another embodiment, Step 2A of Procedure A results in less than 0.75% of bis-alkylated CMX212. In another embodiment, Step 2A of Procedure A results in less than 0.5% of bis-alkylated CMX212.

In another embodiment, CMX212 is provided in a purity greater than 90% pure, for example, greater than 92.5% pure, greater than 95% pure, greater than 97.5% pure, or greater than 99% pure.

In another embodiment, CMX212 is provided with no greater than 10% cytosine contamination, for example, no greater than 7.5% cytosine contamination, no greater than 5% cytosine contamination, no greater than 2.5% cytosine contamination, no greater than 1% cytosine contamination.

In another embodiment, CMX203 is provided in a purity greater than 80% pure, for example, greater than 82.5% pure, greater than 85% pure, greater than 87.5% pure, greater than 90.0% pure, greater than 92.5% pure, greater than 95% pure, greater than 97.5% pure, or greater than 99% pure.

In another embodiment, the metal alkoxide is provided in a purity greater than 85%, for example, greater than 87.5% pure, greater than 90.0% pure, greater than 92.5% pure, greater than 95% pure, greater than 97.5% pure, or greater than 99% pure.

In another embodiment, the metal alkoxide is magnesium di-tert-butoxide.

In another embodiment, magnesium di-tert-butoxide is provided in a purity greater than 85%. For example, greater than 87.5% pure, greater than 90.0% pure, greater than 92.5% pure, greater than 95% pure, greater than 97.5% pure, or greater than 99% pure.

In another embodiment, the metal alkoxide is magnesium di-tert-butoxide and the conversion rate of CMX212 and CMX203 to CMX225 is greater than 80%, 85%, 90%, or 95%.

In another embodiment, the suitable temperature for Step 2A of Procedure A is about 80° C. and the reaction completes in about 4 hours.

In another embodiment, the aqueous solution used for the aqueous extraction is aqueous HCl.

In another embodiment, the suitable organic solvent to extract CMX225 is isopropyl acetate.

In another embodiment, vacuum distillation is employed following the aqueous extraction step.

In another embodiment, the solvent (e.g., isopropyl acetate or DMF) is switched to methanol.

Subsequently, and with reference to Step 2B of Procedure A, phosphonic acid, [[(S)-2-(4-amino-2-oxo-1(2H)-pyrimidinyl)-1-(hydroxymethyl)ethoxy]methyl]mono[3-(hexadecyloxy)propyl]ester (CMX001) is prepared by contacting CMX225 with a suitable deprotecting agent (e.g., hydrogen chloride, acetyl chloride) in a suitable solvent (e.g., methanol) until the reaction is complete. CMX001 is recrystallized using a suitable solvent system (e.g., methanol:acetone:water, ethanol, methanol).

In another embodiment, the deprotection of CMX225 is completed with hydrogen chloride gas.

In another embodiment, the temperature of the deprotection reaction is kept at between 0 and 20° C., e.g., between 5 and 15° C.

In another embodiment, Step 2B of Procedure A is quenched with water and the pH is adjusted to about 2.3-2.7, e.g., about 2.5.

In another embodiment, the recrystallization of CMX001 with a suitable solvent system produces material with a purity of greater than 91% (e.g., >92%, >93%, >94%, >95%, >97.5%, >98%, >99%, or >99.5%)

In another embodiment, the recrystallization of CMX001 with a suitable solvent system produces Form A. Preferably, Form A has a purity of greater than 91% (e.g., >92%, >93%, >94%, >95%, >97.5%, >98%, >99%, or >99.5%).

In one embodiment, Form A is not a hydrate.

In other embodiments, Form A is a solvate, e.g., a methanol solvate, an ethanol solvate, or an isopropanol solvate.

In another embodiment, Form A is a non-stoichiometric solvate, e.g., a methanol solvate, an ethanol solvate, or an isopropanol solvate.

In another embodiment, Form A is a desolvated solvate, e.g., a desolvated methanol solvate, a desolvated ethanol solvate, or a desolvated isopropanol solvate.

In another embodiment, the recrystallization of CMX001 with a suitable solvent system produces material with a purity >99% purity by HPLC AUC (area under curve).

In another embodiment, no column chromatography is used in the synthesis of CMX001.

In another embodiment, CMX001 is isolated as the free acid.

In another embodiment, CMX001 is recrystallized from methanol.

In another embodiment, CMX001 is recrystallized and isolated from methanol at a temperature no lower than 20° C.

In another embodiment, Steps 2A and 2B of Procedure A result in less than 5% of $N^4$-alkylated CMX001. In another embodiment, Steps 2A and 2B of Procedure A result in less than 4% of $N^4$-alkylated CMX001. In another embodiment, Steps 2A and 2B of Procedure A result in less than 3% of $N^4$-alkylated CMX001. In another embodiment, Steps 2A and 2B of Procedure A result in less than 2% of $N^4$-alkylated CMX001. In another embodiment, Steps 2A and 2B of Procedure A result in less than 1.5% of $N^4$-alkylated CMX001. In another embodiment, Steps 2A and 2B of Procedure A result in less than 1.0% of $N^4$-alkylated CMX001. In another embodiment, Steps 2A and 2B of Procedure A result in less than 0.75% of $N^4$-alkylated CMX001. In another embodiment, Steps 2A and 2B of Procedure A result in less than 0.5% of $N^4$-alkylated CMX001. In another embodiment, Steps 2A and 2B of Procedure A result in less than 0.4% of $N^4$-alkylated CMX001. In another embodiment, Steps 2A and 2B of Procedure A result in less than 0.3% of $N^4$-alkylated CMX001.

In another embodiment, another metal alkoxide (e.g., potassium t-butoxide) is used in Step 2A instead of magnesium t-butoxide and the level of $N^4$-alkylated CMX001 is significantly higher (e.g., at least five times higher) than using magnesium t-butoxide.

Procedure B: Synthesis of Phosphonic Acid,
P-[[[(4-methylphenyl)sulfonyl]oxy]methyl]-,
mono[3-(hexadecyloxy)propyl]ester, Sodium Salt
(CMX203)

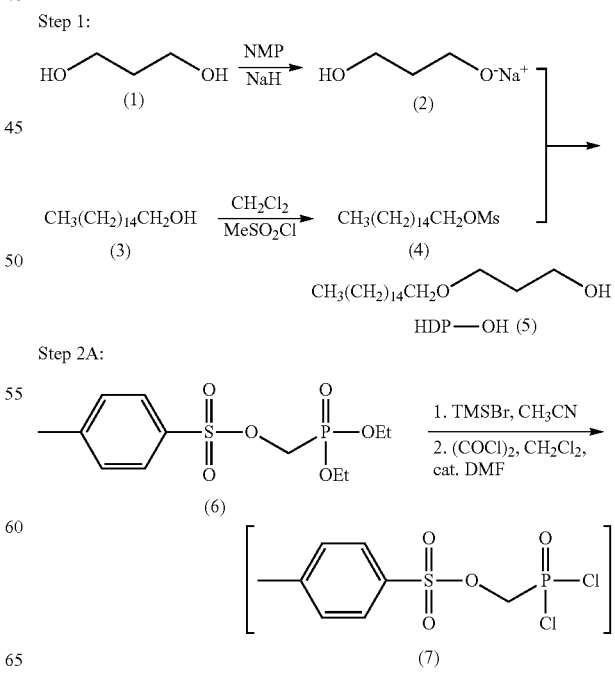

Step 2B:

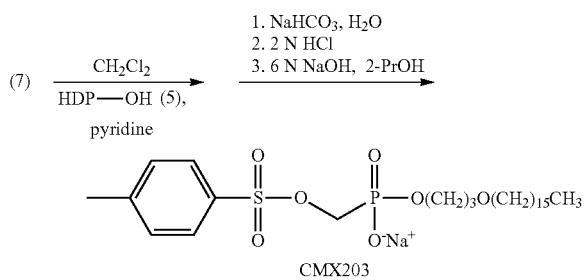

CMX203

Step 1: Synthesis of 3-(hexadecyloxy)propan-1-ol (5)

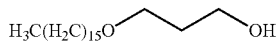

Hexadecyl methanesulfonate (4) is prepared by contacting 1-hexadecanol (3) with methanesulfonyl chloride in the presence of a suitable base such as an amine (e.g., diisopropylethylamine) in a suitable solvent (e.g., dichloromethane) at a suitable reaction temperature (e.g., temperatures less than room temperature to 30° C.) until completion of reaction, typically 0.5 to four hours, for example one to two hours. 3-(hexadecyloxy)propan-1-ol (5) is prepared by contacting 1,3-propandiol (1) with (4) in the presence of a suitable base such as a metal hydride (e.g., sodium hydride) in a suitable solvent (e.g., N-methyl pyrrolidinone (NMP)) at a suitable reaction temperature (e.g., ambient to elevated temperatures) until completion of reaction, typically 12 to 28 hours.

Steps 2A and 2B: Synthesis of Phosphonic acid, P-[[[(4-methylphenyl)sulfonyl]oxy]methyl]-, mono[3-(hexadecyloxy)propyl]ester, Sodium Salt (CMX203)

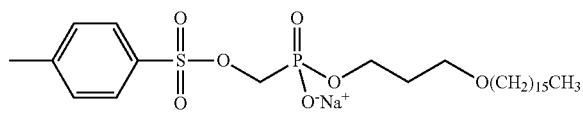

CMX203 is prepared by contacting diethyl (tosyloxy)methylphosphonate (6) with bromotrimethylsilane in a suitable solvent (e.g., acetonitrile) at a suitable reaction temperature (e.g., ambient to elevated temperatures) until completion of reaction, typically one to four hours, for example one to two hours. The resulting mixture is contacted with a halogenating agent (e.g., oxalyl chloride) in a suitable solvent (e.g., dichloromethane) in the presence of a suitable catalyst (e.g., N,N-dimethylformamide) at a suitable temperature (e.g., ambient temperature) until completion of reaction, typically 8 to 20 hours, for example 12 to 16 hours. The resulting (dichlorophosphoryl)methyl 4-methylbenzenesulfonate (7) is contacted with (hexadecyloxy)propan-1-ol (5) in a suitable solvent (e.g., dichloromethane) until reaction is complete. Diethyl (tosyloxy)methylphosphonate is commercially available from Lacamas Laboratories (Portland, Oreg.).

Another preferred embodiment of the invention is depicted in Procedure B. The procedure describes an improved method for preparing phosphonic acid, P-[[[(4-methylphenyl)sulfonyl]oxy]methyl]-, mono[3-(hexadecyloxy)propyl]ester, sodium salt (CMX203). Steps 1, 2A and 2B are described herein.

With reference to Step 1 of Procedure B, 3-(hexadecyloxy)propan-1-ol (5) is prepared by contacting 1,3-propanediol (1) with hexadecyl methanesulfonate (4) in the presence of a suitable base such as a metal hydride (e.g., sodium hydride) in a suitable solvent (e.g., NMP) at a suitable reaction temperature (e.g., ambient to elevated temperature) until the reaction is complete.

In another embodiment, 3-(hexadecyloxy)propan-1-ol (5) is recrystallized from acetonitrile.

In another embodiment, hexadecanol (3) is provided in high purity. For example, hexadecanol (3) is greater than 95% pure, greater than 96% pure, greater than 97% pure, greater than 98% pure, greater than 99% pure, or greater than 99.5% pure.

In another embodiment, NMP is provided in high purity. Specifically, the NMP does not include a butyrolactone chemical impurity. For example, the NMP is greater than 95% pure, greater than 96% pure, greater than 97% pure, greater than 98% pure, greater than 99% pure, or greater than 99.5% pure.

Subsequently, and with reference to Step 2A of Procedure B, the intermediate (dichlorophosphoryl)methyl 4-methylbenzenesulfonate (7) is prepared by contacting diethyl (tosyloxy)methylphosphonate (6) with bromotrimethylsilane in a suitable solvent (e.g., acetonitrile) at a suitable reaction temperature (e.g., ambient to elevated temperature) until the reaction is complete. The resulting mixture is contacting with a halogenating agent (e.g., oxalyl chloride) in a suitable solvent (e.g., dichloromethane) in the presence of a suitable catalyst (e.g., N,N-dimethylformamide) at a suitable temperature (e.g., ambient temperature) until the reaction is complete.

Subsequently, and with reference to Step 2B of Procedure B, CMX203 is prepared by contacting 7 with 5 in a suitable solvent (e.g., dichloromethane) with the addition of pyridine at a suitable temperature (e.g., −5 to 5° C.) until the reaction is complete. The resulting mixture is quenched with an appropriate solvent (e.g., water). Prior to separation, saturated sodium bicarbonate solution is added and the pH is adjusted to 2.0 with an acid (e.g., hydrochloric acid) and CMX203 free acid is formed. The organic layer is then separated, concentrated and then dissolved in an appropriate solvent (e.g., 2-propanol) and sodium hydroxide is added to convert the free acid to CMX203. CMX203 is collected as a precipitate. In preferred methods, purification by column chromatography is not necessary. For example, the organic layer separated after adjusting the pH does not require purification by column chromatography.

In another embodiment, Step 2B of Procedure B comprises: quenching the reaction with a quenching agent (e.g., sodium bicarbonate); and adjusting the pH to 2 with an acid (e.g., hydrochloric acid) before separation of the CMX203 free acid containing-layer.

In another embodiment, Step 2B of Procedure B comprises the use of dichloromethane as a solvent rather than another solvent (e.g., diethyl ether).

During the synthesis of CMX203, tosyloxymethylphosphonic acid ("CMX247"), a by-product, is formed and removed via recrystallization from 2-propanol or one of the solvent systems described in Example 5.

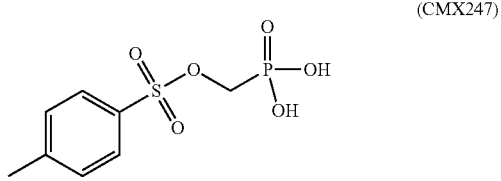 [SMILES: Cc1ccc(S(=O)(=O)OCP(=O)(O)O)cc1]

(CMX247)

In another embodiment, CMX203 is recrystallized from 2-propanol. In another embodiment, CMX203 is recrystallized from a solvent system described in Example 5.

In another embodiment, the recrystallization of CMX203 with a suitable solvent system produces material with ≥99% purity.

In another embodiment, the recrystallization of CMX203 with a suitable solvent system produces material with ≤1% CMX247, e.g., ≤0.5%, ≤0.25%, ≤0.1%, or ≤0.01%.

In another embodiment, the invention provides compositions (e.g., oral dosage forms) with desirable pharmacokinetic characteristics. The compositions further provide for metabolism of the compound of formula (I) having a purity of greater than 91% or being in Form A such that blood levels of the metabolite (i.e., cidofovir) remain below the level at which nephrotoxicity occurs.

The present invention provides, compounds with high purity or in specific morphic form (e.g., Form A), compositions described herein and methods for the treatment or prevention of one or more viral infections in a subject, e.g., an immunodeficient subject. Immunodeficient subjects include organ transplant recipients, patients undergoing hemodialysis, patients with cancer, patients receiving immunosuppressive drugs, and HIV-infected patients. The present invention contemplates the therapeutic and/or prophylactic treatment of immunodeficient subjects as well as subjects that are at risk of becoming immunodeficient but do not yet exhibit symptoms of being immunodeficient. Examples of subjects at risk of becoming immunodeficient include, without limitation, subjects taking immunosuppressive drugs or chemotherapeutic drugs, subjects having cancer, and subjects infected with HIV.

Pharmaceutical Compositions

The present invention also provides pharmaceutical compositions comprising a compound of formulae I or II in combination with at least one pharmaceutically acceptable excipient or carrier.

A "pharmaceutical composition" is a formulation containing a compound of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient or carrier" means an excipient or carrier that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is viral infection.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Dosages can range from about 0.01 mg/kg to about 100 mg/kg. In preferred aspects, dosages can range from about 0.1 mg/kg to about 10 mg/kg. In an aspect, the dose will be in the range of about 1 mg to about 1 g; about 10 mg to about 500 mg; about 20 mg to about 400 mg; about 40 mg to about 400 mg; or about 50 mg to about 400 mg, in single, divided, or continuous doses (which dose may be adjusted for the patient's weight in kg, body surface area in m², and age in years). In certain embodiments, the amount per dosage form can be about 0.1 mg to about 1000 mg, e.g., about 0.1, 0.5, 1, 2, 3, 4, 5, 6, 7, 8, 9, 10, 15, 20, 25, 30, 35, 40, 45, 50, 55, 60, 65, 70, 75, 80, 85, 90, 95 or 100 mg or more. In one embodiment, the amount can be about 20 mg. In one embodiment, the amount can be about 50 mg.

In another embodiment, the invention provides compositions (e.g., pharmaceutical compositions) with desirable pharmacokinetic characteristics. For example, the compositions of the invention may provide a blood level of the compound of formula (I) which, after metabolism to the therapeutically-active form (i.e., cidofovir), results in blood levels of the metabolite that do not induce toxicity (e.g., nephrotoxicity).

An effective amount of a pharmaceutical agent is that which provides an objectively identifiable improvement as noted by the clinician or other qualified observer. As used herein, the term "dosage effective manner" refers to amount of an active compound to produce the desired biological effect in a subject or cell.

In another embodiment, CMX001 or another composition of the present invention can be administered to a subject as a single dose. In another embodiment, CMX001 or another composition of the present invention can be administered to a subject in multiple doses. Multiple doses can be administered regularly, for example, once every 12 hours, once a day, every 2 days, every 3 days, every 4 days, every 5 days, every 6 days, every 7 days, every 8 days, every 9 days, every 10 days, every 11 days, every 12 days, every 13 days, every 14 days or every 15 days. For example, doses can be administered twice per week. Moreover, each individual dose can be administered with the same or a different dosage.

For example, a subject can be administered with a first dose of 2 mg/kg followed by one or more additional doses at 2 mg/kg. For example, a subject can be administered with a first dose of 2 mg/kg followed by one or more additional doses at 1 mg/kg. For example, a subject can be administered with a first dose of 2 mg/kg followed by one or more additional doses at 3 mg/kg. For example, a subject can be administered with a first dose of 4 mg/kg followed by one or more additional doses at 4 mg/kg.

Multiple doses can also be administered at variable time intervals. For example, the first 2, 3, 4, 5, 6, 7, or 8 or more doses can be administered at an interval of 6 days followed by additional doses administered at an interval of 7 days. For example, the first 2, 3, 4, 5, 6, 7, or 8 or more doses can be administered at an interval of 7 days followed by additional doses administered at an interval of 3 days.

In another embodiment, the invention provides an oral dosage form comprising a compound of formula (I) having a purity of greater than 91% or being in Form A for the therapeutic and/or prophylactic treatment of viral infection in a subject, wherein said oral dosage form, upon administration to a human at a dosage of 2 mg/kg of said compound, provides an $AUC_{0-inf}$ of said compound of about 2000 to about 4000 h*ng/mL, e.g., about 2500 to about 3000 h*ng/mL. In some embodiments, the $AUC_{0-inf}$ of said compound is about 2000, 2100, 2200, 2300, 2400, 2500, 2600, 2700, 2800, 2900, 3000, 3100, 3200, 3300, 3400, 3500, 3600, 3700, 3800, 3900, or 4000 h*ng/mL or any range therein. $AUC_{0-inf}$ can be determined by any of the well known methods in the art and as described in the examples herein.

In another embodiment, the invention provides an oral dosage form comprising a compound of formula (I) having a purity of greater than 91% or being in Form A for the therapeutic and/or prophylactic treatment of viral infection in a subject, wherein said oral dosage form, upon administration to a human at a dosage of 2 mg/kg of said compound, provides a $C_{max}$ of said compound of about 100 to about 500 ng/mL, e.g., about 200 to about 400 ng/mL. In some embodiments, the $C_{max}$ of the compound is about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 ng/mL or any range therein. $C_{max}$ can be determined by any of the well known methods in the art and as described in the examples herein.

In another embodiment, the invention provides an oral dosage form comprising a compound of formula (I) having a purity of greater than 91% or being in Form A for the therapeutic and/or prophylactic treatment of viral infection in a subject, wherein said oral dosage form, upon administration to a human at a dosage of 2 mg/kg of said compound of formula (I) and metabolism of said compound of formula (I) to cidofovir, provides a $C_{max}$ of said cidofovir that is less than about 30% of the $C_{max}$ of said compound of formula (I), e.g., less that about 20% of the $C_{max}$ of said compound of formula (I). In some embodiments, the $C_{max}$ of the metabolite (i.e., cidofovir) is less than about 50%, 45%, 40%, 35%, 30%, 25%, 20%, 15%, or 10% of the $C_{max}$ of the compound of formula (I).

In another embodiment, the invention provides an oral dosage form comprising a compound of formula (I) having a purity of greater than 91% or being in Form A, wherein upon administration to a human at a dosage of 2 mg/kg of said compound of formula (I), provides an $AUC_{0-inf}$ of cidofovir of about 1000 to about 5000 h*ng/mL, e.g., about 1500 to about 4000 h*ng/mL. In some embodiments, the $AUC_{0-inf}$ of cidofovir is about 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, or 5000 h*ng/mL or any range therein.

In another embodiment, the invention provides an oral dosage form comprising a compound of formula (I) having a purity of greater than 91% or being in Form A, wherein upon administration to a human at a dosage of 2 mg/kg of said compound of formula (I), provides a $C_{max}$ of cidofovir of about 10 to about 100 ng/mL, e.g., about 20 to about 70 ng/mL. In some embodiments, the $C_{max}$ of the compound of formula (I) is about 10, 20, 30, 40, 50, 60, 70, 80, 90, or 100 ng/mL or any range therein.

In certain embodiments, the oral dosage form provides more than one of the pharmacokinetic characteristics described above, e.g., the $AUC_{0-inf}$ or $C_{max}$ of the compound of formula (I) or the metabolite (i.e., cidofovir) or the $C_{max}$ ratio of the metabolite (i.e., cidofovir) to the compound of formula (I), e.g., 2, 3, 4, or more of the pharmacokinetic characteristics in any combination.

The pharmacokinetic behavior of a composition will vary somewhat from subject to subject within a population. The numbers described above for the compositions of the invention are based on the average behavior in a population. The present invention is intended to encompass compositions that on average fall within the disclosed ranges, even though it is understood that certain subjects may fall outside of the ranges.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, diethylamine, diethylaminoethanol, ethylenediamine, imidazole, lysine, arginine, morpholine, 2-hydroxyethylmorpholine, dibenzylethylenediamine, trimethylamine, piperidine, pyrrolidine, benzylamine, tetramethylammonium hydroxide and the like.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p 1-92, Elesevier, N.Y.-Oxford (1985).

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the invention can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

It will be appreciated that the methods disclosed herein are suitable for both large-scale and small-scale preparations of the desired compounds. In preferred embodiments of the methods described herein, the phosphonate esters may be prepared on a large scale, for example on an industrial production scale rather than on an experimental/laboratory scale. For example, a batch-type process according to the methods of the disclosure allows the preparation of batches of at least 1 g, or at least 5 g, or at least 10 g, or at least 100 g, or at least 1 kg, or at least 100 kg of phosphonate ester product. Furthermore, the methods allow the preparation of a phosphonate ester product having a purity of at least 98%, or at least 98.5% as measured by HPLC. In preferred embodiments according to the disclosure, these products are obtained in a reaction sequence that does not involve purification by any form of chromatography (e.g., gas chromatography, HPLC, preparative LC, size exclusion chromatography, and the like).

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

It is to be understood that while the invention has been described in conjunction with the preferred specific embodiments thereof, that the foregoing description as well as the examples that follow, are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

EXAMPLES

Unless otherwise specified, the analytical instruments and parameters used for compounds described in the Examples are as follows:

NMR data were acquired on Jeol 300, model JNM-ECP300. Sample was. NMR samples of CMX212 were prepared in D6-DMSO (~10 mg/ml). NMR samples of CMX001 were D3-MeOD solutions saturated with CMX001.

The XRD data were collected on a Rigaku Ultima IV with Cu Kα radiation (40 kV, 44 mA) from 2 to 50 degrees 2-theta at a scanning rate of 2 degrees/min and sampling width of 0.020 degrees. The powder samples were spread on standard sample holders (glass slide). A sample spinner was used during analysis (60 rpm).

The HPLC instrument used was an Agilent 1100 Series. Analytical Details are as follows:
Reagents and Materials
  Water (H2O), chromatographic quality
  Methanol (MeOH), chromatographic quality
  Ammonium Acetate, ACS Grade
  Disodium ethylenediamine tetraacetate (EDTA), ACS Grade
  Cytosine Reference Standard
  ACC-338.1 (CMX212) Reference Standard
  Bis-trityl impurity standard
  Syringe fitted with a 0.45 µm syringe filter Column: Phenomenex Synergi Polar-RP, 150 mm×3 mm, 4 µm particle size.
Mobile Phase Preparation
  50 mM Buffer Solution:
    Combine 3.85 g of ammonium acetate and 18.6 mg of disodium EDTA with 1000 mL of water, and mix to dissolve the solids. Filter through a 0.45 µm filter.
  Mobile Phase A: (35/65) 50 mM Buffer Solution/Methanol
  Combine 350 mL 50 mM Buffer Solution and 650 mL Methanol. Mix well and sonicate for 5 minutes to degas.
  Mobile Phase B: 100% Methanol
Operating Parameters
  Detection: UV at 274 nm or 225 nm
  Injection Volume: 5 µL,
  Column Temperature: 30° C.
  Flow Rate: 0.8 mL/min
  Gradient:

| Time (min) | Mobile Phase B (%) |
|---|---|
| 0 | 0 |
| 12 | 40 |
| 18 | 85 |
| 22 | 100 |
| 30 | 100 |
| 30.01 | 0 |
| 35 | 0 |

Run Time: 35 minutes
Approximate Retention Times:

| Compound | RT(min) | RRT* |
|---|---|---|
| Cytosine | 1.0 | 0.2 |
| CMX212 | 6.5 | 1.0 |
| bis-trityl impurity | 20.3 | 3.3 |

*RRT = (Retention Time of the bis-trityl impurity)/(Retention Time of CMX-212)

Example 1

Preparation of (S)-N$^1$-[(2-hydroxy-3-triphenyl-methoxy)propyl]cytosine (CMX212)

Under an inert atmosphere, e.g., nitrogen, at ambient temperature a reactor was charged with (S)-trityl glycidyl ether (40.0 kg, 126.4 mol), cytosine (12.8 kg, 115.2 mol), potassium carbonate (1.7 kg, 12.3 mol), and anhydrous N,N-dimethylformamide (51.2 kg) and were heated at 85-95° C. for 9 hours. The reaction mixture was cooled to 60-70° C. and quenched with toluene (150.4 kg). The resulting slurry was cooled to −5 to 0° C. filtered, washed with toluene (25.6 kg), and then washed with acetone (3×25.7 kg). The filter cake was suspended in acetone (128.0 kg) and heated at approximately 56° C. for 30 minutes then cooled to below 0° C. and filtered. The cake was washed with acetone (25.6 kg) and dried in vacuo at 45° C. to constant weight yielding 32.4 kg (65.8%) of CMX212 as a white to off white solid. Typical HPLC (AUC) purity was >99% at the wavelength of 274 nm and was >98% at the wavelength of 225 nm. $^1$H-NMR was consistent with structure. Melting point=215° C. (decomposition).

TABLE 1

Summary of Reaction Parameters for CMX212

| Reagent | Range | Optimal |
|---|---|---|
| Cytosine | 1.0 Mol equiv. | 1.0 Mol equiv. |
| (S)-trityl glycidyl ether | 1.0-1.3 Mol equiv. | 1.1 Mol equiv. |
| Potassium carbonate | 0.1-1.0 Mol equiv. | 0.1 Mol equiv. |
| DMF | 4.56-7.56 Mol ratio | 6.08 Mol ratio |
| Toluene | 8 to 18% w/w | 12% w/w |
| Reaction time | 4 to 24 hours | 9 hours |
| Reaction temperature | 20-120° C. | 90° C. |
| Isolation temperature | −5 to 20° C. | −5° C. |

Example 2

Preparation of phosphonic acid, [[(S)-2-(4-amino-2-oxo-1(2H)-pyrimidinyl)-1-(hydroxymethyl)ethoxy]methyl]mono[3-(hexadecyloxy)propyl]ester (CMX001)

Figure 9:
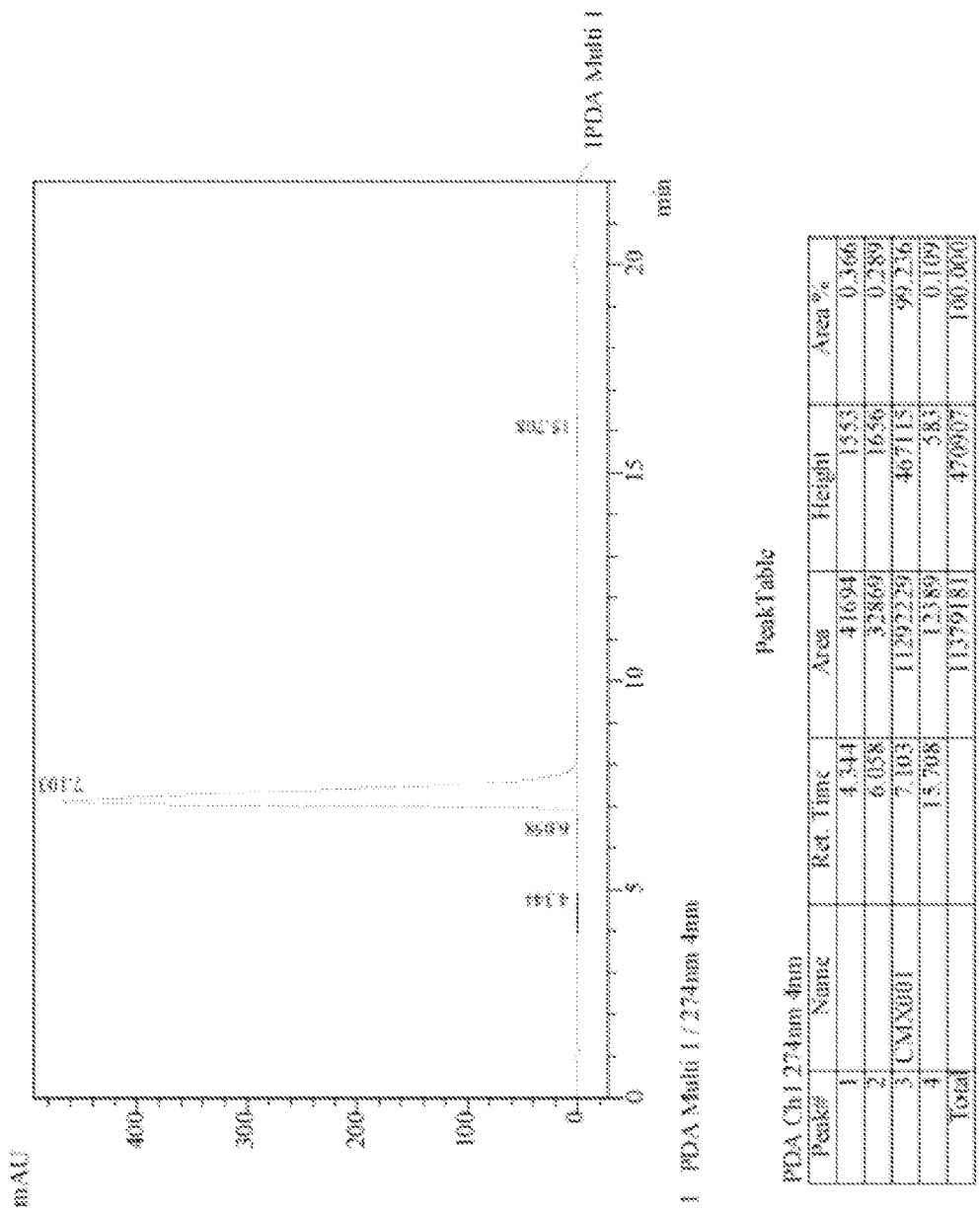
FIG. 9 is an HPLC chromatogram of Form A (Lot#5).

Under an inert atmosphere, e.g., nitrogen, at ambient temperature a reactor was charged with CMX212 (14.5 kg, 33.9 mol), CMX203 (21.2 kg, 37.2 mol), magnesium di-tert-butoxide (6.1 kg, 35.7 mol), and N,N-dimethylformamide (44.9 kg). The reaction mixture was heated at 77 to 83° C. for three to four hours. The reaction mixture was concentrated via distillation until approximately one-half of the N,N-dimethylformamide was removed. The concentrate was diluted with isopropyl acetate (120.1 kg) and the combined organics are washed sequentially with 0.5M HCl (approximately 40 gal.) and brine (40 gal.). The organic phase was distilled to remove the isopropyl acetate. The concentrate was diluted with methanol (87.0 kg) and re-concentrated to remove residual isopropyl acetate. Typical HPLC (AUC) purity of the crude CMX225 was >92% at the wavelength of 225 nm and was >94% at the wavelength of 274 nm. The concentrate containing crude CMX225 was diluted with methanol (76.8 kg) and hydrogen chloride gas (3.8 kg) and was charged to the reactor below the solvent level. (It was important to control the HCl gas addition rate to keep the reaction temperature between 5 and 15° C.) Once the HCl addition was complete, the reaction was maintained at below 18° C. for 2 hours then filtered to remove insoluble material. The filtrate was diluted with water (30.5 gal.) and the mixture was pH adjusted to 2.3-2.7 with 1.0N sodium hydroxide. The solids were filtered and washed sequentially with water (11.1 gal.) and acetone (2×29.0 kg). The filter cake was slurried in acetone (101.5 kg) at approximately 40° C. for 1 hour then filtered and washed with acetone (2×29.0 kg). Typical HPLC (AUC) purity of the crude CMX001 was >97% at the wavelength of 274 nm and was >76% at the wavelength of 225 nm. The crude product was heated at 70° C. in methanol (101.5 kg) to afford a homogenous solution, cooled to 15-25° C. for 2 hours, filtered, and washed with methanol (29.2 kg). Typical HPLC (AUC) purity was >98% after the first recrystallization. The product was recrystallized a second time from methanol (75.9 kg), filtered, washed with methanol (29.0 kg), and dried in vacuo at 50° C. to constant weight to yield 14.8 kg (77.7%) of CMX001 as a white to off white solid. Typical HPLC (AUC) purity was >99% (see FIG. 9). $^1$H-NMR was consistent with structure (see FIGS. 8(a)-(d)).

TABLE 2

Summary of Reaction Parameters for CMX225

| Reagent | Range | Optimal |
|---|---|---|
| CMX212 | 1.0-3.0 Mol equiv. | 1.0 Mol equiv. |
| Magnesium di-tert-butoxide | 0.75-3.0 Mol equiv. | 1.05 Mol equiv. |
| CMX203 | 0.33-1.3 Mol equiv. | 1.1 Mol equiv. |
| DMF | 2.0-6.25% w/w | 3.1% w/w |
| Reaction time | 0.25 to 24 hours | 3 hours |
| Reaction temperature | 50-120° C. | 80° C. |
| Isopropyl acetate | 6-10.5% w/w | 10.0% w/w |
| 0.5M HCl | 9.5-10.5% w/w | 10.0% w/w |

Additional bases used that produced CMX225 include: sodium tert-butoxide, lithium tert-butoxide, potassium tert-butoxide, sodium hydride, sodium methoxide, and sodium tert-amyl alkoxide.

Additional solvents used that produced CMX225 include: DMSO, HMPA, DMA, and NMP.

TABLE 3

Summary of Reaction Parameters for CMX001

| Reagent | Range | Optimal |
|---|---|---|
| CMX225 | 1.0 Mol equiv. | 1.0 Mol equiv. |
| Hydrogen chloride | 1.0-10.0 Mol equiv. | 3.0 Mol equiv. |
| Methanol (recrystallization) | 6.0-10.0% w/w | 7.0% w/w |
| Reaction time | 1 to 72 hours | 2 hours |
| Reaction temperature | 10-40° C. | 15° C. |
| Water quench | 7.75-15% w/w | 8.0% w/w |
| Isolation temperature | 0-25° C. | 20° C. |

Additional acids used for de-tritylation include: acetyl chloride.

Additional solvents used that produced CMX001 include: dichloromethane.

Additional solvents used for recrystallization include: methanol:acetone:water, ethanol, methanol:acetone, methanol:water.

It was observed that when potassium t-butoxide was used in the coupling of CMX212 and CMX203, the level of $N^4$-alkylated (or bis-alkylated) byproduct generated was significantly higher (e.g., at least five times higher) than using magnesium t-butoxide.

Example 3

Preparation of hexadecyl methanesulfonate (4)

Under an inert atmosphere, e.g., nitrogen, a reactor was charged with 1-hexadecanol 3 (3.78 kg), anhydrous dichloromethane (40 L) and diisopropylethylamine (2.21 kg). The reaction mixture was cooled to −5 to 5° C. and methanesulfonyl chloride (1.87 kg) was added at a controlled rate over 2 hours to ensure that the reaction temperature was kept below 5° C. After the addition was complete, the mixture was warmed to 20 to 30° C. and stirred for one to two hours. The reaction was monitored by GC-MS and was deemed complete when the conversion rate was ≥95%. The reaction was maintained at 20 to 30° C. while being diluted with water (15 L). The organic layer was separated, washed with water (0.50 kg), and concentrated to dryness to yield 4 as a light yellow solid (4.87 kg, 96%). Typical HPLC (AUC) purity was >95%. $^1$H-NMR was consistent with structure.

TABLE 4

Summary of Reaction Parameters for 4

| Reagent | Range | Optimal |
|---|---|---|
| 1-hexadecanol | 1.0 Mol equiv. | 1.0 Mol equiv. |
| Methanesulfonyl chloride | 1.0-1.3 Mol equiv. | 1.1 Mol equiv. |
| Diisopropylethylamine[1] | 1.0-1.5 Mol equiv. | 1.05-1.1 Mol equiv. |
| Dichloromethane | 5.0-11.0 vol equiv. | 5.0 vol equiv. |
| Reaction time | 0.5 to 6 hours | 1.5 to 2 hours |
| Reaction temperature | −5 to 30° C. | −5 to 30° C. |
| Water quench | 7.75-15% w/w | 8.0% w/w |
| Isolation temperature | 0-25° C. | 20° C. |

[1] Additional base the produced 4 includes: triethylamine (1.3 Mol equiv.).
[2] Additional solvents used that produced 4 include: toluene and dichloroethane.

Example 4

Preparation of 3-(hexadecyloxy)propan-1-ol (5)

Under an inert atmosphere, e.g., nitrogen, a reactor was charged with 1,3-propanediol (4.07 kg) and NMP (30 L). The reaction was cooled to −5 to 5° C. and kept under a nitrogen atmosphere. Sodium hydride (1.07 kg, 60% in mineral oil) was cautiously added portion-wise. After the addition was complete, the reaction was stirred at room temperature for an additional 2 hours. A solution of hexadecyl methanesulfonate 4 (4.39 kg) dissolved in NMP (10 L) was added slowly to the reaction mixture at 20 to 55° C. The resulting solution was stirred for 12 to 28 hours at 20 to 35° C. The reaction was monitored by GC-MS and was considered complete when the conversion rate was ≥95%. The reaction mixture was cooled down to −5 to 5° C. and slowly diluted with water (15 L). The reaction was extracted with ethyl acetate (2×25 L). The organic phase was washed with water (20 L), dried over Na$_2$SO$_4$ and concentrated to give a brown oil. The crude product was dissolved in methanol (20 L) and aged at 20 to 30° C. for 12 hours. The resulting solid impurities were filtered and discarded and the filtrate was concentrated. Acetonitrile (40 L) was added to the concentrate and the mixture was aged 5 to 15° C. for 16 hours. The solid was filtered and dried at 25 to 30° C. to afford 5 as a white solid (3.1 kg, 77%). Typical HPLC (AUC) purity was >95%. $^1$H-NMR was consistent with structure.

TABLE 5

Summary of Reaction Parameters for 5

| Reagent | Range | Optimal |
|---|---|---|
| 1,3-propanediol | 3.9-4.0 Mol equiv. | 3.9 Mol equiv. |
| Sodium hydride (60% in mineral oil) | 1.95-2.0 Mol equiv. | 1.95 Mol equiv. |
| NMP[3] | 3.0-14.0 vol equiv. | 7.4 vol equiv. |
| Hexadecyl methanesulfonate (4) | 1.0 Mol equiv. | 1.0 Mol equiv. |
| Reaction time | 12 to 48 hours | 12 to 28 hours |
| Reaction temperature | −10 to 55° C. | −10 to 55° C. |

[3]Additional solvents used that produced 5 include: 2-methyl tetrahydrofuran, N,N-dimethylformamide, and toluene. Additional solvents used to recrystallize 5 include: ethyl acetate: acetonitrile (1:2 v/v).

Example 5

Preparation of Phosphonic acid, P-[[[(4-methylphenyl)sulfonyl]oxy]methyl]-, mono[3-(hexadecyloxy)propyl]ester, Sodium Salt (CMX203)

Under an inert atmosphere, e.g., nitrogen, a reactor was charged with diethyl (tosyloxy)methyloxyphosphonate (6, 4.00 kg) and anhydrous acetonitrile (36 L). Bromotrimethylsilane (6.65 kg) was cautiously added to the reaction. Once the addition was complete, the reaction was stirred at 20 to 30° C. for 1 hour and then heated to 55° C. and stirred for an additional two hours. The mixture was cooled to 20 to 30° C. and concentrated in vacuo. The concentrate was dissolved in anhydrous dichloromethane (36 L) and oxalyl chloride (5.52 kg) was added slowly over two hours. Excessive gas evolution was observed from the reaction. The reaction was stirred for two hours and N,N-dimethylformamide (DMF) (2.0 mL) was added. After the DMF addition, the reaction was stirred for 12 to 16 hours. The reaction mixture was concentrated to give (dichlorophosphoryl)methyl 4-methylbenzenesulfonate (7) as a brown oil. 7 was dissolved in anhydrous dichloromethane (36 L) and 3-(hexadecyloxy)propan-1-ol (5) (3.25 kg) was added. The reaction was cooled to −5 to 5° C. and pyridine (2.56 kg) was added dropwise. After the reaction was complete, the mixture was stirred at 20 to 30° C. for two hours and then quenched by the slow addition of water (5.0 L). The first 500 mL of water was added over 30 minutes due to a strong exotherm. The remainder of the water was added over 15 minutes. A saturated solution of sodium bicarbonate was added over 30 minutes and stirring was continued for one hour. The mixture was pH adjusted to 2.0 with 6N hydrochloric acid. The organic layer was separated and the aqueous phase was extracted with dichloromethane (10 L). The combined organic layers were washed with water (2×10 L), dried over sodium sulfate and concentrated to afford a brown oil. The crude product was dissolved in 2-propanol (50 L) and 6N sodium hydroxide (4.0 mL) was added. The solution was kept at 20 to 30° C. for three days. The precipitate was collected by filtration and washed with 2-propanol (12 L). The filter cake was dried in vacuo to give CMX203 as a white solid (4.50 kg, 73% based on 3-(hexadecyloxy)propan-1-ol (5)).

TABLE 6

Summary of Reaction Parameters for Intermediate 7

| Reagent | Range | Optimal |
|---|---|---|
| Diethyl tosyloxymethyloxyphosphonate (6) | 1.0-1.5 Mol equiv. | 1.15 Mol equiv. |
| Bromo(trimethylsilane) | 2.1-4.0 Mol equiv. | 4.0 Mol equiv. |
| Acetonitrile[4] | 9.0 vol equiv. | 9.0 vol equiv. |
| Dichloromethane | 2.5-11.0 vol equiv. | 4.5-9.0 vol equiv. |
| Oxalyl chloride | 2.1-5.0 Mol equiv. | 4.02 Mol equiv. |
| N,N-Dimethylformamide | 1-2 mL | 1-2 mL |
| Reaction time | 1 to 24 hours | 1 to 24 hours |
| Reaction temperature | 20 to 55° C. | 20 to 55° C. |

[4]Additional solvent used that produced 7 includes: dichloromethane.

TABLE 7

Summary of Reaction Parameters for CMX203

| Reagent | Range | Optimal |
|---|---|---|
| (dichlorophosphoryl)methyl 4-methylbenzenesulfonate (7) | 4.0 Mol equiv. | 4.0 Mol equiv. |
| 3-(hexadecyloxy)propan-1-ol (5) | 1.0 Mol equiv. | 1.0 Mol equiv. |
| Pyridine[5] | 3.0 Mol equiv. | 3.0 Mol equiv. |
| Dichloromethane | 8.0-11.0 vol equiv. | 8.0-11.0 vol equiv. |
| 2-propanol[6] | 15.4 vol equiv. | 15.4 vol equiv. |
| Reaction temperature | −5 to 40° C. | −5 to 40° C. |
| Isolation temperature | 0 to 25° C. | 20 to 25° C. |

[5]Additional base used that produced CMX203 includes: triethylamine (1.5-3.0 Mol equiv.)
[6]Additional recrystallization conditions that afforded CMX203 include:

| Solvent(s) | Ratio | Volume equiv. |
|---|---|---|
| Isopropanol:Ethanol | 1:1 | 5 |
| Ethanol | — | 10 |
| Isopropanol:Methanol | 5:1 | 10 |

TABLE 7-continued

| | | |
|---|---|---|
| Isopropanol:Ethanol | 5:1 | 10 |
| Isopropanol:Tetrahydrofuran | 5:1 | 10 |
| Dichloromethane:Isopropanol | 3:10 | 10 |
| Isopropanol:Toluene | 4:1 | 10 |
| Toluene | — | 10 |
| Dimethylformamide | — | 10 |
| Dichloromethane:Ethanol | 1:1 | 8 |
| Dichloromethane:Acetonitrile | 1:5 | 10 |
| Isopropanol:Water | 1:1 | 10 |
| Acetone:Methanol | 1:1 | 10 |
| Acetone:Isopropanol | 1:1 | 10 |
| Methyl tert-butylether:Methanol | 1:1 | 10 |
| Ethyl acetate:Methanol | 1:1 | 10 |
| Isopropanol:Methanol | 1:1 | 10 |
| Dichloromethane:Methanol | 1:1 | 10 |
| Toluene:Methanol | 1:1 | 10 |

During recrystallization, temperatures ranged from 20-55° C. and recrystallization time ranged from 1-20 hours.

Example 6

Preparation of (S)-$N^1$-[(2-hydroxy-3-triphenyl-methoxy)propyl]cytosine (CMX212)

Under a nitrogen atmosphere at ambient temperature a reactor was charged with cytosine, (S)-trityl glycidyl ether, potassium carbonate, and anhydrous N,N-dimethylformamide. The reaction mixture was heated and maintained at 85 to 95° C. until complete then cooled to 60 to 70° C. The reaction mixture was quenched with water, stirred at ambient temperature and filtered. The wet solids were dried by azeotropic distillation with toluene, cooled to 25±5° C. and filtered. The solids were slurried in acetone at 35±5° C., filtered and dried under vacuum at 50±5° C. until the product contained less than or equal to 0.5% residual solvents. Yield: approximately 36.1 kg to 40.9 kg (84.4 to 95.6 moles) of CMX212; 75 to 85% based on cytosine. Process monitoring: HPLC-Reaction completion, starting material (cytosine) is ≤5% AUC.

TABLE 8

Materials used for Example 6 preparation of CMX212

| Reagent | Amount | Moles |
|---|---|---|
| cytosine | 12.5 kg | 112.5 moles |
| (S)-trityl glycidyl ether | 39.1 kg | 123.6 moles |
| Potassium carbonate | 1.6 kg | 11.8 moles |
| N,N-dimethylformamide | 60.0 kg | — |
| Water | 38.9 Gal | — |
| Toluene | 125.0 L | — |
| Acetone | 150.0 L | — |

Example 7

Preparation of phosphonic acid, [[(S)-2-(4-amino-2-oxo-1(2H)-pyrimidinyl)-1-(hydroxymethyl)ethoxy]methyl]mono[3-(hexadecyloxy)propyl]ester (CMX001)

Under a nitrogen atmosphere at ambient temperature a reactor was charged with CMX212, CMX203, magnesium di-tert-butoxide, and anhydrous N,N-dimethylformamide. The reaction mixture was heated and maintained at 77 to 83° C. until complete. The reaction mixture was concentrated to approximately one-half its original volume then cooled to between 25 and 30° C. Isopropyl acetate was added to the reactor and extracted with 0.5M HCl then a brine solution. The organic phase was vacuum distilled to remove the isopropyl acetate. Methanol was added and the reaction was concentrated to remove any residual isopropyl acetate. The resulting intermediate (CMX225) was dissolved in methanol, cooled and hydrogen chloride gas was charged to the reactor below the surface of the methanol. The reaction was stirred until complete then filtered to remove any insoluble material. The mixture was quenched with water and the pH was adjusted to approximately 2.5 with sodium hydroxide. The resulting solid was filtered, washed with water then acetone. The solids were slurried in acetone at approximately 40° C. and filtered. The crude product was recrystallized from methanol and dried. The product was recrystallized from methanol a second time and dried under vacuum at approximately 50° C. until there was less than or equal to 0.5% residual solvents remaining. Yield: approximately 12.4 kg to 14.3 kg (22.0 to 25.4 moles) of CMX001; 65 to 75% based on CMX212. Process monitoring: HPLC-Step 2A: CMX212 is ≤5% AUC; Step 2B: $N^4$-alkylated by-product (process impurity) is ≤1% AUC.

TABLE 9

Materials used for Example 7 preparation of CMX001

| Reagent | Amount | Moles |
|---|---|---|
| CMX212 | 14.5 kg | 33.9 moles |
| CMX203 | 21.3 kg | 37.3 moles |
| Magnesium di-tert-butoxide | 6.1 kg | 35.6 moles |
| N,N-dimethylformamide | 45.0 kg | — |
| Isopropyl acetate | 145.0 kg | — |
| 0.5M hydrogen chloride solution | 7.3 kg | — |
| Water | 35.8 Gal | — |
| Methanol | 324.0 kg | — |
| Hydrogen chloride gas | 3.8 kg | — |
| Water | 33.9 kg | — |
| Acetone | 160.0 kg | — |

It was also noted that when (S)-$N^1$-[(2,3-dihydroxy)propyl]cytosine was used to couple with CMX203, instead of CMX212, no CMX001 was formed under the same reaction conditions.

Example 8

Preparation Process of Phosphonic Acid, [[(S)-2-(4-amino-2-oxo-1(2H)-pyrimidinyl)-1-(hydroxymethyl)ethoxy]methyl]mono[3-(hexadecyloxy)propyl]ester (CMX001) Described in WO 2005/08788

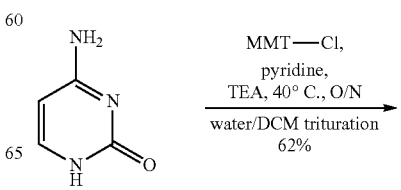

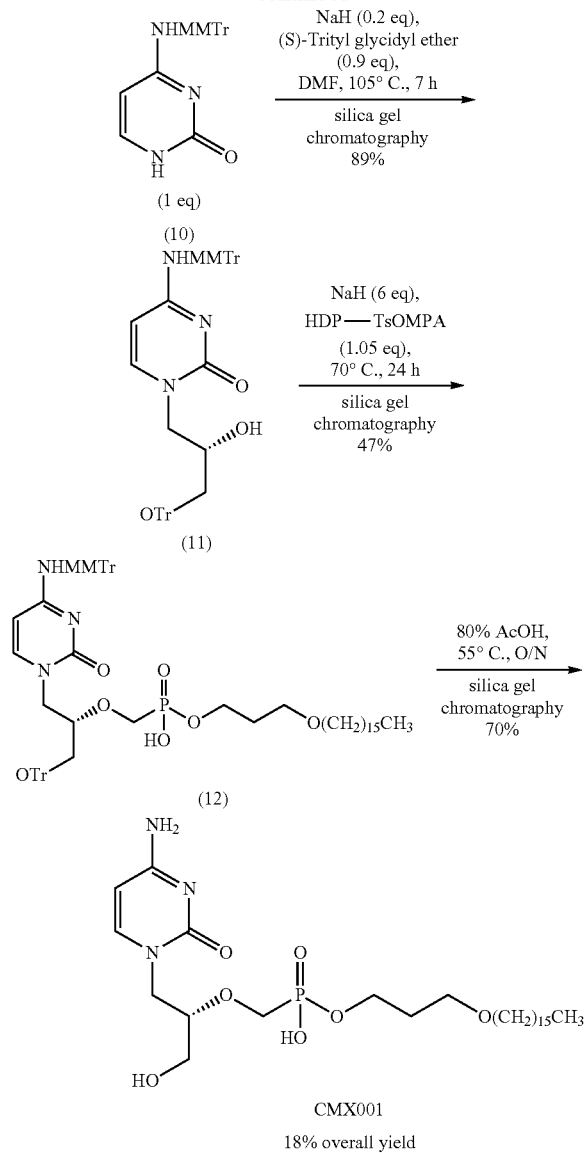

Synthesis of N⁴-monomethoxytrityl-O³'-trityl-dihydroxypropylcytosine (11): N⁴-monomethoxytritylcytosine (10) (3.44 g, 8.9 mmol) and sodium hydride (0.043 g, 1.78 mmol) were stirred in dimethylformamide (DMF) (50 mL) at room temperature for one hour. The reaction mixture was treated with (S)-trityl glycidyl ether (2.5 g, 8.0 mmol) and heated at 105° C. for seven hours. The crude product was dissolved in chloroform and washed with water, concentrated, and purified by column chromatography to afford the desired product in 89% yield.

Synthesis of N⁴-monomethoxytrityl-O³'-trityl-cidofovir, hexadecyloxypropyl ester (12): Sodium hydride (0.14 g, 6.0 mmol) was added to a solution of N⁴-monomethoxytrityl-O³'-trityl-dihydroxypropylcytosine (0.70 g, 1.0 mmol) in DMF (10 mL). Toluenesulfonyloxymethylphosphonate, hexadecyloxypropyl ester (HDP-TsOMPA) (0.82 g, 1.05 mmol) was added to the solution and the mixture was stirred at 70° C. for 24 hours then cooled to room temperature. The mixture was extracted with chloroform and washed with water, dried, concentrated, and purified by column chromatography on silica gel to give the desired product in 47% yield.

Synthesis of Hexadecyloxypropyl-cidofovir (CMX001): N⁴-monomethoxytrityl-O³'-trityl-cidofovir, hexadecyloxypropyl ester (0.38 g, 0.35 mmol) was treated with 80% acetic acid (10 mL) and stirred at 55° C. overnight. The solvent was evaporated and the residue was purified by column chromatography on silica gel (20% methanol in dichloromethane) to afford the desired product in 70% yield. Overall yield of CMX001 was 18%.

Example 9

Preparation Process of Toluenesulfonyloxymethylphosphonate, Hexadecyloxypropyl Ester (HDP-TsOMPA) Described in WO 2005/08788

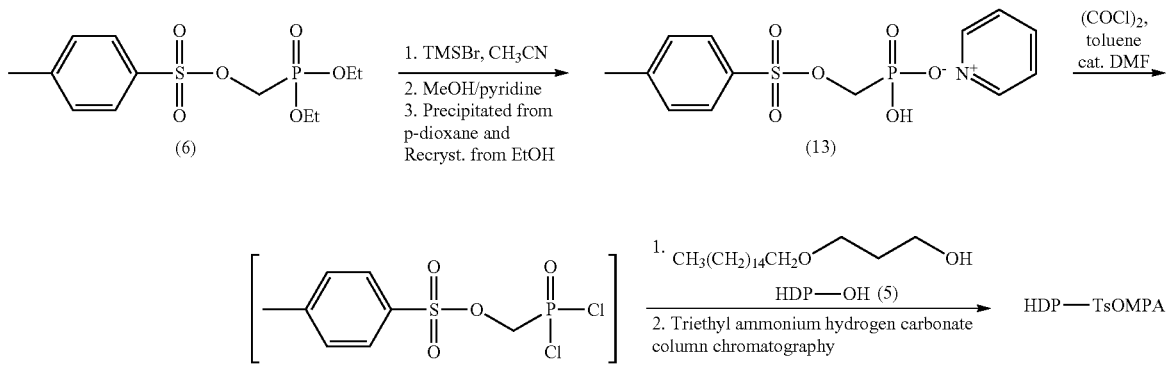

Synthesis of pyridinium toluenesulfonyloxymethylphosphonate (13): Diethyl toluenesulfonyloxymethylphosphonate (6) (1.0 g, 3.1 mmol) was dissolved in dry acetonitrile (25 mL) and the mixture was cooled in an ice bath and stirred magnetically. Bromotrimethylsilane (1.42 g, 9.3 mmol) was added all at once. The mixture was stirred for 4 hours. The solvent was evaporated to leave a thick oil. Methanol/pyridine (30 mL) was added and the mixture was stirred for 30 min. The solvent was evaporated and the residue was combined with p-dioxane and stirred. White crystals were collected and recrystallized from ethanol (EtOH) to yield 750 mg product (73%).

Synthesis of toluenesulfonyloxymethylphosphonate, hexadecyloxypropyl ester (HDP-TsOMPA): To a solution of pyridinium toluenesulfonyloxymethylphosphonate (1.0 g, 3.0 mmol) in dry toluene (20 mL) was added oxalyl chloride (0.39 mL, 4.5 mmol) and DMF (0.02 mL, 0.3 mmol) in one portion. The solution was stirred at room temperature for 1 hour. Toluene and the excess oxalyl chloride were removed under vacuum. The residue was re-dissolved in toluene (10 mL). 3-Hexadecyloxy-1-propanol (5) (0.81 mL, 2.7 mmol) was added. The mixture was stirred at room temperature overnight. Triethyl ammonium hydrogen carbonate buffer (10 mL) was added to the mixture which was stirred form 30 min. Solvents were evaporated. The residue was dissolved in chloroform (50 mL), washed with water (2×10 mL) and the solvent evaporated to give 1 gram of crude product. The impurities were removed by flash column chromatography (silica gel, 15% EtOH/dichloromethane) Yield=0.60 g (40%).

It is unclear from the description of WO 2005/08788 whether the HDP-TsOMPA was a triethyl ammonium salt, a sodium salt, a free acid, or a mixture thereof.

Example 10

Preparation of Phosphonic Acid, [[(S)-2-(4-amino-2-oxo-1(2H)-pyrimidinyl)-1-(hydroxymethyl)ethoxy]methyl]mono[3-(hexadecyloxy)propyl]ester (CMX001) using Cyclic Cidofovir as Described in U.S. Pat. No. 6,716,825

Step 1

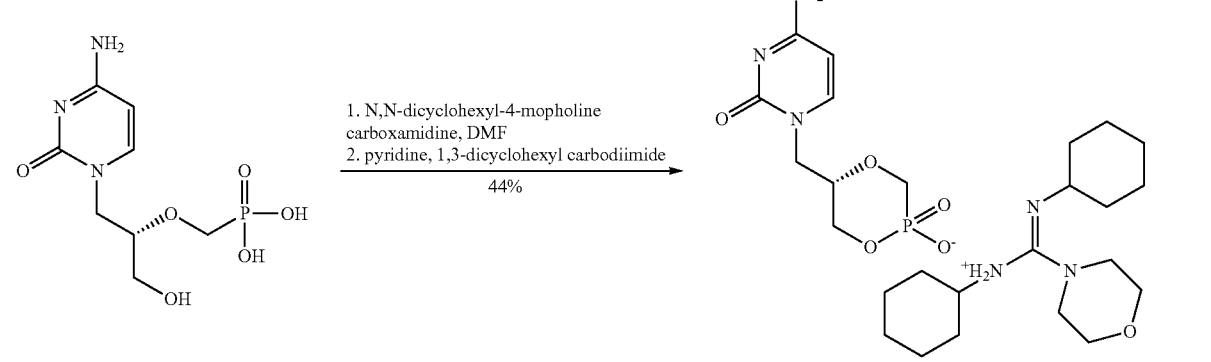

Step 2

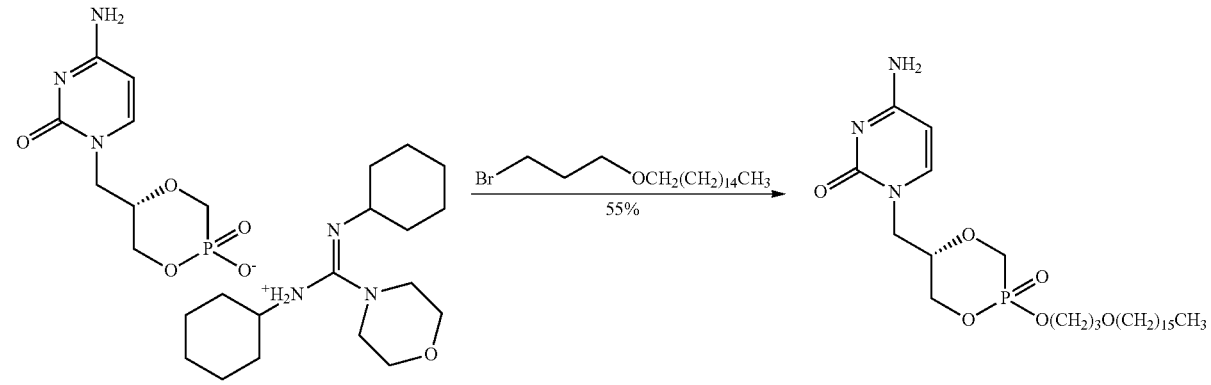

Step 3

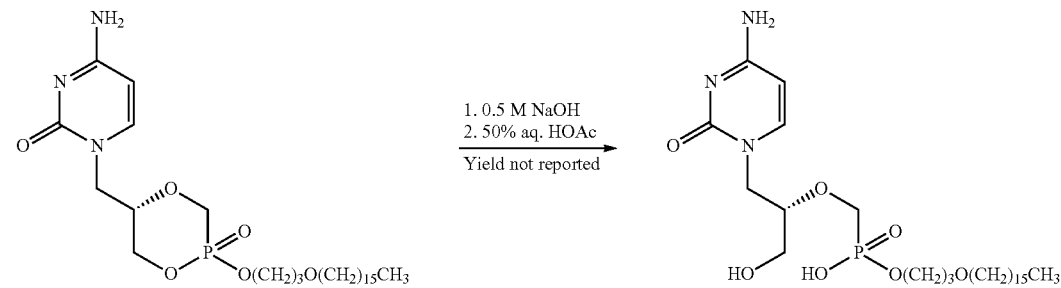

As described in U.S. Pat. No. 6,716,825, in Step 1 of the scheme above, cidofovir was suspended in N,N-DMF and N,N'-dicyclohexyl-4-morpholine-carboxamide was added. The mixture was stirred overnight to dissolve the cidofovir. The clear solution was then charged to an addition funnel and slowly added (30 min) to a stirred, hot pyridine (60° C.) solution containing 1,3-dicyclohexyl carbodiimide. The resulting reaction mixture was stirred at 100° C. for 16 h, cooled to room temperature and the solvents were removed under reduced pressure. The reaction mixture was adsorbed on silica gel and the product was purified by flash column chromatography using gradient elution ($CH_2Cl_2$ and MeOH) followed by 5:5:1 $CH_2Cl_2$/MeOH/$H_2O$. The fractions containing the product were combined and concentrated in vacuo. The product, the DCMC salt of cyclic cidofovir was isolated in a 44% yield. In step 2, a solution of cyclic cidofovir DCMC salt in dry N,N-DMF was charged with 1-bromo-3-hexadecyloxypropane and the mixture was stirred and heated at 80° C. for 6 h. The solution was concentrated in vacuo, the residue adsorbed on silica gel and purified by flash column chromatography using gradient elution ($CH_2Cl_2$ and ethanol). The product was eluted with 90:10 $CH_2Cl_2$/EtOH. The fractions containing pure product were concentrated in vacuo. Hexadecyloxypropyl-cyclic cidofovir was obtained in a 55% yield. In Step 3, hexadecyloxypropyl-cyclic cidofovir was dissolved in 0.5M NaOH and stirred at room temperature for 1.5 h. 50% aqueous acetic acid was then added dropwise to adjust the pH to 9. The precipitated hexadecyloxypropyl-cidofovir was isolated by filtration, rinsed with water, and dried. The product was crystallized from 3:1 p-dioxane/water to give hexadecyloxypropyl-cidofovir (HDP-CDV, i.e, CMX001).

Example 10A

The process as described in U.S. Pat. No. 6,716,825 according to Example 10 was repeated as follows with minor modifications.

Synthesis of hexadecyloxypropyl-cyclic cidofovir: To a heterogeneous solution of cyclic cidofovir (39 g, 0.131 mol., 1 equiv, purchased from Gilead Sciences) in N,N-DMF (2.0 L) under a nitrogen atmosphere was added N,N'-dicyclohexyl-4-morpholinecarboxamidine (DCMC) (0.131 mol, 38.51 g, 1 equiv.). This was stirred overnight. This dissolved most of the solid in the reaction mixture. To this solution was added 1-bromo-3-hexadecyloxypropane (238.45 g, 0.656 mol, 5 equiv.). The reaction mixture was heated to 80° C. and stirred for 6 hours. The crude reaction mixture was concentrated in vacuo at 80° C. The crude reaction mixture was absorbed on silica gel (300 g) and purified via column chromatography (800 g $SiO_2$). The column was eluted with dichloromethane (6 L) to remove the excess 1-bromo-3-hexadecyloxypropane. The solvent phase was then switched to 9:1 $CH_2Cl_2$:EtOH (32 L). The product came off with this solvent system. Fractions 30-39 were combined to give hexadecyloxypropyl-cyclic cidofovir (17.8 g) in a 25% yield.

Synthesis of hexadecyloxypropyl-cidofovir (HDP-CDV) with pH adjusted to 5.5 post hydrolysis: To hexadecyloxypropyl-cyclic cidofovir (4.00 g, 1.0 equivalent) was added 0.5N sodium hydroxide (118 mL, 8.0 equivalents). The solution was stirred at room temperature for 1.5 hrs. The solution remained cloudy throughout the hydrolysis. The pH was adjusted to 2.78 (desired pH was 2.5) by slow addition of concentrated acetic acid (200 mL). At this pH, the reaction was a solution. The pH was then adjusted to 5.5 using 3N NaOH and the mixture was stirred overnight at room temperature. The resulting solid was filtered and air dried (3.76 g of crude product). This material was crystallized by dissolving in 100 mL of a 3:1 p-dioxane/water mixture at 65° C. The heterogeneous reaction was filtered and allowed to stand at r.t. for ~2 hr, then placed in a refrigerator overnight.

The product was filtered and air dried for 1.5 hr. The filter funnel was transferred to a vacuum oven and the material was dried at 46° C. for 48 hr. The reaction yielded 0.93 g of an off white amorphous solid.

Synthesis of hexadecyloxypropyl-cidofovir (HDP-CDV) with pH adjusted to 4.51 post hydrolysis: To hexadecyloxypropyl-cyclic cidofovir (4.00 g, 1.0 equivalent) was added 0.5N sodium hydroxide (118 mL, 8.0 equivalents). The solution was stirred for 1.5 hrs. The solution remained cloudy throughout the hydrolysis. The pH was adjusted to 4.51 (target was 4.5) using concentrated acetic acid (9 mL). The resulting solid was filtered (solid filtered in less than 3 minutes) and dried under vacuum overnight. 3.5 g of a white solid (fine powder) was obtained. This material was crystallized from p-dioxane:water (3:1). The initial attempt to use a 10 mL/g ratio at 65° C. was unsuccessful. Very little material would dissolve at this ratio. An additional 85 mL of dioxane:water (3:1) was used. The heterogeneous solution was filtered through a sinter glass funnel while hot. The filtration took approximately 20 seconds. The solution was allowed to cool to room temperature and then placed in refrigerator overnight. The resulting solid was filtered (solid filtered in less than 1 minute). The solid (white powder) was dried in the vacuum oven at 46° C. for 48 hours (643 mg).

Synthesis of hexadecyloxypropyl-cidofovir (HDP-CDV) with pH adjusted to 3.51 post hydrolysis: To hexadecyloxypropyl-cyclic cidofovir (4.00 g, 1.0 equivalent) was added 0.5N sodium hydroxide (118 mL, 8.0 equivalents). The solution was stirred at room temperature for 1.5 hrs. The solution remained cloudy throughout the hydrolysis. The pH was adjusted to 3.51 by dropwise addition of concentrated acetic acid (55 mL) and the reaction was allowed to stand at room temperature for 3 hrs. The product was filtered and air-dried overnight. The resulting white solid was still wet in the morning. Assuming that the white solid would weigh ~3.6 g when completely dried based on the other two dried crude products described above, the crystallization was initiated by adding 40 mL of a 3:1 mixture of p-dioxane/water and heating to 65° C. Continued adding 3:1 p-dioxane/water in 10 mL portions each time bringing the temperature back to 65° C. The material was almost completely dissolved after addition of a total of 110 mL of 3:1 dioxane/water at 65° C. The mixture was filtered and stored at room temperature for 4 hrs, then placed in a refrigerator overnight.

The product was filtered and air dried for 1.5 hr, obtained 1.61 g of a white solid. A 200 mg sample was placed back on a sintered glass funnel and air dried for 48 hrs. The remaining 1.41 g was dried in a vacuum oven at 46° C. for 48 hr. The air-dried sample on the sintered glass funnel weighed 0.27 g (116-018B). The 1.41 g sample, dried in the vacuum oven weighed 1.29 g (116-018A). Both samples are white crystalline solids.

It was also observed that when post-hydrolysis pH was adjusted to 9 using concentrated acetic acid, no HDP-CDV precipitation was observed, contrary to what was described in U.S. Pat. No. 6,716,825. Further, it was observed that when the pH was greater than 3.5 post hydrolysis, a mixture of HDP-CDV free acid and HDP-CDV sodium salt was generated. It was also observed that when the pH was adjusted to 2.78, a solution was generated (from a heterogeneous solution). Without wishing to be bound by the theory, this is most likely due to the fact that protonation of the cytosine amino group generated HDP-CDV acetate salt that is soluble in the reaction solvent. All HDP-CDV samples produced in this example were of lower purity (79-91% wt/wt) compared to the high purity (>99% wt/wt) produced in Example 2 or 7.

Example 11

Crystallinity Study of CMX001

X-ray Powder Diffraction study was performed on four lots of CMX001 morphic Form A generated by the process described in Example 2 above, i.e., lots#1-5 and one lot of CMX001 Form B, i.e., lot #6, generated by recrystallizing crude CMX001 following the procedure described in U.S. Pat. No. 6,716,825 (i.e., using 3:1 p-dioxane/water) according to Example 10A. Morphic Form B was characterized as a non-stoichiometric hydrate of CMX001.

The data for each lot is provided in Tables 10-15 below and the diffractograms of each lot are provided as FIGS. 1-6.

TABLE 10

XRD data for Lot# 1 of Form A
CMX001, Lot #1

| Angle 2-Theta | d value Angstrom | Intensity Count | Intensity % |
|---|---|---|---|
| 2.812 | 31.39324 | 3040 | 100 |
| 3.48 | 25.36881 | 1.42 | 0 |
| 5.546 | 15.92261 | 1390 | 45.7 |
| 6.898 | 12.8036 | 8.18 | 0.3 |
| 7.96 | 11.0981 | 11.3 | 0.4 |
| 8.242 | 10.71866 | 10.9 | 0.4 |
| 8.501 | 10.39264 | 7.81 | 0.3 |
| 8.86 | 9.07267 | 18.9 | 0.6 |
| 9.36 | 9.44104 | 28.1 | 0.9 |
| 9.82 | 8.9998 | 8.99 | 0.3 |
| 10.22 | 8.64843 | 14.1 | 0.5 |
| 11.051 | 7.99976 | 344 | 11.3 |
| 11.477 | 7.70419 | 28.7 | 0.9 |
| 12.032 | 7.34989 | 93.3 | 3.1 |
| 12.675 | 6.97818 | 161 | 5.3 |
| 13.507 | 6.55026 | 655 | 21.5 |
| 13.823 | 6.40129 | 227 | 7.5 |
| 14.309 | 6.18484 | 474 | 15.6 |
| 15.063 | 5.87679 | 26.5 | 0.9 |
| 15.638 | 5.66229 | 368 | 12.1 |
| 16.58 | 5.3425 | 102 | 3.4 |
| 16.871 | 5.25115 | 194 | 6.4 |
| 17.875 | 4.96837 | 1228 | 40.4 |
| 18.345 | 4.83238 | 609 | 20 |
| 18.98 | 4.67201 | 727 | 23.9 |
| 19.292 | 4.59714 | 1384 | 45.5 |
| 20.22 | 4.38821 | 490 | 16.1 |
| 20.52 | 4.32473 | 841 | 27.6 |
| 20.83 | 4.26111 | 1531 | 50.3 |
| 21.31 | 4.16624 | 1467 | 48.2 |
| 22.141 | 4.01157 | 380 | 12.5 |
| 22.723 | 3.91013 | 475 | 15.6 |
| 23.311 | 3.8129 | 1348 | 44.3 |
| 23.885 | 3.72255 | 601 | 19.8 |
| 24.293 | 3.66085 | 539 | 17.7 |
| 24.97 | 3.56311 | 670 | 22 |
| 25.72 | 3.46094 | 469 | 15.4 |
| 25.938 | 3.43235 | 553 | 18.2 |
| 26.635 | 3.34413 | 77.8 | 2.6 |
| 27.168 | 3.27969 | 115 | 3.8 |
| 27.785 | 3.20821 | 77.7 | 2.6 |
| 28.12 | 3.17077 | 16.6 | 0.5 |
| 28.651 | 3.11316 | 80.2 | 2.6 |
| 29.52 | 3.0235 | 197 | 6.5 |
| 30.107 | 2.96585 | 129 | 4.2 |
| 31.156 | 2.86832 | 69.9 | 2.3 |
| 31.457 | 2.84165 | 86.1 | 2.8 |
| 31.918 | 2.80163 | 76.2 | 2.5 |
| 32.643 | 2.741 | 70.3 | 2.3 |
| 33.268 | 2.6909 | 105 | 3.5 |
| 33.76 | 2.65284 | 22.6 | 0.7 |

TABLE 10-continued

XRD data for Lot# 1 of Form A
CMX001, Lot #1

| Angle 2-Theta | d value Angstrom | Intensity Count | Intensity % |
|---|---|---|---|
| 34.203 | 2.61947 | 89.9 | 3 |
| 34.44 | 2.602 | 61.2 | 2 |
| 34.715 | 2.58204 | 79.1 | 2.6 |
| 35.597 | 2.52006 | 34.9 | 1.1 |
| 36.172 | 2.48131 | 187 | 6.1 |
| 37.015 | 2.42667 | 118 | 3.9 |
| 37.2 | 2.41504 | 101 | 3.3 |
| 37.701 | 2.38408 | 90.7 | 3 |
| 39.06 | 2.30422 | 106 | 3.5 |
| 39.788 | 2 26371 | 101 | 3.3 |
| 39.984 | 2.25309 | 86.1 | 2.8 |
| 42.16 | 2.14167 | 98.3 | 3.2 |
| 42.361 | 2.13198 | 131 | 4.3 |
| 42.794 | 2.11139 | 86.7 | 2.9 |
| 43.424 | 2.08221 | 95.2 | 3.1 |
| 44.32 | 2.04218 | 37.4 | 1.2 |
| 44.46 | 2.03608 | 45.9 | 1.5 |

TABLE 11

XRD data for Lot# 2 of Form A
CMX001, Lot# 2

| Angle 2-Theta ° | d value Angstrom | Intensity Count | Intensity % |
|---|---|---|---|
| 2.813 | 31.37655 | 2940 | 100 |
| 3.392 | 26.02397 | 3.42 | 0.1 |
| 3.709 | 23.33029 | 3.32 | 0.1 |
| 4.174 | 21.15431 | 6.52 | 0.2 |
| 4.678 | 18.87577 | 7.88 | 0.3 |
| 5.556 | 15.69282 | 1312 | 44.6 |
| 7.817 | 11.30133 | 10.9 | 0.4 |
| 8.12 | 10.87978 | 733 | 0.2 |
| 8.18 | 10.80011 | 12.2 | 0.4 |
| 8.261 | 10.69376 | 5.64 | 0.2 |
| 8.34 | 10.59327 | 16.3 | 0.6 |
| 8.549 | 10.33533 | 16.4 | 0.6 |
| 8.872 | 9.95917 | 10.0 | 0.4 |
| 9.362 | 9.43948 | 28.3 | 1 |
| 10.184 | 8.67884 | 9.08 | 0.3 |
| 10.46 | 8.45063 | 8.64 | 0.3 |
| 10.56 | 8.37073 | 15.6 | 0.5 |
| 11.039 | 8.00878 | 375 | 12.7 |
| 11.56 | 7.64877 | 2.23 | 0.1 |
| 12.011 | 7.36279 | 131.2 | 3 |
| 12.44 | 7.10961 | 27.4 | 0.9 |
| 12.754 | 6.9353 | 31 | 1.1 |
| 13.515 | 6.54625 | 751 | 25.6 |
| 13.82 | 6.40262 | 234 | 8 |
| 14.314 | 6.18292 | 468 | 15.9 |
| 14.94 | 5.92506 | 4.73 | 0.2 |
| 15.631 | 5.66460 | 354 | 12.1 |
| 16.126 | 5.49202 | 15.9 | 0.5 |
| 16.6 | 5.33611 | 97.7 | 3.3 |
| 16.863 | 5.25339 | 210 | 7.1 |
| 17.864 | 4.96127 | 1128 | 38.4 |
| 18.34 | 4.83354 | 524 | 17.8 |
| 18.96 | 4.67689 | 736 | 25.1 |
| 19.278 | 4.60043 | 1401 | 47.7 |
| 20.2 | 4.39251 | 385 | 13.1 |
| 20.5 | 4.3289 | 828 | 28.2 |
| 20.803 | 4.2666 | 1297 | 44.1 |
| 21.289 | 4.17028 | 1412 | 48 |
| 22.14 | 4.0110 | 303 | 10.3 |
| 22.74 | 3.9073 | 398 | 13.5 |
| 23.292 | 3.816 | 1381 | 47 |
| 23.872 | 3.72457 | 647 | 22 |
| 24.27 | 3.66435 | 460 | 15.7 |
| 24.959 | 3.56471 | 649 | 22.1 |
| 25.68 | 3.45629 | 442 | 15 |

TABLE 11-continued

XRD data for Lot# 2 of Form A
CMX001, Lot# 2

| Angle 2-Theta ° | d value Angstrom | Intensity Count | Intensity % |
|---|---|---|---|
| 25.908 | 3.43625 | 585 | 19.9 |
| 26.68 | 3.33852 | 104 | 3.5 |
| 27.16 | 3.28064 | 160 | 5.4 |
| 27.747 | 3.21258 | 64.9 | 2 9 |
| 28.567 | 3.12212 | 93.6 | 3.2 |
| 29.467 | 3.02076 | 186 | 6.3 |
| 30.084 | 2.9681 | 162 | 5.6 |
| 30.32 | 2.89887 | 9.3 | 0.3 |
| 31.069 | 2.87711 | 52.4 | 1.0 |
| 31.272 | 2.85798 | 64.3 | 2.2 |
| 31.966 | 2.79752 | 104 | 16 |
| 32.628 | 2.74227 | 74.4 | 2.5 |
| 33.253 | 2.69213 | 165 | 3.6 |
| 34.284 | 2.61351 | 68.5 | 2 3 |
| 34.665 | 2.56565 | 77.1 | 2.6 |
| 35.479 | 2.52812 | 43.8 | 1.5 |
| 36.111 | 2.48537 | 1e3 | 5.6 |
| 37.103 | 2.42114 | 67.6 | 2.3 |
| 37.738 | 2.38181 | 30.4 | 1 |
| 37.997 | 2.36618 | 34 | 1.2 |
| 38.3 | 2.34817 | 40 3 | 1.4 |
| 38.36 | 2.34464 | 35.2 | 1.2 |
| 38.837 | 2.31694 | 42.2 | 1.4 |
| 39.122 | 2 3007 | 40.1 | 1.4 |
| 39.823 | 2.26183 | 55.7 | 1.9 |
| 40.12 | 2.24575 | 78.3 | 2.7 |
| 40.52 | 2.2246 | 9.1 | 0 3 |
| 40.858 | 2.213686 | 12.4 | 0.4 |
| 41.137 | 2.19256 | 59.7 | 2 |
| 41.58 | 2.1702 | 39.8 | 1.4 |
| 42.312 | 2.13434 | 93.7 | 3 2 |
| 42.844 | 2.10905 | 45.7 | 1.6 |
| 43.44 | 2.08149 | 31.5 | 1.1 |
| 43.58 | 2.07514 | 49.4 | 1.7 |
| 43.987 | 2.05668 | 13.9 | 0.5 |
| 44.26 | 2.04481 | 24.3 | 0.8 |
| 44.56 | 2.03172 | 18.3 | 0.6 |
| 44.66 | 2.02742 | 17.7 | 0.6 |

TABLE 12

XRD data for Lot# 3 of Form A
CMX001, Lot # 3

| Angle 2-Theta ° | d value Angstrom | Intensity Count | Intensity % |
|---|---|---|---|
| 2.763 | 31.953 | 10790 | 100 |
| 3.32 | 26.59103 | 1.95 | 0 |
| 3.593 | 24.57207 | 9.35 | 0.1 |
| 3.040 | 22.94288 | 8.6 | 0.1 |
| 4.283 | 20.61405 | 6.92 | 0.1 |
| 5.518 | 16.00202 | 2857 | 26.5 |
| 6.56 | 13.46313 | 11.7 | 0.1 |
| 7.20 | 12.13314 | 4.63 | 0 |
| 7.553 | 11.6953 | 3.98 | 0 |
| 7.76 | 11.38360 | 6.26 | 0.1 |
| 9.393 | 9.40761 | 25.7 | 0.2 |
| 9.896 | 8.93096 | 5.94 | 0.1 |
| 10.071 | 8.7758 | 9.32 | 0.1 |
| 10.338 | 8.55003 | 134 | 0.1 |
| 11.006 | 8.03277 | 692 | 5.5 |
| 11.99 | 7.37541 | 64.5 | 0.6 |
| 12.402 | 7.13137 | 14.9 | 0.1 |
| 12.712 | 6.95809 | 36.7 | 0.3 |
| 13.444 | 6.58089 | 601 | 5.6 |
| 13.702 | 6.42027 | 303 | 2.8 |
| 14.233 | 6.21785 | 399 | 3.7 |
| 14.86 | 5.95678 | 0.04 | 0 |
| 15.02 | 5.89368 | 32.7 | 0.3 |
| 15.1 | 5.06264 | 0.75 | 0.1 |
| 15.589 | 5.67976 | 424 | 3.9 |
| 16.039 | 5.52162 | 17.6 | 0.2 |
| 16.56 | 5.34891 | 90.6 | 0.8 |
| 16.833 | 5.26275 | 279 | 2.6 |
| 17.827 | 4.97156 | 935 | 8.7 |
| 18.296 | 4.84516 | 471 | 4.4 |
| 18.96 | 4.67689 | 692 | 6.4 |
| 19.236 | 4.61035 | 1401 | 13 |
| 20.17 | 4.3989 | 346 | 3.2 |
| 20.502 | 4.3285 | 656 | 6.1 |
| 20.756 | 4.27611 | 1191 | 11 |
| 21.243 | 4.17912 | 1375 | 12.7 |
| 22.115 | 4.01625 | 365 | 3.4 |
| 22.624 | 3.92713 | 363 | 3.4 |
| 23.258 | 3.82146 | 1531 | 14.2 |
| 23.832 | 3.73061 | 567 | 5.3 |
| 24.227 | 3.67074 | 424 | 3.9 |
| 24.916 | 3.57081 | 642 | 6 |
| 25.64 | 3.47166 | 440 | 4.1 |
| 25.889 | 3.43874 | 658 | 6.1 |
| 26.579 | 3.351 | 02.4 | 0.8 |
| 27.136 | 3.28351 | 177 | 1.6 |
| 27.714 | 3.21632 | 97 | 0.9 |
| 28.551 | 3.12303 | 132 | 1.2 |
| 28.96 | 3.08668 | 46 | 0.4 |
| 29.463 | 3.02925 | 172 | 1.6 |
| 30.003 | 2.97597 | 111 | 1 |
| 31.145 | 2.86937 | 73.2 | 0.7 |
| 31.941 | 2.79966 | 66.8 | 0.6 |
| 32.586 | 2.74569 | 60.3 | 0.8 |
| 33.141 | 2.70096 | 119 | 1.1 |
| 33.66 | 2.66049 | 14.1 | 0.1 |
| 34.242 | 2.6166 | 90.3 | 0.8 |
| 34.590 | 2.59045 | 75.0 | 0.7 |
| 35.990 | 2.53371 | 18.8 | 0.2 |
| 36.041 | 2.48997 | 175 | 1.6 |
| 36.4 | 2.46626 | 98.3 | 0.9 |
| 37.068 | 2.42332 | 60.9 | 0.6 |
| 37.80 | 2.37324 | 26.7 | 0.2 |
| 38.418 | 2.34122 | 58.0 | 0.5 |
| 38.878 | 2.31456 | 52.1 | 0.5 |
| 39.078 | 2.30319 | 50.6 | 0.5 |
| 39.398 | 2.28521 | 27.4 | 0.3 |
| 39.766 | 2.26494 | 49.4 | 0.5 |
| 39.80 | 2.25871 | 41.2 | 0.4 |
| 40.03 | 2.25057 | 50.4 | 0.5 |
| 40.468 | 2.22723 | 14.5 | 0.1 |
| 41.176 | 2.19057 | 82 | 0.8 |
| 41.74 | 2.16225 | 29.9 | 0.3 |
| 42.029 | 2.14803 | 445 | 0.4 |
| 42.233 | 2.13813 | 89.4 | 0.8 |
| 42.711 | 2.11531 | 41.7 | 0.4 |
| 42.932 | 2.10494 | 41.1 | 0.4 |
| 43.517 | 2.07799 | 51.4 | 0.5 |
| 43.8 | 2.06522 | 23.5 | 0.2 |
| 44.136 | 2.05026 | 30.8 | 0.3 |
| 44.516 | 2.03362 | 38.3 | 0.4 |
| 44.78 | 2.02227 | 19 | 0.2 |

TABLE 13

XRD data for Lot# 4 of Form A
CMX001, Lot # 4

| Angle 2-Theta ° | d value Angstrom | Intensity Count | Intensity % |
|---|---|---|---|
| 2.157 | 32.01601 | 4072 | 100 |
| 3.292 | 26.81566 | 0.76 | 0.2 |
| 3.351 | 26.34243 | 0.9 | 0 |
| 5.496 | 16.06721 | 1576 | 38.7 |

TABLE 13-continued

XRD data for Lot# 4 of Form A CMX001, Lot # 4

| Angle 2-Theta ° | d value Angstrom | Intensity Count | Intensity % % |
|---|---|---|---|
| 6.078 | 14.52958 | 7.9 | 0.2 |
| 6.008 | 12.97230 | 11.4 | 0.3 |
| 7.08 | 12.47543 | 6.75 | 0.2 |
| 8.191 | 10.70574 | 0.71 | 0.2 |
| 8.883 | 9.94741 | 15.6 | 0.4 |
| 9.304 | 9.49806 | 25.0 | 0.6 |
| 9.38 | 9.42095 | 15.5 | 0.4 |
| 9.82 | 8.9990 | 3.23 | 0.1 |
| 10.052 | 8.79244 | 9.86 | 0.2 |
| 10.38 | 8.51640 | 5.01 | 0.1 |
| 11.001 | 8.03612 | 479 | 11.8 |
| 11.965 | 7.39067 | 101 | 2.6 |
| 12.4 | 7.13232 | 35.3 | 0.9 |
| 12.719 | 6.95408 | 63.6 | 1.6 |
| 13.45 | 6.57702 | 656 | 21 |
| 13.767 | 6.42726 | 240 | 5.9 |
| 14.27 | 6 20162 | 514 | 12.6 |
| 15.012 | 5.09664 | 26.2 | 0.6 |
| 15.576 | 5.60471 | 450 | 11 |
| 16.08 | 5.50748 | 10.2 | 0.3 |
| 16.555 | 5.35042 | 86.1 | 2.1 |
| 16.809 | 5.27025 | 252 | 6.2 |
| 17.826 | 4.97171 | 1254 | 30.8 |
| 18.297 | 4.84485 | 627 | 15.4 |
| 18.94 | 4.68179 | 794 | 19.5 |
| 19.232 | 4.6113 | 1575 | 38.7 |
| 20.16 | 4.40113 | 370 | 9.1 |
| 20.44 | 4.34147 | 758 | 18.6 |
| 20.757 | 4.27586 | 1506 | 37 |
| 21.261 | 4.17569 | 1695 | 41.6 |
| 22.095 | 4.01968 | 344 | 8.4 |
| 22.68 | 3.91755 | 419 | 10.3 |
| 23.263 | 3.82059 | 1661 | 40.8 |
| 23.825 | 3.7318 | 786 | 19.3 |
| 24.232 | 3.66997 | 623 | 15.3 |
| 24.915 | 3.57092 | 663 | 21.2 |
| 25.62 | 3.47422 | 453 | 11.1 |
| 25.894 | 3.43804 | 019 | 20.1 |
| 26.609 | 3.34724 | 133 | 3.3 |
| 27.107 | 3.26697 | 210 | 5.2 |
| 27.675 | 3.22071 | 89.9 | 2.2 |
| 28.564 | 3.12245 | 139 | 3.4 |
| 29.493 | 3.02622 | 224 | 5.5 |
| 30.056 | 2.9708 | 170 | 4.2 |
| 30.62 | 2.91735 | 32 | 0.0 |
| 31.132 | 2.67053 | 136.8 | 2.1 |
| 31.48 | 2.83958 | 35.1 | 0.9 |
| 31.977 | 2.79656 | 100 | 2.6 |
| 32.509 | 2.74546 | 110 | 2.9 |
| 33.224 | 2.69437 | 97.4 | 2.4 |
| 34.174 | 2.62163 | 81.4 | 2 |
| 34.55 | 2.59393 | 100 | 2.7 |
| 35.44 | 2.59084 | 30 | 0.9 |
| 36.096 | 2.40637 | 190 | 4.7 |
| 36.38 | 2.46757 | 100 | 2.7 |
| 36.982 | 2.42876 | 104 | 2.5 |
| 37.18 | 241629 | 62.8 | 1.5 |
| 37.712 | 2.3834 | 27A | 0.7 |
| 38.094 | 2.36039 | 32.9 | 0.0 |
| 38.46 | 2.33877 | 53.1 | 1.3 |
| 38.953 | 2.31032 | 403 | 1.2 |
| 39.804 | 2.26203 | 63.7 | 1.6 |
| 39.958 | 2.25448 | 57.9 | 1.4 |
| 40.06 | 2.24897 | 63.5 | 1.6 |
| 40.56 | 2.22239 | 2.88 | 0.1 |
| 41 | 2.19955 | 52.1 | 1.3 |
| 41.262 | 2.1862 | 07.6 | 2.2 |
| 42.191 | 2.14019 | 123 | 3 |
| 43.543 | 2.07679 | 51.9 | 1.3 |
| 43.06 | 2.06253 | 30.2 | 0.7 |
| 44.16 | 2.134922 | 23.6 | 0.6 |
| 44.28 | 2.04394 | 39.2 | 1 |
| 44.48 | 2.03521 | 0.25 | 0 |
| 44.58 | 2.03087 | 15.9 | 0.4 |
| 44.791 | 2.02178 | 28 | 0.7 |

TABLE 14

XRD data for Lot# 5 of Form A CMX001, Lot # 5

| Angle 2-Theta | d value Angstrom | Intensity Count | Intensity % |
|---|---|---|---|
| 2.768 | 31.88798 | 3.838 | 100 |
| 3.183 | 27.73473 | 0.41 | 0 |
| 4.24 | 20.8225 | 6.03 | 0.2 |
| 4.58 | 19.27003 | 6.44 | 0.2 |
| 5.503 | 16.04659 | 1496 | 39 |
| 6.04 | 14.62099 | 1.21 | 0 |
| 6.28 | 14.06312 | 8.81 | 0.2 |
| 7.386 | 11.95927 | 13 | 0.3 |
| 7.763 | 11.37926 | 10.9 | 0.3 |
| 8.261 | 10.69402 | 15.1 | 0.4 |
| 8.526 | 10.36309 | 2.49 | 0.1 |
| 8.9 | 9.92794 | 16.4 | 0.4 |
| 8.96 | 9.86159 | 16.9 | 0.4 |
| 9.351 | 9.45038 | 29.2 | 0.8 |
| 9.838 | 8..98344 | 9.55 | 0.2 |
| 10.204 | 8.66227 | 20.4 | 0.5 |
| 10.58 | 8.35495 | 14.1 | 0.4 |
| 10.64 | 830,797 | 26.8 | 0.7 |
| 11.012 | 8.02841 | 411 | 10.7 |
| 11.416 | 7.74462 | 13.7 | 0.4 |
| 11.981 | 7.38084 | 79.7 | 2.1 |
| 12.42 | 7.12101 | 29.2 | 0.8 |
| 12.71 | 6.95906 | 51.1 | 1.3 |
| 13.465 | 6.57066 | 772 | 20.1 |
| 13.776 | 6.42279 | 245 | 6.4 |
| 14.271 | 6.20149 | 493 | 12.8 |
| 15.044 | 5.88442 | 27 | 0.7 |
| 15.589 | 5.67994 | 441 | 11.5 |
| 16.14 | 5.48714 | 8.48 | 0.2 |
| 16.56 | 5.34891 | 91.1 | 2.4 |
| 16.841 | 5.2602 | 260 | 6.8 |
| 17.842 | 4.96733 | 1316 | 34.3 |
| 18.315 | 4.84002 | 653 | 17 |
| 18.94 | 4.68179 | 746 | 19.4 |
| 19.24 | 4.60945 | 1502 | 39.1 |
| 20.14 | 4.40546 | 389 | 10.1 |
| 20.48 | 4.33308 | 795 | 20.7 |
| 20.769 | 4.27346 | 1452 | 37.8 |
| 21.277 | 4.17251 | 1633 | 42.5 |
| 22.126 | 4.01425 | 361 | 9.4 |
| 22.662 | 3.92065 | 435 | 11.3 |
| 23.272 | 3.81921 | 1579 | 41.1 |
| 23.85 | 83.727 | 657 | 17.1 |
| 24.264 | 3.66529 | 537 | 14 |
| 24.947 | 3.56638 | 779 | 20.3 |
| 25.642 | 3.47125 | 411 | 10.7 |
| 25.909 | 53.4361 | 724 | 18.9 |
| 26.574 | 3.36158 | 112 | 2.9 |
| 27.155 | 3.26117 | 166 | 4.3 |
| 27.691 | 3.21894 | 82.4 | 2.1 |
| 28.061 | 3.17735 | 21.3 | 0.6 |
| 28.567 | 3.12215 | 124 | 3.2 |
| 29.501 | 3.02541 | 231 | 6 |
| 30.078 | 2.96869 | 163 | 4.2 |
| 30.584 | 2.92067 | 28.8 | 0.8 |
| 31.144 | 2.8694 | 92.4 | 2.4 |
| 31.38 | 2.84843 | 59.8 | 1.6 |
| 31.974 | 2.79683 | 91.1 | 2.4 |
| 32.626 | 2.74245 | 96.6 | 2.5 |
| 33.179 | 2.69799 | 104 | 2.7 |

TABLE 14-continued

XRD data for Lot# 5 of Form A
CMX001, Lot # 5

| Angle 2-Theta | d value Angstrom | Intensity Count | Intensity % |
|---|---|---|---|
| 33.76 | 2.65284 | 10.3 | 0.3 |
| 34.226 | 2.61779 | 99 | 2.6 |
| 34.6 | 2.59037 | 104 | 2.7 |
| 35.447 | 2.53038 | 48.6 | 1.3 |
| 36.033 | 2.49055 | 195 | 5.1 |
| 36.48 | 2.46104 | 99.8 | 2.6 |
| 37.096 | 2.42155 | 82.7 | 2.2 |
| 37.625 | 2.38871 | 16.2 | 0.4 |
| 37.907 | 2.3716 | 24.1 | 0.6 |
| 38.039 | 2.36366 | 24.4 | 0.6 |
| 38.353 | 2.34507 | 28.7 | 0.7 |
| 38.45 | 2.33938 | 66.7 | 1.7 |
| 38.54 | 2.3341 | 50.8 | 1.3 |
| 38.934 | 2.3114 | 69.5 | 1.8 |
| 39.5 | 2.27956 | 11.2 | 0.3 |
| 39.919 | 2.25658 | 68.1 | 1.8 |
| 40.5 | 2.22555 | 43.7 | 1.1 |
| 40.96 | 2.20161 | 48.4 | 1.3 |
| 41.212 | 2.18873 | 68.8 | 1.8 |
| 42.193 | 2.14006 | 112 | 2.9 |
| 42.763 | 2.11284 | 57 | 1.5 |
| 43.361 | 2.0851 | 90.8 | 2.4 |
| 43.96 | 2.05807 | 23.7 | 0.6 |
| 44.131 | 2.0505 | 13.1 | 0.3 |
| 44.38 | 2.03956 | 11.5 | 0.3 |
| 44.599 | 2.03006 | 18.6 | 0.5 |
| 44.809 | 2.02103 | 25.1 | 0.7 |

TABLE 15

XRD data for Lot# 6
CMX001, Lot# 6

| Angle 2-Theta.* | d value Angstrom | Intensity Count | Intensity % |
|---|---|---|---|
| 2.32 | 38.04996 | 126 | 3.4 |
| 2.882 | 30.62985 | 3726 | 100 |
| 3.642 | 24.24355 | 4.49 | 0.1 |
| 3.739 | 23.60985 | 14.4 | 0.4 |
| 4.398 | 20.07461 | 11.3 | 0.3 |
| 5.76 | 15.33156 | 481 | 12.9 |
| 7.74 | 11.41305 | 5.49 | 0.1 |
| 8.678 | 10.18152 | 15.9 | 0.4 |
| 9.42 | 9.38104 | 11.1 | 0.3 |
| 11.576 | 7.638 | 96.9 | 2.6 |
| 12.544 | 7.05116 | 202 | 5.4 |
| 12.84 | 6.88901 | 47.7 | 1.3 |
| 13.191 | 6.70641 | 27.7 | 0.7 |
| 15.572 | 5.686 | 36.3 | 1 |
| 16.583 | 5.34163 | 4.26 | 0.1 |
| 17.432 | 5.08328 | 80.5 | 2.2 |
| 18.197 | 4.87131 | 45.8 | 1.2 |
| 19.281 | 4.59985 | 13.8 | 0.4 |
| 20.12 | 4.40979 | 31.7 | 0.9 |
| 20.315 | 4.36785 | 65.8 | 1.8 |
| 20.795 | 4.26807 | 165 | 4.4 |
| 21.64 | 4.10327 | 123 | 3.3 |
| 22.548 | 3.9401 | 53.1 | 1.4 |
| 23.302 | 3.81436 | 27 | 0.7 |
| 23.973 | 3.70911 | 120 | 3.2 |
| 24.89 | 3.57451 | 35.7 | 1 |
| 25.264 | 3.52235 | 4.38 | 0.1 |
| 25.68 | 3.46624 | 8.59 | 0.2 |
| 25.76 | 3.45566 | 13.5 | 0.4 |
| 26.706 | 3.33536 | 4.72 | 0.1 |
| 27.173 | 3.27907 | 8.99 | 0.2 |
| 27.977 | 3.1867 | 20.2 | 0.5 |
| 28.343 | 3.14638 | 9.39 | 0.3 |
| 28.874 | 3.08969 | 10.2 | 0.3 |
| 29.601 | 3.01544 | 8.21 | 0.2 |
| 31.495 | 2.83823 | 18.4 | 0.5 |
| 34.011 | 2.83382 | 5.23 | 0.1 |

TABLE 15-continued

XRD data for Lot# 6
CMX001, Lot# 6

| Angle 2-Theta.* | d value Angstrom | Intensity Count | Intensity % |
|---|---|---|---|
| 40.788 | 2.2105 | 5.9 | 0.2 |
| 41.78 | 2.16029 | 4.64 | 0.1 |
| 42.28 | 2.13588 | 1.76 | 0 |
| 42.533 | 2.12377 | 3.61 | 0.1 |
| 44.651 | 2.0278 | 3.94 | 0.1 |

Figure 7:
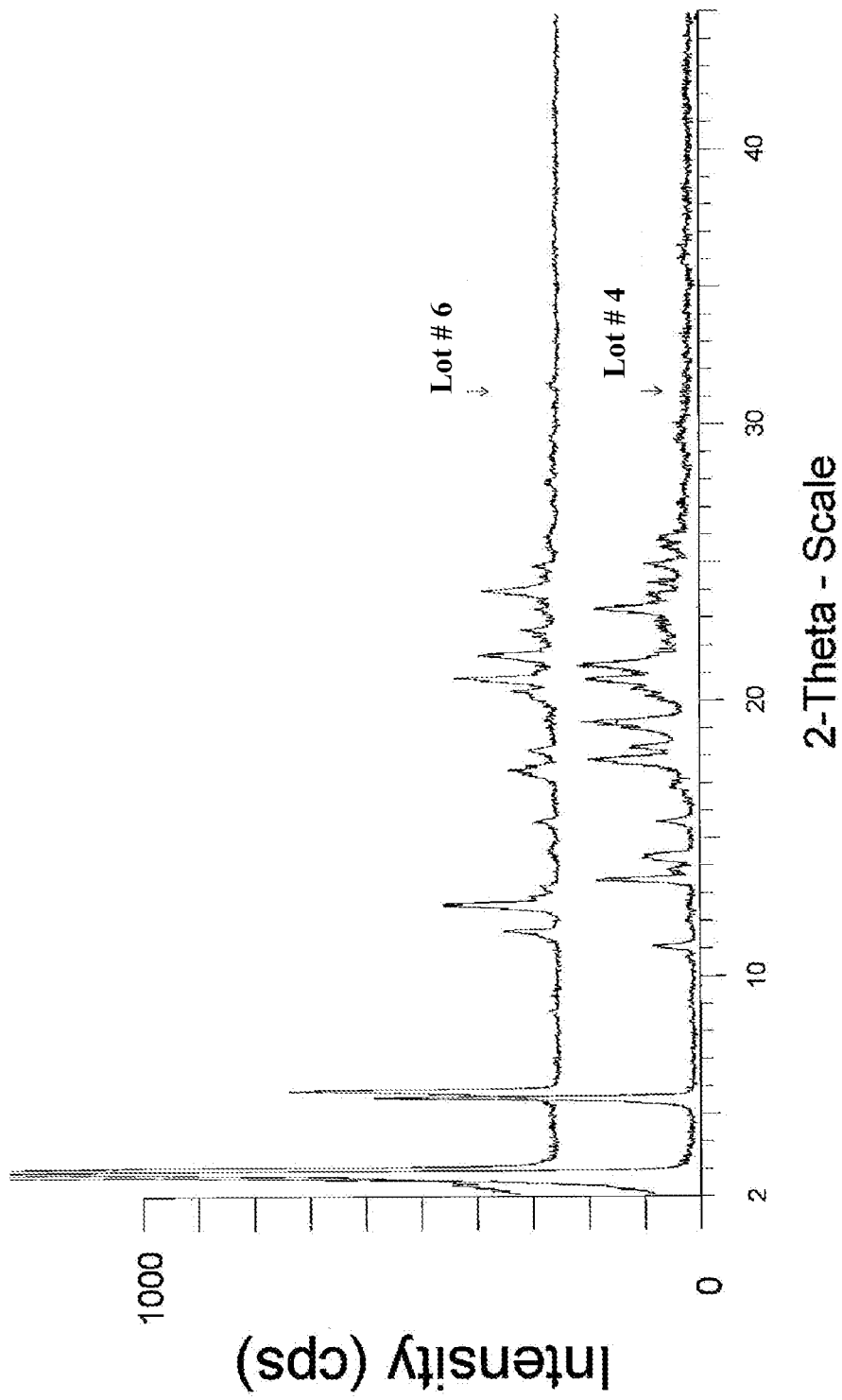
FIG. 7 is overlaid X-ray diffractograms of Form A (Lot#4) and Form B (Lot #6).
Figure 8A:
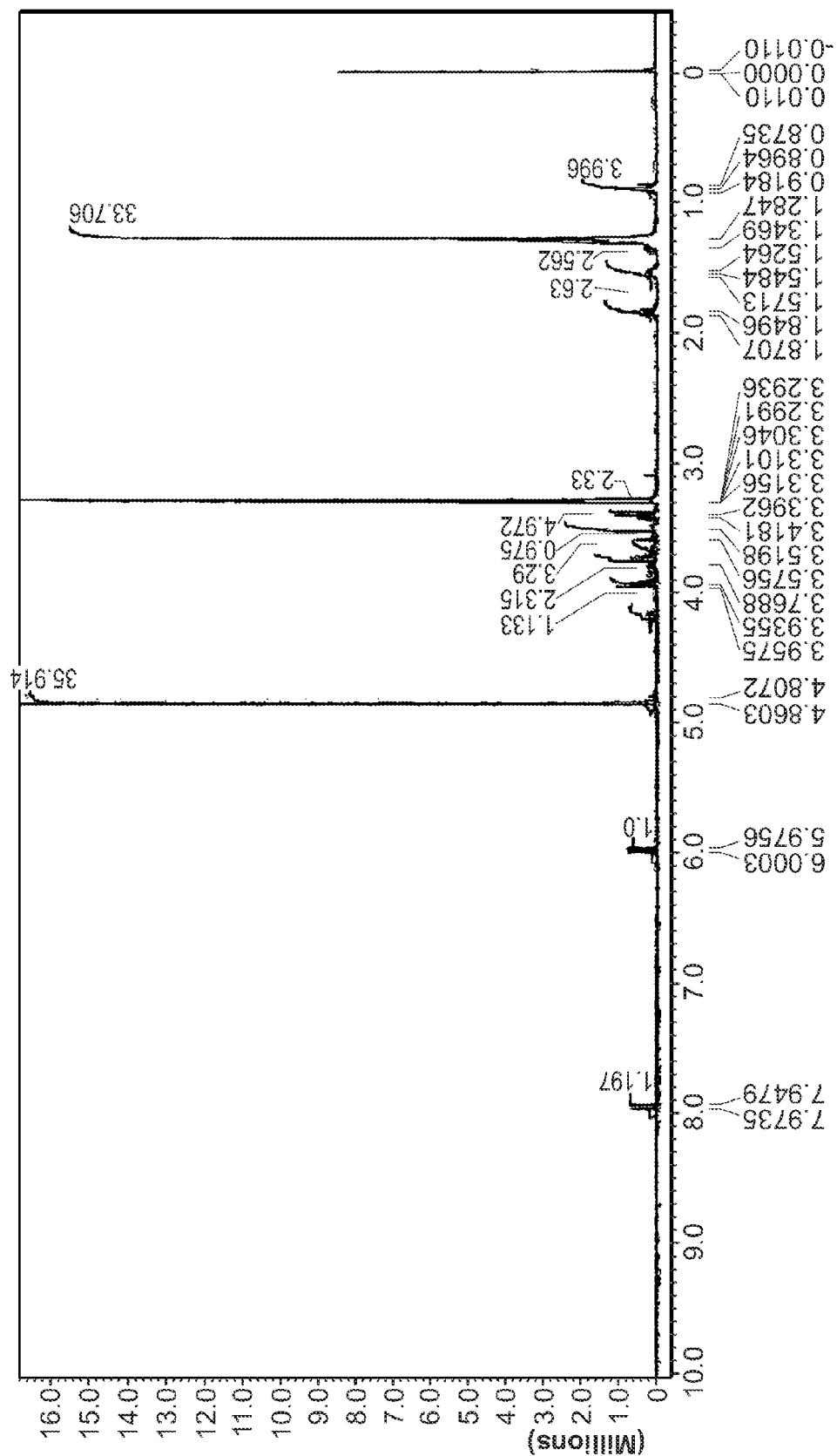
FIGS. 8(a)-(d) are $^1$H-NMR spectra of Form A (Lot#5).
Figure 8B:
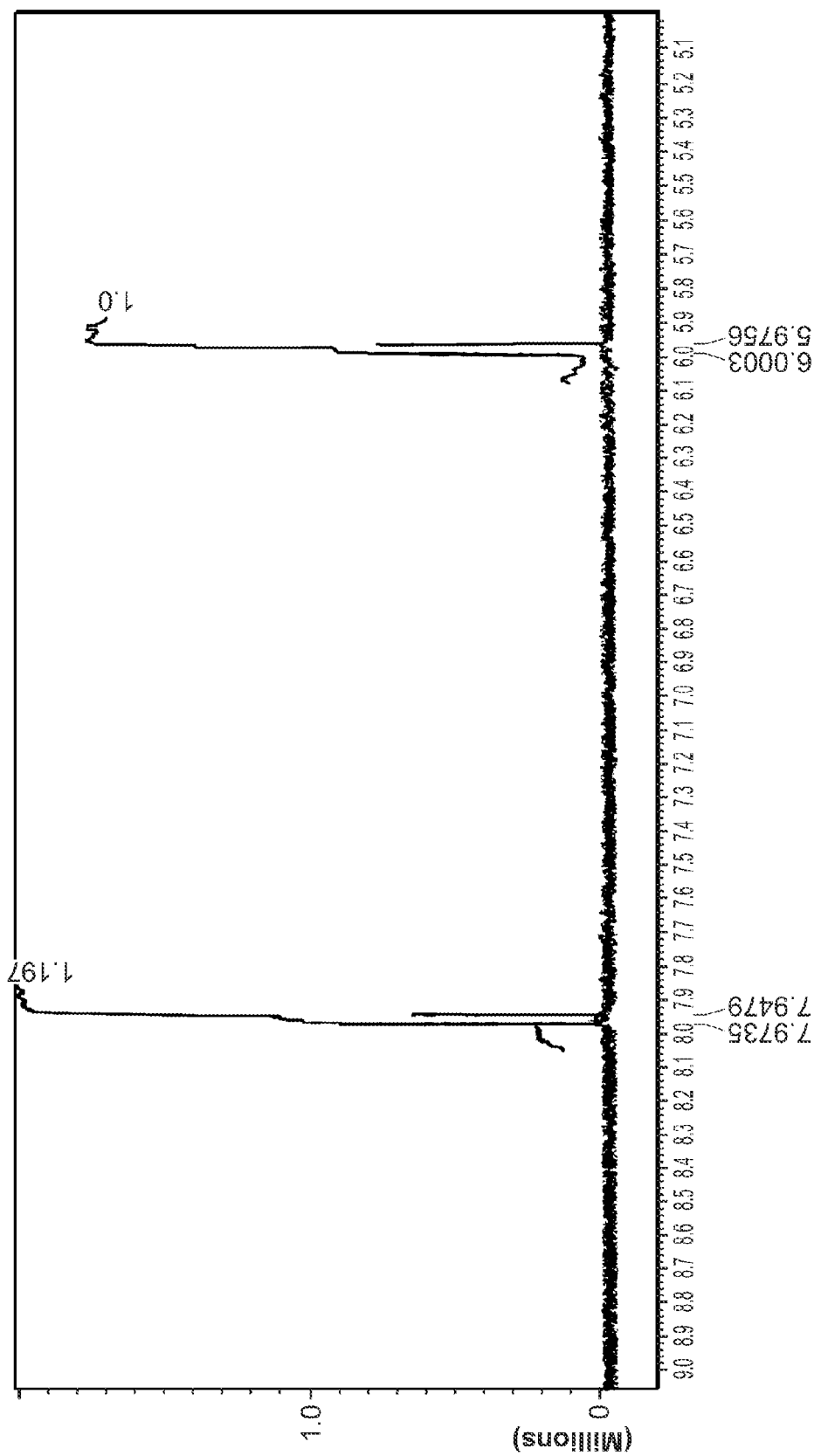
Figure 8C:
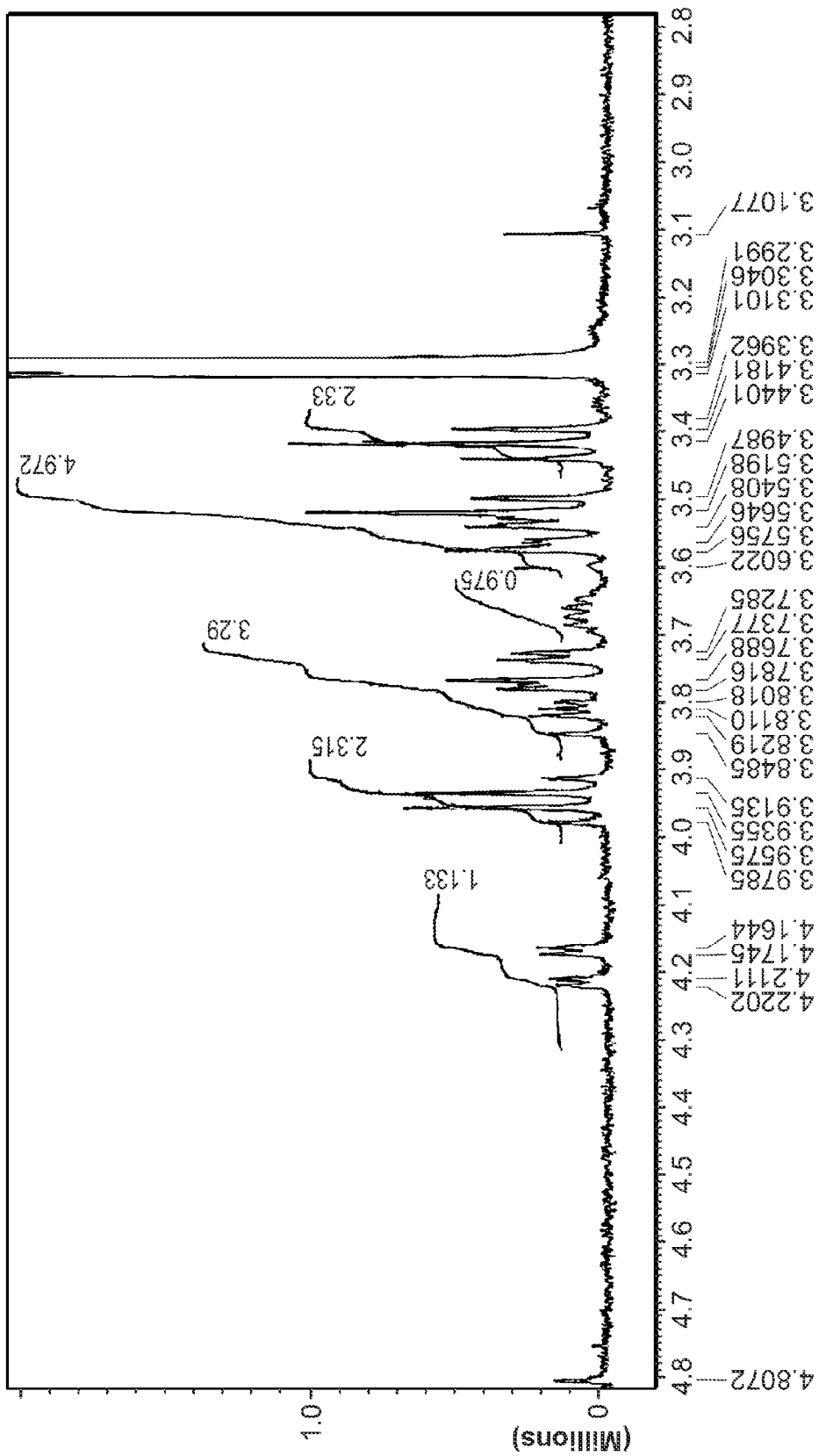
Figure 8D:
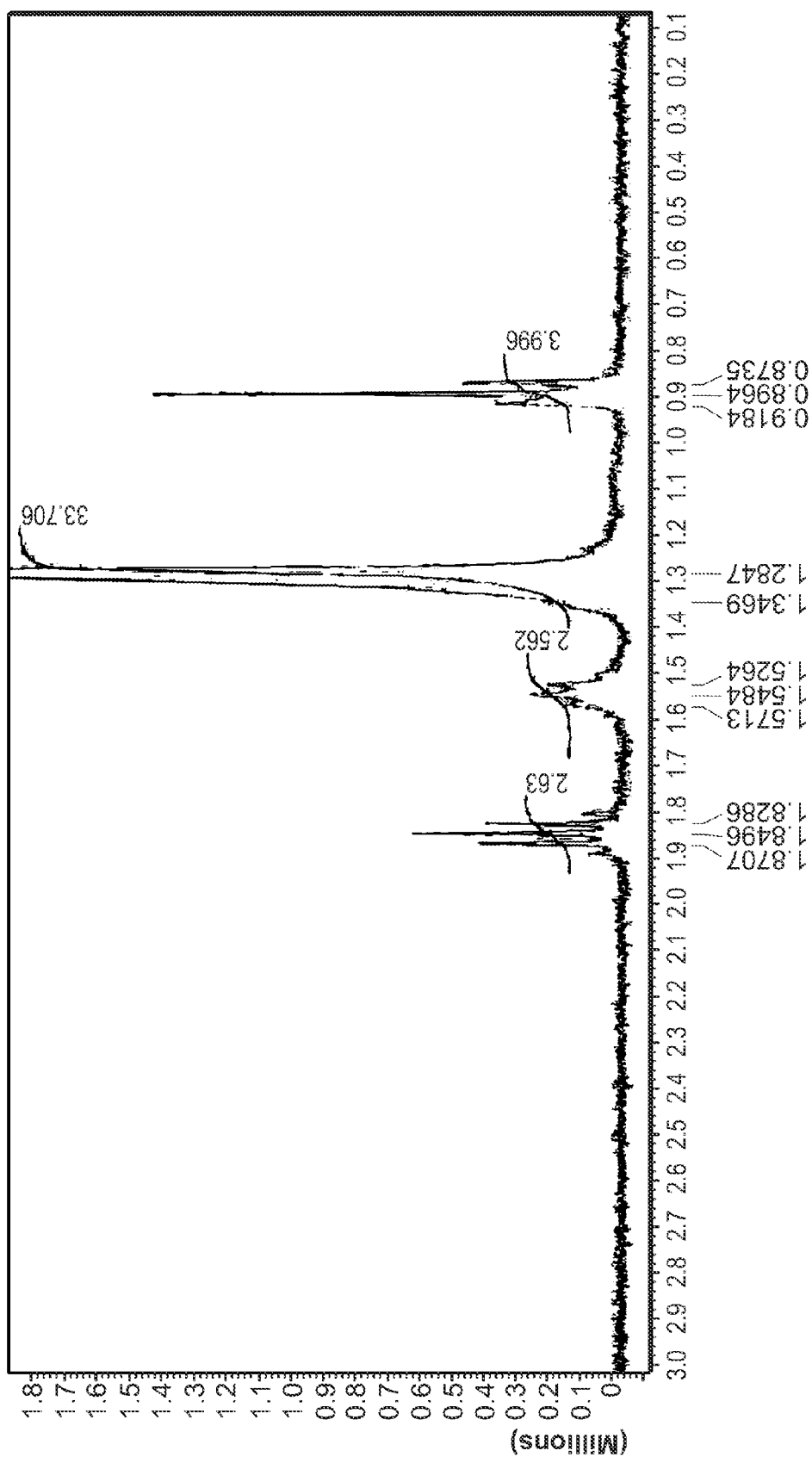
Figure 8E:
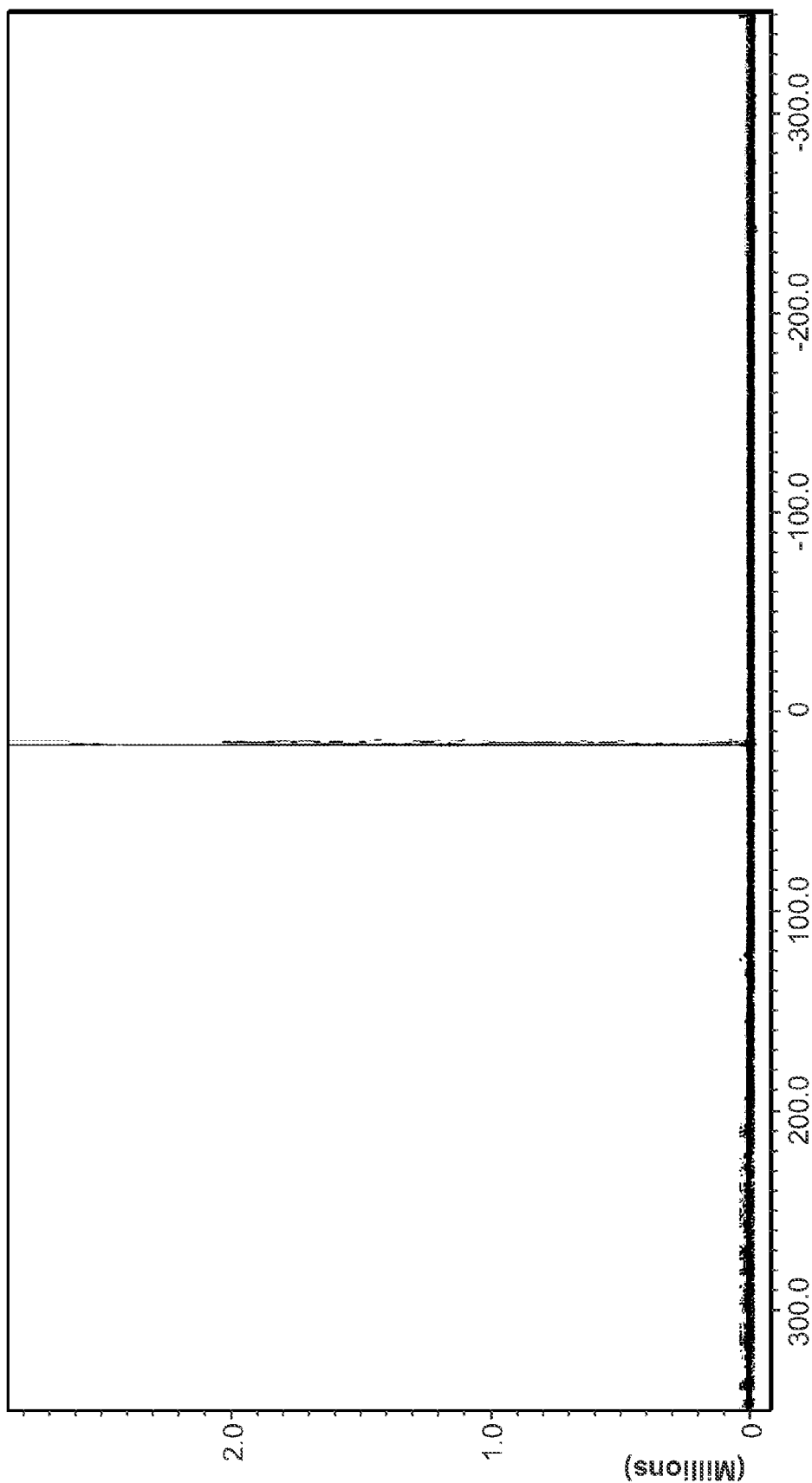
FIGS. 8(e)-(f) are $^{31}$P-NMR spectra of Form A (Lot#5).
Figure 8F:
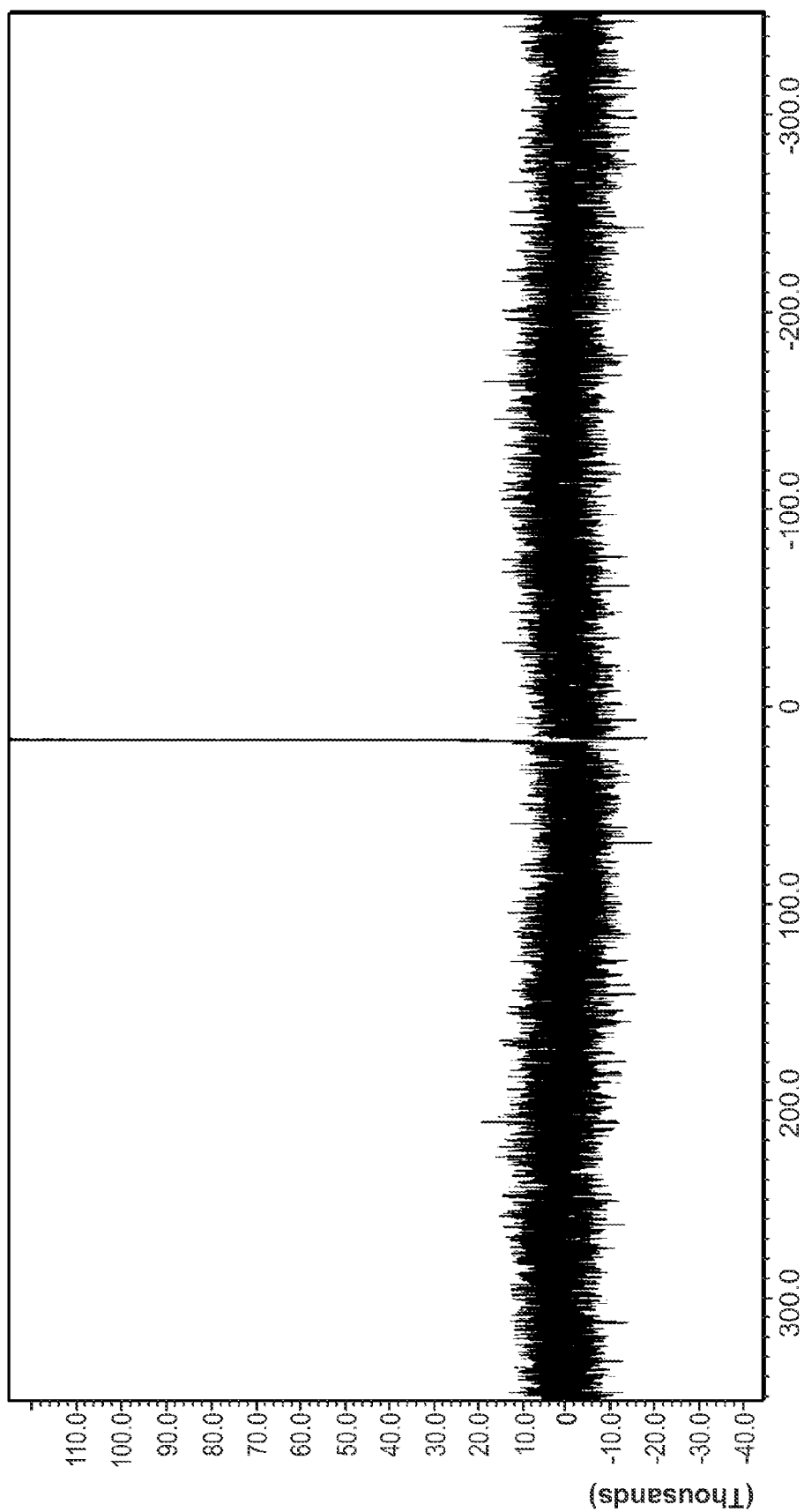

As evident by powder X-ray diffractograms, Lots#1-5 of Form A exhibited substantially the same powder patterns. Indeed, all batches produced by the process described in Example 2 as examined were consistently Form A. As also evident by the overlaid powder X-ray diffractograms in FIG. 7, Form A and Form B exhibited different and distinct powder patterns. A summary of the contrasting diffractograms is shown in Table 16 below.

TABLE 16

Powder XRD differences between Form A and Form B

| Angle (2 θ) | Form A, Lot# 4 | Form B, Lot# 6 |
|---|---|---|
| 5.496 | ✓ | — |
| 5.76 | — | ✓ |
| 11.001 | ✓ | — |
| 11.576 | — | ✓ |
| 12.544 | — | ✓ |
| 13.676 | ✓ | — |
| 14.27 | ✓ | — |
| 17.432 | — | ✓ |
| 17.826 | ✓ | — |
| 19.232 | ✓ | — |
| 23.263 | ✓ | — |
| 23.973 | — | ✓ |

Example 12

Tablet Formulations

Several tablet strengths for CMX001 have been developed. The tablets were compressed from a common blend, while varying the drug load for different strengths. The 20 mg, 50 mg and 100 mg dosage forms, respectively, are round, biconvex tablets with dimensions 7.3 mm×3.5 mm, 7.9 mm×3.8 mm, and 10.5 mm×4.4 mm. CMX001 as the free acid was formulated as direct compression, instant release tablets containing 20, 50 or 100 mg CMX001 (see Tables 17 and 18).

TABLE 17

Composition of 20 mg CMX001 Tablets

| | | Amount per Tablet | |
|---|---|---|---|
| Ingredient | Function | % (wt/wt) | mg/tablet |
| CMX001 | Active Ingredient | 12.50 | 25.00$^y$ |
| Silicified microcrystalline cellulose | Diluent, Binder, Flow aid | 26.88 | 41.50 |
| Mannitol | Diluent | 41.75$^x$ | 66.01$^x$ |
| Microcrystalline cellulose and Mannitol | Diluent, Binder | 13.38 | 19.41 |
| Crospovidone | Disintegrant | 4.50 | 6.48 |
| Magnesium Stearate | Lubricant | 1.00 | 1.60 |
| Total: | | 100.00 | 160.00 |

$^y$The quantity of CMX001 was adjusted based on the drug substance purity factor.
$^x$The target weight of mannitol was adjusted to maintain a constant on a per tablet basis.

TABLE 18

Composition of 50 and 100 mg CMX001 Tablets

| Ingredient | Function | Amount per Tablet % (wt/wt) | Amount per Tablet mg/g |
|---|---|---|---|
| CMX001 | Active Ingredient | 27.78 | 277.8[y] |
| Silicified microcrystalline cellulose | Diluent, Binder, Flow aid | 22.18 | 221.8 |
| Mannitol | Diluent | 34.46[x] | 344.6[x] |
| Microcrystalline cellulose and Mannitol | Diluent, Binder | 11.04 | 110.4 |
| Crospovidone | Disintegrant | 3.714 | 37.14 |
| Magnesium Stearate | Lubricant | 0.8253 | 8.253 |
| Total: | | 100.00 | 1000.00 |

[y]The quantity of CMX001 was adjusted based on the drug substance purity factor.
[x]The target weight of mannitol was adjusted to maintain a constant on a per tablet basis.

Example 13

Stability Studies

Stability studies for 50 mg and 100 mg tablets were completed. Tables 19 and 20 show the results for the 50 mg and 100 mg tablets, respectively.

TABLE 19

Stability Data for CMX001 Tablets, 50 mg

| Test | Specifications | Initial | 1 Month 25° C./60% RH | 1 Month 40° C./75% RH |
|---|---|---|---|---|
| Appearance | White to off-white standard bi-convex tablets | White standard bi-convex tablets | White standard bi-convex tablets | White standard bi-convex tablets |
| Identification | Retention time consistent with standard | Retention time consistent with standard | Retention time consistent with standard | Retention time consistent with standard |
| Water Content | Report Results | 2.03% | 1.51% | 1.49% |
| Assay | 90.0% to 110.0% of label claim | 99.6% of label claim | 100.6% of label claim | 102.3% of label claim |
| Related Substances | Report Individual Related Substances: ≥0.05%; Total Related Substances: NMT 2.5% | RRT 0.64: 0.14% RRT 0.83: 0.16% RRT 1.17: <0.05% RRT 1.33: 0.06% RRT 2.04: 0.05% RRT 2.09: <0.05% RRT 2.41: <0.05% Total: 0.41% | RRT 0.63: 0.12% RRT 0.86: 0.15% RRT 1.33: 0.06% RRT 2.08: 0.05% Total: 0.38% | RRT 0.63: 0.12% RRT 0.86: 0.15% RRT 1.33: 0.05% RRT 2.08: 0.05% Total: 0.37% |
| Dissolution | Report Results at 45 Minutes | Avg.: 98% % RSD: 3.6% | Avg.: 99% % RSD: 1.9% | Avg.: 99% % RSD: 1.2% |

TABLE 20

Stability Data for CMX001 Tablets, 100 mg

| Test | Specifications | Initial | 1 Month 25° C./60% RH | 1 Month 40° C./75% RH |
|---|---|---|---|---|
| Appearance | White to off-white standard bi-convex tablets | White standard bi-convex tablets | White standard bi-convex tablets | White standard bi-convex tablets |
| Identification | Retention time consistent with standard | Retention time consistent with standard | Retention time consistent with standard | Retention time consistent with standard |
| Water Content | Report Results | 2.00% | 1.36% | 1.43% |
| Assay | 90.0% to 110.0% of label claim | 102.1% of label claim | 102.0% of label claim | 99.4% of label claim |
| Related Substances | Report Individual Related Substances: ≥0.05%; Total Related Substances: NMT 2.5% | RRT 0.64: 0.14% RRT 0.83: 0.17% RRT 1.17: <0.05% RRT 1.33: 0.06% RRT 2.05: 0.05% RRT 2.09: <0.05% RRT 2.41: <0.05% Total: 0.42% | RRT 0.62: 0.12% RRT 0.85: 0.15% RRT 1.34: 0.06% RRT 2.10: <LOQ Total: 0.33% | RRT 0.61: 0.12% RRT 0.85: 0.15% RRT 1.33: 0.05% RRT 2.10: <LOQ Total: 0.32% |
| Dissolution | Report Results at 45 Minutes | Avg.: 96% % RSD: 2.7% | Avg.: 95% % RSD: 0.9% | Avg.: 95% % RSD: 2.3% |

Example 14

CMX001 Monoammonium Salt

CMX001 free acid was converted to the monoammonium salt using the following method. A 5 liter round-bottomed flask was equipped with a mechanical stirrer, temperature probe and gas inlet adapter. The flask was charged with CMX001 free acid (87.3 g, 0.155 mol), 2-propanol (180 ml) and 28-30% ammonium hydroxide (13 ml). The reaction was stirred and brought to reflux (62-80° C.) to achieve dissolution (10 min). Note: The solution was not allowed to stir for more than 15 min at reflux. The solution was allowed to cool to less than 25° C. for 16±8 h. The mixture was cooled to 5±5° C. for a minimum of 1 h. The product was filtered and washed with chilled 2-propanol (5±5° C. 430 ml). The product, a white solid, was dried at 30-35° C. for 25 h 10 min±2 h. Yield: approximately 86.8 g (0.15 moles) of CMX001 monoammonium salt; 96.7% of theoretical based on CMX001 free acid. Process monitoring: pH of CMX001 ammonium salt solution.

Equivalents

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. Morphic Form B of phosphonic acid, [[(S)-2-(4-amino-2-oxo-1(2H)-pyrimidinyl)-1-(hydroxymethyl)ethoxy]methyl]mono[3-(hexadecyloxy)propyl]ester characterized by an X-ray diffraction pattern including peaks at about 5.8, 12.5, and 24.0 degrees 2θ.

2. The Morphic Form of claim 1, characterized by an X-ray diffraction pattern further including a peak at 11.6 degrees 2θ.

3. The Morphic Form of claim 1, characterized by an X-ray diffraction pattern further including peaks at 11.6 and 17.4 degrees 2θ.

4. The Morphic Form of claim 1, characterized by an X-ray diffraction pattern further including peaks at 11.6, 17.4, 20.8 and 21.6 degrees 2θ.

5. The Morphic Form of claim 1 characterized by an X-ray diffraction pattern substantially similar to that set forth in FIG. 6.

6. The Morphic Form of claim 1 characterized by an X-ray diffraction pattern substantially similar to that set forth in FIG. 7, lot 6.

7. A pharmaceutical composition comprising a Morphic Form B of phosphonic acid, [[(S)-2-(4-amino-2-oxo-1(2H)-pyrimidinyl)-1-(hydroxymethyl)ethoxy]methyl]mono[3-(hexadecyloxy)propyl]ester and a pharmaceutically acceptable carrier.

8. A method of treating a viral infection in a subject, comprising administering to a subject in need thereof an effective amount of a Morphic Form B of phosphonic acid, [[(S)-2-(4-amino-2-oxo-1(2H)-pyrimidinyl)-1-(hydroxymethyl)ethoxy]methyl]mono[3-(hexadecyloxy)propyl]ester.

9. The method of claim 8, wherein the viral infection is selected from the group consisting of: human immunodeficiency virus (HIV), influenza, herpes simplex virus (HSV), human herpes virus 6 (HHV-6), cytomegalovirus (CMV), hepatitis B and C virus, Epstein-Barr virus (EBV), varicella zoster virus, variola major and minor, vaccinia, smallpox, cowpox, camelpox, monkeypox, ebola virus, papilloma virus, adenovirus or polyoma viruses including John Cunningham virus (JCV), BK virus and Simian vacuolating virus 40 or Simian virus 40 (SV40).

* * * * *